(12) United States Patent
Nasar et al.

(10) Patent No.: US 9,422,529 B2
(45) Date of Patent: Aug. 23, 2016

(54) ALPHAVIRUS COMPOSITIONS AND METHODS OF USE

(71) Applicants: Farooq Nasar, Albany, NY (US); Jesse Erasmus, Galveston, TX (US); Scott C. Weaver, Galveston, TX (US)

(72) Inventors: Farooq Nasar, Albany, NY (US); Jesse Erasmus, Galveston, TX (US); Scott C. Weaver, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/525,820

(22) Filed: Oct. 28, 2014

(65) Prior Publication Data

US 2015/0175975 A1  Jun. 25, 2015

Related U.S. Application Data

(63) Continuation-in-part of application No. 13/923,527, filed on Jun. 21, 2013, which is a continuation-in-part of application No. PCT/US2011/066996, filed on Dec. 22, 2011.

(60) Provisional application No. 61/459,989, filed on Dec. 22, 2010.

(51) Int. Cl.
*C12N 7/00* (2006.01)
*G01N 33/569* (2006.01)
*A61K 39/12* (2006.01)

(52) U.S. Cl.
CPC ............ *C12N 7/00* (2013.01); *G01N 33/56983* (2013.01); *A61K 39/12* (2013.01); *C12N 2770/36121* (2013.01); *C12N 2770/36134* (2013.01); *G01N 2333/181* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 6,592,874 B2 | 7/2003 | Schlesinger et al. | 424/218.1 |
| 7,771,979 B2 * | 8/2010 | Polo et al. | 435/235.1 |
| 2004/0018514 A1 | 1/2004 | Kunst et al. | 435/6.11 |
| 2008/0260698 A1 | 10/2008 | Weaver et al. | 424/93.6 |
| 2011/0171249 A1 * | 7/2011 | Frolov et al. | 424/199.1 |

FOREIGN PATENT DOCUMENTS

WO      WO98/36779      8/1998

OTHER PUBLICATIONS

Nasar et al. Eilat virus, a unique alphavirus with host range restricted to insects by RNA replication. Proc Natl Acad Sci U S A. Sep. 4, 2012;109(36):14622-7.*
Fornadel et al., *Vector Borne Zoonotic Dis.* 2011, 11(8):1173-9.
Hahn et al., *Proc Natl Acad Sci U S A*. 1988, 85(16):5997-6001.
International Preliminary Report on Patentability in International Application No. PCT/US2011/066996 dated Jul. 4, 2013.
International Search Report and Written Opinion in International Application No. PCT/US2011/066996 dated May 11, 2012.
Muriu et al., *Malar J.* 2008, 7:43.
Weaver et al., *J. Virol.* 1997, 71:613-623.

* cited by examiner

*Primary Examiner* — Michelle S Horning
(74) *Attorney, Agent, or Firm* — Norton Rose Fulbright US LLP

(57) ABSTRACT

Embodiments are directed compositions related to Eilat virus and uses thereof. Certain aspects are directed to the detection of non-Eilat entities using a chimeric Eilat *alphavirus* as a capture agent.

13 Claims, 17 Drawing Sheets

A)

B)

| Virus | nsP1 CSE | |
|---|---|---|
| Eilat | CAUGGUCACCCGAAUGACCACGCCAAUGCCGAGAGCCUUCCCAUGCGC | SEQ ID NO:7 |
| Trocara | GCA....UG.C...............U............G.......CUG. | SEQ ID NO:8 |
| Aura | GCA........U.............U............G.......CUG. | SEQ ID NO:9 |
| Whataroa | GCA...C..G..A............U.U..C........G.......CUG. | SEQ ID NO:10 |
| Sindbis | GCA.....U..A.............U..............U.....G.......CUG. | SEQ ID NO:11 |
| WEE | GCA....UGAC..C...........U..C.........A.U......G.......GUG. | SEQ ID NO:12 |
| EEE | GCA....UGAC..............U..C.........A.U......G.......CCUA. | SEQ ID NO:13 |
| VEE | GCA....UGAU..............U..U....G....U.G......G.......CUG. | SEQ ID NO:14 |
| Chikungunya | GCA....AU...............U..U....U.....G........G.......CUA. | SEQ ID NO:15 |
| Ross River | GCA....A..U.............U..C............U......G.......CUG. | SEQ ID NO:16 |
| Una | GCA....U..A.............G..C...........U......G.......CCU. | SEQ ID NO:17 |
| Semliki Forest | GCA....A..A.............U..A..........A.U......G.......CCUG. | SEQ ID NO:18 |
| Middelburg | GCA....A................U..C..........U.U......G.......CCUU. | SEQ ID NO:19 |
| Barmah Forest | GCA.AC..A..A............AC.C...........U......G.......CCUU. | SEQ ID NO:20 |
| Ndumu | GCA....A................U..U.......A..G.U......G.......CUU. | SEQ ID NO:21 |
| SES | GCA....A..U.............U..C..........U.U......G.......CUG. | SEQ ID NO:22 |
| SPD | .AUAGGU.GU.U..C.........U..GCC..........C.....U.......C..UG. | SEQ ID NO:23 |

FIG. 2A

| B) Virus | nsP1/nsp2 | nsP2/nsP3 | nsP3/nsP4 | Capsid/E3 | E3/E2 | |
|---|---|---|---|---|---|---|
| Eilat | DIGG/ALVE | GVGA/APSY | GAGG/YIFS | TVEW/SATV | RARR/AVAP | SEQ ID NO:24, 25, 26, 27, 28 |
| Trocara | ...A/....D | .I.C/..... | .V../..... | ..K../..AT | .PK../STEL | SEQ ID NO:29, 30, 31, 32, 33 |
| Aura | .A..A/..... | .S../..... | .V../..... | ..../.RAI | .HV./STPT | SEQ ID NO:34, 35, 36, 37, 38 |
| Whataroa | ...A/..... | ..../..... | .V../..... | ..E../..AA | .HK./SITD | SEQ ID NO:39, 40, 41, 42, 43 |
| Sindbis | ...A/..... | ..../..... | .V../..... | ..E../..AP | .SK./S..ID | SEQ ID NO:44, 45, 46, 47, 48 |
| WEE | EA.A/GS.. | EA.R/..A. | E../A.... | SES./..LVT | .QK./SITD | SEQ ID NO:49, 50, 51, 52, 53 |
| EEE | EA.A/GS.. | EA.R/..A. | E../A.... | SEP./..LAT | .T../DLDT | SEQ ID NO:54, 55, 56, 57, 58 |
| VEE | EA.A/G

A)

| Virus | subgenomic promoter | |
|---|---|---|
| Eilat | CCCUCUACAACUAACCUAAAUAGU | SEQ ID NO:109 |
| Aura | A.......GGUGGU.........A | SEQ ID NO:110 |
| Whataroa | AG......GG.GGU.........A | SEQ ID NO:111 |
| Sindbis | AU......GGUGGU.......... | SEQ ID NO:112 |
| WEE | ........GG..G........... | SEQ ID NO:113 |
| EEE | ........GG..G........... | SEQ ID NO:114 |
| VEE | .U......GG.......G...G.A | SEQ ID NO:115 |
| Chikungunya | .UU.....GG.GGU...G...G.G | SEQ ID NO:116 |
| Ross River | A.......GGUGGU.........A | SEQ ID NO:117 |
| Semliki Forest | A.......GG.GGU....G..U.G | SEQ ID NO:118 |
| Middelburg | A.......GG.GGU.......... | SEQ ID NO:119 |
| Barmah Forest | AU......GGUGGU.......... | SEQ ID NO:120 |
| SES | .G......GG..GU.........A | SEQ ID NO:121 |
| SPD | ........GU.......U....U. | SEQ ID NO:122 |

B)

| Virus | 3' CSE | |
|---|---|---|
| Eilat | AAUUUGUUUUUAAUAUUCC | SEQ ID NO:123 |
| Aura | .U................. | SEQ ID NO:124 |
| Sindbis | .U..........C...... | SEQ ID NO:125 |
| WEE | .U............A.... | SEQ ID NO:126 |
| EEE | .U................. | SEQ ID NO:127 |
| VEE | .U................. | SEQ ID NO:128 |
| Ross River | G................UAC | SEQ ID NO:129 |
| Semliki Forest | ....G.............. | SEQ ID NO:130 |
| Middelburg | CUA...G.........C.. | SEQ ID NO:131 |
| Barmah Forest | .U..GU...........UAC | SEQ ID NO:132 |
| SPD | CUA...G......A....U.AAUAC | SEQ ID NO:133 |

| Virus | E1 fusion peptide | | Ribosomal binding site | |
|---|---|---|---|---|
| Eilat | GVYPFMWGGAQCFCDTEN | SEQ ID NO:135 | KPGKRERTAIRLQAD | SEQ ID NO:152 |
| Trocara | ........ES... | SEQ ID NO:136 | ...Q.M.MKFE.. | SEQ ID NO:153 |
| Aura | ...L....S... | SEQ ID NO:137 | ...Q....KFE.. | SEQ ID NO:154 |
| Whataroa | ........S... | SEQ ID NO:138 | ...Q.MV.K.E.. | SEQ ID NO:155 |
| Sindbis | ........S... | SEQ ID NO:139 | ...Q.M..K.E.. | SEQ ID NO:156 |
| WEE | ........S... | SEQ ID NO:140 | ...Q.MCMK.ES. | SEQ ID NO:157 |
| EEE | ....Y....... | SEQ ID NO:141 | ...Q.MCMK.ES. | SEQ ID NO:158 |
| VEE | ....Y....... | SEQ ID NO:142 | ...Q.MVMK.ES. | SEQ ID NO:159 |
| Chikungunya | ....Y....... | SEQ ID NO:143 | ...R..MCMKIEN. | SEQ ID NO:160 |
| Ross River | ....Y..S... | SEQ ID NO:144 | ...R..MCMKIEN. | SEQ ID NO:161 |
| Una | ...L.Y....... | SEQ ID NO:145 | NL....MCMKIEN. | SEQ ID NO:162 |
| Semliki Forest | ....Y..S... | SEQ ID NO:146 | ......MCMKIEN. | SEQ ID NO:163 |
| Middelburg | ...L.Y..NS... | SEQ ID NO:147 | ......KCMKIEN. | SEQ ID NO:164 |
| Barmah Forest | ....Y....... | SEQ ID NO:148 | ...M.NCMKIEN. | SEQ ID NO:165 |
| Ndumu | .Y..Y..SS... | SEQ ID NO:149 | ......KCMKIES. | SEQ ID NO:166 |
| SES | ...L.Y..S... | SEQ ID NO:150 | ......ACMKIES. | SEQ ID NO:167 |
| SPD | N..LL..A.H..S... | SEQ ID NO:151 | R...EV.ISVKCARQ | SEQ ID NO:168 |

| MIAF | Eilat Antigen Ht/Ho* |
|---|---|
| Trocara | 8/≥256 |
| Aura | 8/≥256 |
| Sindbis | 16/≥256 |
| Whataroa | <8/16 |
| WEE | <8/≥128 |
| Fort Morgan | <8/≥256 |
| Highlands J | <8/64 |
| EEE | 8/≥256 |
| VEE | 16/≥256 |
| VEE IIIA (Mucambo) | <8/≥256 |
| VEE IV (Pixuna) | <8/≥256 |
| VEE II (Everglades) | <8/≥256 |
| Mayaro | <8/≥256 |
| Una | <8/≥256 |
| Bebaru | <8/≥256 |
| Ross River | <8/≥256 |
| Getah | <8/≥256 |
| Chikungunya | <8/≥256 |
| O'nyong-nyong | <8/≥256 |
| Semliki Forest | <8/≥256 |
| Middelburg | <8/≥256 |
| Ndumu | <8/≥256 |
| Barmah Forest | <8/≥256 |

B)

| Antigen | Eilat Antibody Ht/Ho* |
|---|---|
| Trocara | 20/10240 |
| Sindbis | 40/5120 |
| WEE | 40/2560 |
| EEE | 20/2560 |
| Aura | <20/5120 |
| Mayaro | <20/5120 |
| Una | <20/5120 |
| Getah | <20/10240 |
| Chikungunya | <20/5120 |
| Semliki Forest | <20/2560 |

ALPHAVIRUS COMPOSITIONS AND METHODS OF USE

This application is a continuation in part of U.S. patent application Ser. No. 13/923,527 filed Jun. 21, 2013 (pending); which is a continuation in part of International Patent Application number PCT/US2011/066996 filed Dec. 22, 2011 (expired), which is a non-provisional application claiming priority to U.S. Provisional Patent Application Ser. No. 61/459,989 filed Dec. 22, 2010. This application claims priority to and incorporates by reference each of the above referenced applications in their entirety.

STATEMENT REGARDING FEDERALLY FUNDED RESEARCH

This invention was made with government support under N01-AI-30027 awarded by the National Institutes of Health/National Institute of Allergy and Infectious Disease. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Current classification of the genus *Alphavirus* includes 29 species that can be classified into nine complexes based on antigenic and/or genetic similarities (Powers et al., *J Virol.*, 2001, 75(21):10118-31). Barmah Forest, Ndumu, Middelburg, and Semliki Forest complexes consist of almost exclusively Old World viruses whereas Venezuelan equine encephalitis (VEE), Eastern equine encephalitis (EEE), and Trocara complexes are comprised of New World viruses (id.). Western equine encephalitis (WEE) complex contains both Old World (Whataroa and Sindbis) and New World (Aura) viruses as well as recombinant viruses (WEE, Highland J, Fort Morgan, and Buggy Creek) (Powers et al., *J Virol.*, 2001, 75(21):10118-31; Hahn et al., *Proc Natl Acad Sci USA*. 1988, 85(16):5997-6001; Weaver et al., *J. Virol.* 1997, 71:613-623). The latter viruses are decedents of a recombinant virus that obtained nonstructural and capsid genes from an EEE-like virus and the remaining genes from a Sindbis-like virus (Hahn et al., *Proc Natl Acad Sci USA*. 1988, 85(16):5997-6001; Weaver et al., *J. Virol.* 1997, 71:613-623). Lastly, the aquatic *alphavirus*, salmonid *alphavirus* (SAV), consists of two species, salmon pancreatic disease virus (SPDV) and sleeping sickness virus (SDV) that are distantly related to all other alphaviruses (Weston et al., *J Virol.* 2002, 76(12):6155-63).

Most alphaviruses are maintained in natural cycles between arthropod vectors, mainly mosquitoes, and susceptible vertebrate hosts (Strauss and Strauss, *Microbiol Rev.* 1994, 58(3):491-562). Occasionally, these cycles can spill over into the human and animal populations, and can cause disease. Human infections with Old World viruses such as Ross River (RRV), chikungunya (CHIKV), and Sindbis (SINV) are characterized by febrile illness, rash and polyarthritis (id.). In contrast, infections with New World viruses, Venezuelan equine encephalitis (VEEV), Eastern equine encephalitis (EEEV) and Western equine encephalitis (WEEV), can cause fatal encephalitis. The ability of alphaviruses to infect both invertebrates and vertebrates facilitates a broad host range that enables the viruses to be maintained in ecological niches with sporadic outbreaks in humans and animals. As such, alphaviruses have been shown to either naturally or experimentally infect many vertebrate and invertebrate hosts. Alphaviruses have been shown to infect mosquito species encompassing three genera (*Aedes* sp., *Culex* sp., *Anopheles* sp.) as well as ticks and lice (Griffin. Alphaviruses, In: Fields B N, Knipe D M, Howley P M, editors. Virology. 5th edition. New York, N.Y.: Lippincott-Raven; Pages 1023-68; Linthicum et al., *J Med Entomol.* 1991, 28(3): 405-9; La Linn et al., *J Virol.* 2001, 75(9):4103-9). Vertebrate hosts include fish, equids, birds, amphibians, reptiles, rodents, pigs, humans, and non-human primates (Griffin. Alphaviruses, In: Fields B N, Knipe D M, Howley P M, editors. Virology. 5th edition. New York, N.Y.: Lippincott-Raven; Pages 1023-68; Burton et al., *Science* 1966, 154(752): 1029-31). Consequently, they can be readily cultured in vitro in many vertebrate and invertebrate cell lines (Way et al., *J Gen Virol.* 1976, 30(1):123-30; Sarver and Stollar, *Virology* 1977, 80(2):390-400; Igarashi, *J Gen Virol.* 1978, 40(3):531-44). Whereas distantly related fish alphaviruses, which are not known to have arthropod vectors, exhibit a narrow host range that is at least partially due to temperature (Weston et al., *Virology* 1999, 256(2):188-95; Villoing et al., *J Virol.* 2000, 74(1):173-83; Graham et al., *J Fish Dis.* 2008, 31(11): 859-68).

The viral factor(s) that underlie the broad host range of mosquito-borne alphaviruses are poorly understood. Host-restricted viruses may provide insight into these factor(s) and provide vector delivery platforms for expression or attenuation in specific hosts. But until the present invention, no mosquito-only alphaviruses were known in the genus *Alphavirus*.

SUMMARY

Described herein is a new *alphavirus*, Eilat virus (EILV), including nucleic acid compositions, protein compositions, viral compositions, and methods of using the same.

Certain embodiments are directed to a recombinant *alphavirus* expression cassette comprising an *alphavirus* nucleic acid segment having a nucleic acid sequence that is at least 95% identical to the nucleic acid sequence of SEQ ID NO:1 or a fragment thereof. In certain aspects the expression cassette is incorporated into isolated nucleic acids, expression vectors, or plasmids comprising all or part of an EILV nucleic acid sequence (SEQ ID NO:1). In certain aspects the nucleic acid is a recombinant DNA. The EILV nucleic acids can have at least 80, 85, 90, 95, 98, 99, or 100% sequence identity to SEQ ID NO:1 or any 10, 20, 30, 40, 50, 100, 200, 300, 400, 500, 600, 700, 800, 1000, 2000, 3000, 4000, 5000, 6000, 7000, 8000, 9000, 10000, 11000 consecutive nucleotide segment thereof, including all values and ranges there between. In certain aspects, a nucleic acid comprises a nucleotide sequence that is at least 80, 85, 90, 95, 98, 99, or 100% identical to all or a part of the non-structural protein coding region of EILV (nucleotides 57 to 7304 of SEQ ID NO:1, or any 10, 20, 30, 40, 50, 100, 200, 300, 400, 500, 600, 700, 800, 1000, 2000, 3000, 4000, 5000, 6000, or 7000 consecutive nucleotide segment thereof, including all values and ranges there between). In a further aspect, a nucleic acid comprises a nucleotide sequence that is at least 80, 85, 90, 95, 98, 99, or 100% identical to all or a part of the structural protein coding region of EILV (nucleotides 7387 to 11088 of SEQ ID NO:1, or any 10, 20, 30, 40, 50, 100, 200, 300, 400, 500, 600, 700, 800, 1000, 2000, 3000, 4000, 5000, 6000, 7000, 8000, 9000, or 10000 consecutive nucleotide segment thereof, including all values and ranges there between).

In certain aspects, the nucleotide segments specifically bind EILV nucleic acids and distinguish EILV from other alphaviruses under the appropriate conditions. In certain aspects the nucleotide segments are synthetic oligonucleotides. In a further aspect the oligonucleotide is a DNA oligonucleotide or analog thereof.

The EILV nucleic acids described herein can be in the form of isolated or recombinant nucleic acids or included in a recombinant *alphavirus* replicon, a virus, an *alphavirus*, a viral particle, an *alphavirus* particle, an expression cassette, a host cell, an *alphavirus* vector, and the like. In still a further aspect, an *alphavirus* nucleic acid sequence can comprise a heterologous nucleic acid segment. In certain aspects, the heterologous nucleic acid segment can encode a therapeutic protein, an antigen, a toxin, or a marker. In certain aspects the heterologous nucleic acid is configured to produce a fusion protein that is expressed on the surface of the chimeric EILV. The fusion protein can be a variant of a EILV envelope protein with a heterologous protein or peptide attached or fused to EILV envelope protein.

Certain aspects are directed to an isolated, recombinant, and/or purified EILV polypeptide or peptide having at least 85, 90, 95, 98, 99, or 100% amino acid sequence identity to all or part of the amino acid sequence of SEQ ID NO:3 (EILV non-structural polyprotein) or SEQ ID NO:5 (EILV structural polyprotein). The term "polyprotein" refers to a polypeptide that is post-translationally cleaved to yield more than one polypeptide. "Polypeptide" refers to any peptide or protein comprising a chain or polymer of amino acids joined to each other by peptide bonds. "Polypeptide" refers to both short chains of 100 amino acids or less, commonly referred to as peptides, and to longer chains, generally referred to as proteins. "Polypeptides" may contain amino acids other than the 20 gene-encoded amino acids. "Polypeptides" include amino acid sequences modified either by natural processes, such as post-translational processing, or by chemical modification techniques, which are well known in the art.

In certain aspects, the isolated and/or purified EILV protein has at least 85, 90, 95, 98, 99, or 100% amino acid sequence identity to all or part of the amino acid sequence of an EILV non-structural protein including: an EILV nsP1 (amino acids 1 to 543 of SEQ ID NO:3, or any peptide having 5, 10, 15, 20, 30, 40, 50, 60, 70, 80, 90, 100, 200, 300, or 400 consecutive amino acids of SEQ ID NO:3 including all values and ranges there between), an EILV nsP2 (amino acids 544 to 1352 of SEQ ID NO:3, or any peptide of 5, 10, 15, 20, 30, 40, 50, 60, 70, 80, 90, 100, 200, 300, 400, 500, 600, or 700 consecutive amino acids of SEQ ID NO:3 including all values and ranges there between), an EILV nsP3 (amino acids 1353 to 1808 of SEQ ID NO:3, or any peptide of 5, 10, 15, 20, 30, 40, 50, 60, 70, 80, 90, 100, 200, 300, or 400 consecutive amino acids of SEQ ID NO:3 including all values and ranges there between) or an EILV nsP4 (amino acids 1809 to 2415 of SEQ ID NO:3, or any peptide of 5, 10, 15, 20, 30, 40, 50, 60, 70, 80, 90, 100, 200, 300, 400, or 500 consecutive amino acids of SEQ ID NO:3 including all values and ranges there between).

In certain aspects, the isolated and/or purified EILV protein has at least 85, 90, 95, 98, 99, or 100% amino acid sequence identity to all or part of the amino acid sequence of an EILV structural protein including: an EILV C protein (amino acids 1 to 255 of SEQ ID NO:5, or any peptide of 5, 10, 15, 20, 30, 40, 50, 60, 70, 80, 90, 100, or 200 consecutive amino acids of SEQ ID NO:5 including all values and ranges there between), an EILV E2 protein (amino acids 319 to 739 of SEQ ID NO:5, or any peptide of 5, 10, 15, 20, 30, 40, 50, 60, 70, 80, 90, 100, 200, or 300 consecutive amino acids of SEQ ID NO:5 including all values and ranges there between), an EILV E1 protein (amino acids 795 to 1233 of SEQ ID NO:5, or any peptide of 5, 10, 15, 20, 30, 40, 50, 60, 70, 80, 90, 100, 200, or 300 consecutive amino acids of SEQ ID NO:5 including all values and ranges there between), an EILV E3 protein (amino acids 256 to 318 of SEQ ID NO:5, or any peptide of 5, 10, 15, 20, 30, 40, or 50 consecutive amino acids of SEQ ID NO:5 including all values and ranges there between), or an EILV 6K (amino acids 740 to 794 of SEQ ID NO:5, or any peptide of 5, 10, 15, 20, 30, or 40 consecutive amino acids of SEQ ID NO:5 including all values and ranges there between). In certain aspects, an immunogenic composition comprises all or part of 1, 2, 3, 4, 5, 6, 7, 8, or 9 EILV proteins. In a further aspect, an immunogenic composition comprises all or part of one or more EILV structural proteins. In another aspect, an immunogenic composition comprises all or part of one or more EILV non-structural proteins. In certain aspects the EILV E1, E2, and/or E3 is a fusion protein comprising a heterologous protein or peptide. In certain aspects the heterologous protein or peptide is immunogenic.

Other embodiments are directed to alphaviruses comprising all or part of the EILV nucleic acid sequence of SEQ ID NO: 1. In certain aspects the *alphavirus* is a recombinant *alphavirus*. Certain embodiments are directed to an *alphavirus* having a genome comprising (a) an *alphavirus* nucleic acid segment that is at least 95% identical to a corresponding segment of SEQ ID NO:1 and (b) a heterologous gene. In certain aspects, the *alphavirus* is chimeric and comprises certain segments of an EILV *alphavirus* and other segments from a non-EILV *alphavirus*. A non-EILV *alphavirus* includes, but is not limited to Ross River (RRV), chikungunya (CHIKV), Sindbis (SINV), Venezuelan equine encephalitis (VEEV), Eastern equine encephalitis (EEEV), Western equine encephalitis (WEEV), or an aquatic or Salmonid *alphavirus*. In certain aspects the Eilat chimeric virus is an EILV/CHIKV chimera. In certain aspects the EILV/CHIK chimera has a nucleotide sequence 90, 95, 98, 99, to 100% identical to SEQ ID NO:134. An EILV/CHIK chimeric *alphavirus* can have a plasmid structure as illustrated in FIG. 14. In certain embodiments the chimeric *alphavirus* only replicates in an arthropod host. Such chimeric alphaviruses can comprise an EILV nucleic acid with 1, 2, 3, 4, or 5 of the structural gene regions coding for C, E3, E2, 6K, or E1 proteins substituted with a corresponding non-EILV region or segment.

Still further embodiments are directed to immunogenic compositions comprising an EILV nucleic acid, EILV polypeptide, EILV virus, or *alphavirus* comprising all or part of an EILV nucleic acid or all or part of 1, 2, 3, 4, 5, 6, 7, 8, or 9 EILV proteins. Certain aspects are directed to one or more recombinant EILV nucleic acid, recombinant EILV polypeptide, recombinant EILV virus, or recombinant *alphavirus* comprising all or part of an recombinant EILV nucleic acid or all or part of 1, 2, 3, 4, 5, 6, 7, 8, or 9 recombinant EILV proteins. Certain embodiments are directed to virus like particle comprising a recombinant nucleic acid described herein.

Pharmaceutical formulations, such as vaccines, of the present invention comprise an immunogenic amount of *alphavirus* or viral particle comprising *alphavirus* proteins or antigens, as disclosed herein, in combination with a pharmaceutically acceptable carrier.

Other embodiments are directed to alphaviruses as arthropod expression systems. These expression systems include all or part of the EILV nucleic acid sequence of SEQ ID NO:1 and a heterologous gene (e.g., a toxin) for expression in arthropods (e.g., mosquitoes). For example, the heterologous gene can be a gene (e.g., antisense or short interfering nucleotide) that disrupts replication or hinders transmission of an arthropod-borne infectious disease including, but not limited to, *alphavirus* infections (e.g., Chikungunya), flavivirus infections (e.g., Dengue), and malaria (*Plasmodium*). See, e.g., Ito et al. "Transgenic anopheline mosquitoes impaired in transmission of a malaria parasite." *Nature* 417: 452-455 (2002); Olson K E et al. "Genetically Engineered Resistance to Dengue-2 Virus Transmission in Mosquitoes." *Science* 272 (5263):884-86 (1996). In still other embodiments, the heterologous gene can be toxic to the arthropod (e.g., a bacterial gene such as from *Wolbachia*), thus killing or reducing the longevity of the arthropod. See, e.g., Moreira L et al. "A *Wolbachia* Symbiont in *Aedes aegypti* Limits Infection with Dengue, Chikungunya, and *Plasmodium*." *Cell* 139:1268-78 (2009).

Certain embodiments are directed to kits for detecting *alphavirus* infection and methods of using such kits to detect *alphavirus* infection. In certain aspects the methods comprise contacting a biological sample from a subject with a substrate having one or more capture antigens (chimeric EILV) attached that are capable of capturing a target polypeptide (e.g., an anti non-EILV *alphavirus* antibody) and detecting a captured target polypeptide. In certain aspects detection is with a labeled probe bound, directly or indirectly, to the captured target polypeptide. In certain aspects the capture agent is a chimeric EILV virus. In a further aspect the chimeric EILV virus is an EILV/CHIKV, EILV/EEEV, EILV/WEEV, EILV/VEEV chimera. The presence of a target polypeptide in the biological sample is indicative of a viral infection of the subject or exposure of the subject to a target virus. In a further aspect the target polypeptide is anti-virus antibodies. In certain aspects the labeled probe is detected by fluorescence detection, chemiluminescence detection, or colorimetric detection. In certain embodiments the EILV chimera is immobilized.

In certain aspects the sample is a biological sample. In a further aspect the biological sample is a biological fluid such as sputum, blood, urine, cerebral spinal fluid (CSF), and the like. In certain aspect the sample is blood or a blood fraction.

The term "recombinant" refers to an artificial combination of two otherwise separated segments of nucleic acid, e.g., by chemical synthesis or by the manipulation of isolated segments of nucleic acids by genetic engineering techniques.

An "immunogenic amount" is an amount of *alphavirus* or viral particles comprising *alphavirus* antigens sufficient to evoke an immune response in a subject administered an immunogenic composition. An amount of from about $10^1$ to about $10^{10}$ plaque forming units (pfu) per dose is believed suitable, depending upon the age and species of the subject being treated. Subjects that can be administered immunogenic amounts of a composition described herein, e.g., EILV virus or host-range restricted EILV-containing *alphavirus* chimeras, include but are not limited to human, mammal, and other animal subjects (e.g., horse, donkey, mouse, hamster, monkeys), including livestock and laboratory animals. Administration may be by any suitable route, such as intraperitoneal, intravenous, subcutaneous, or intramuscular injection.

The term "*alphavirus*" has its conventional meaning, and includes the various species of alphaviruses, including the newly identified Eilat virus, as well as Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, Buggy Creek virus, the salmonid alphaviruses and the like.

The term "*alphavirus* replicon" is used to refer to a nucleic acid molecule expressing *alphavirus* nonstructural protein genes such that it can direct its own replication (amplification).

The term "*alphavirus* replicon particle" refers to a virion or virion-like structural complex incorporating an *alphavirus* replicon.

*Alphavirus*-permissive cells are cells that, upon transfection with the viral RNA transcript, are capable of producing viral particles.

The term "expression vector" refers to a nucleic acid that is capable of directing the expression of a sequence(s) or gene(s) of interest. The vector construct can include a 5' sequence capable of initiating transcription of a nucleic acid, e.g., all or part of an *alphavirus*. Expressed nucleic acid can code for biologically active *alphavirus* non-structural proteins (e.g., nsP1, nsP2, nsP3, and nsP4), and an *alphavirus* RNA polymerase recognition sequence. In addition, the vector construct may include a viral junction region. The vector may also include nucleic acid molecule(s) to allow for production of virus, a 5' promoter that is capable of initiating the synthesis of viral RNA in vitro from cDNA, as well as one or more restriction sites, and a polyadenylation sequence. In addition, the constructs may contain selectable markers such as Neo, SV2 Neo, hygromycin, phleomycin, histidinol, and DHFR. Furthermore, the constructs can include plasmid sequences for replication in host cells and other functionalities known in the art. In certain aspects the vector construct is a DNA construct.

"Expression cassette" refers to a recombinantly produced nucleic acid molecule capable of directing the expression of one or more proteins. The expression cassette includes a promoter capable of directing the expression of a target protein(s), and a sequence encoding one or more proteins, e.g., proteins comprising *alphavirus* structural protein(s) or heterologous nucleic acids in the context of *alphavirus*. Optionally, the expression cassette may include transcription termination, splice recognition, and polyadenylation addition sites. Promoters include the CMV, MMTV, MoMLV, and adenovirus VA1RNA promoters. In addition, the expression cassette may contain selectable markers such as Neo, SV2 Neo, hygromycin, phleomycin, histidinol, and DHFR.

"Virus-like particle" refers to an infective and/or immunogenic non-virus particle containing viral nucleic acids and/or proteins. In certain aspects, viral envelope proteins are included in a lipid bilayer or a viral nucleic acid is encapsulated within a lipid bilayer.

"Antigen" refers to a molecule containing one or more epitopes (either linear, conformational or both) that will stimulate a host's immune system to make a humoral and/or cellular antigen-specific response. The term is used interchangeably with the term "immunogen." The term "antigen" denotes both subunit antigens (i.e., antigens that are separate and discrete from a whole organism with which the antigen is associated in nature), as well as non-replicative, killed, attenuated, or inactivated bacteria, viruses, fungi, parasites or other microbes.

An "immune response" to an antigen or composition is the development in a subject of a humoral and/or a cellular immune response to an antigen present in the composition of interest. A "humoral immune response" refers to an immune response mediated by antibody molecules, while a "cellular immune response" is one mediated by T-lymphocytes and/or other white blood cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, for example, Erickson et al., J. Immunol. 151:4189-4199, 1993; Doe et al., Eur. J. Immunol. 24:2369-2376, 1994. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J. and O'Callaghan, C. A., J. Exp. Med. 187 (9):1367-1371, 1998; Mcheyzer-Williams, M. G. et al., Immunol. Rev. 150:5-21, 1996; Lalvani, A. et al., J. Exp. Med. 186:859-865, 1997).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

Figure 14:
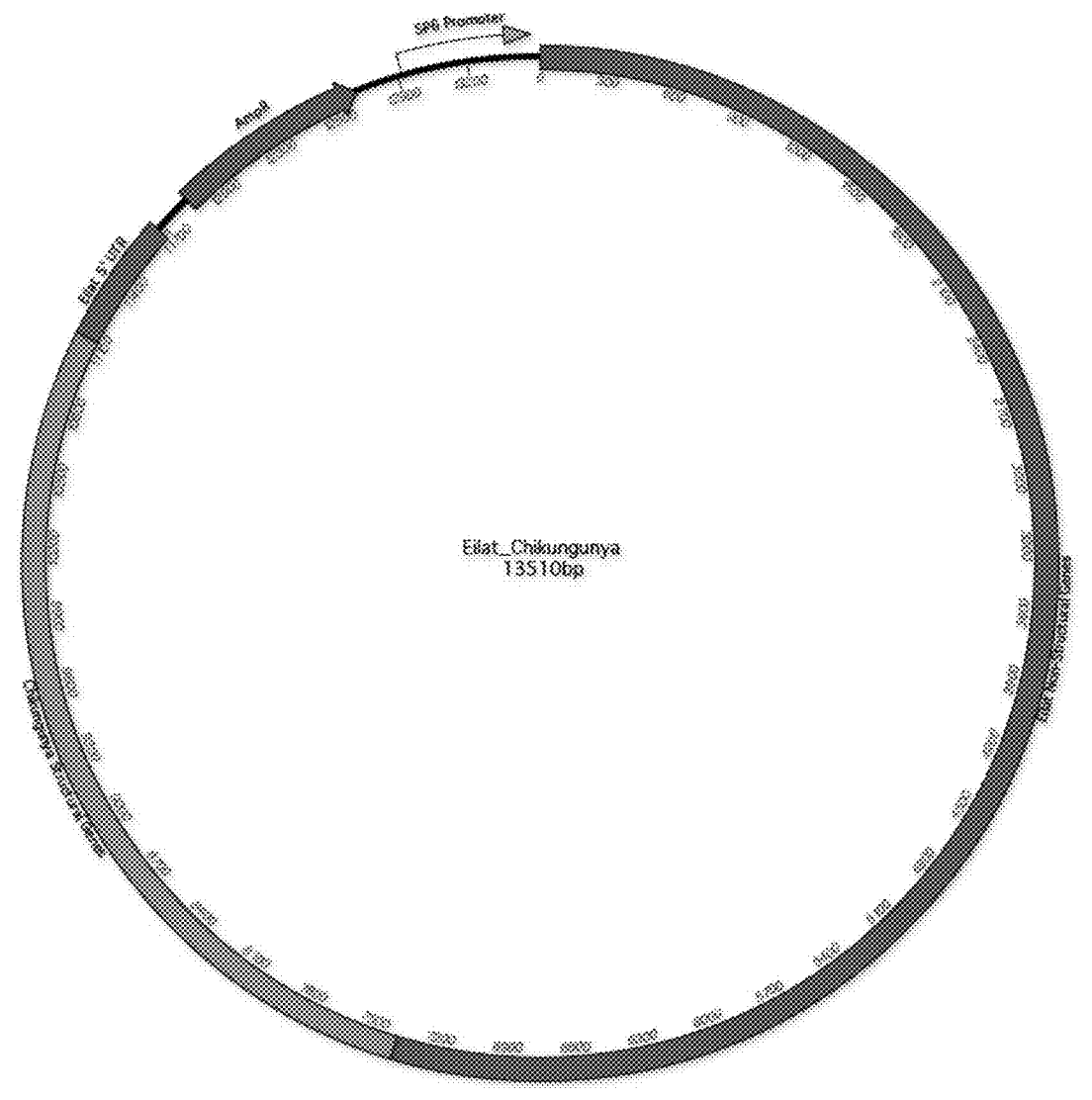

FIG. 14. Illustration of the plasmid map for an Eilat/Chikungunya chimeric *alphavirus*.

DESCRIPTION

Figure 1A:
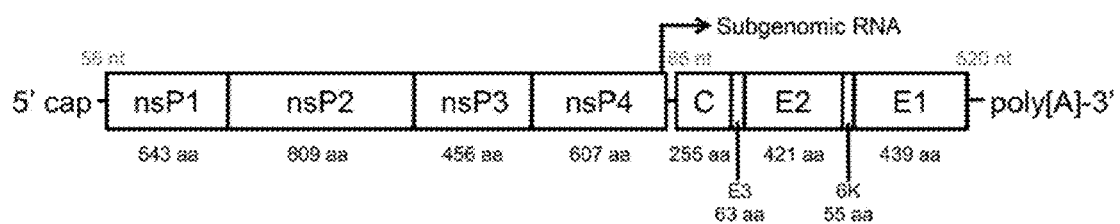
FIGS. 1A-1B. (A) Diagram of the EILV genome. Amino acid size of each protein is provided, as well as the intergenic region, 5' and 3'UTR nucleotide size. (B) Cloning strategy of full-length Eilat virus cDNA clone. Endonuclease sites within EILV sequence, and pRS2 rest cell lines with a virus comprising the EILV/SIN marker genome, light and fluorescent image.

The genus *Alphavirus* in the family Togaviridae is comprised of small, spherical, enveloped viruses with a genome consisting of single strand, positive-sense RNA approximately 11-12 kb in length (Kuhn R J. Togaviridae: The viruses and their replication, In: Fields B N, Knipe D M, Howley P M, editors. Virology. 5th edition. New York, N.Y.: Lippincott-Raven; Pages 1001-22). The genome contains two open reading frames: the 5' two-thirds of the genome encodes four nonstructural proteins (nsP1, nsP2, nsP3, and nsP4); and the 3' one-third of the genome encodes for structural proteins (Capsid, E2, E1). Alphaviruses enter susceptible cells via receptor-mediated endocytosis and replicate in the cytoplasm of infected cells (id.). Following internalization, low endocytic pH induces a conformational change that exposes E1 fusion peptide and results in the release of the nucleocapsid (id.).

Since the genome of alphaviruses are capped at the 5' end and have a poly A tail at the 3' end, the viral RNA serves as mRNA for translation of nonstructural proteins (id.). The resulting polyprotein is sequentially cleaved into four proteins that are responsible for RNA replication, modification, and proteolytic cleavage (id.). Non-structural proteins facilitate the synthesis of negative and positive strands as well as the transcription of subgenomic mRNA encoding structural proteins (id.). Following translation, E1 and E2 are processed and glycosylated, and E1/E2 heterodimers are inserted into the host plasma membrane (id.). Capsid proteins interact with one genomic RNA copy to form the nucleocapsid, which interacts with the cytoplasmic tail of E2 protein to initiate virion budding from host cell membranes to commence another infectious cycle (id.).

Representative examples of alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69), Venezuelan equine encephalomyelitis virus (ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375), all of which are incorporated herein by reference.

I. EILAT VIRUS

Described herein is a new *alphavirus*, Eilat virus (EILV), isolated from a pool of *Anopheles coustani* mosquitoes collected in the Negev desert of Israel. Phylogenetic analyses places EILV as a sister to the Western Equine Encephalitis (WEE) antigenic complex within the main clade of mosquito-borne alphaviruses. Electron microscopy revealed that, like other alphaviruses, EILV virions are spherical, roughly 60-70 nm in diameter and bud from the plasma membrane of mosquito cells in culture. EILV readily infects a variety of insect cells with little overt cytopathology. However, in contrast to all other alphaviruses, EILV does not infect various mammalian and avian cell lines at 37° C. Evolutionarily, these findings indicate that EILV lost its ability to infect vertebrate cells. Thus, one use of EILV is in reverse genetic studies to assess the determinants of *alphavirus* host range. The EILV genome (SEQ ID NO:1) includes a 5' promoter, a non-structural protein (nsPs) coding segment (SEQ ID NO:2), an intergenic region containing a subgenomic promoter (SEQ ID NO:6), a structural protein (sPs) coding region (SEQ ID NO:4), 3' promoter, and a poly-A tail.

In one embodiment, the present invention provides an isolated nucleic acid comprising a coding segment having at least 80, 85, 90, 95, 98, 99, or 100% sequence identity to SEQ ID NO:1 or a fragment thereof. A "fragment" can be any 10, 20, 30, 40, 50, 100, 200, 300, 400, 500, 600, 700, 800, 1000, 2000, 3000, 4000, 5000, 6000, 7000, 8000, 9000, 10000, 11000 consecutive nucleotide segment thereof, including all values and ranges there between.

In some embodiments, the coding segment comprises a non-structural EILV coding region, e.g., SEQ ID NO:2, or a fragment thereof. In some embodiments, the coding segment encodes a non-structural EILV protein, or fragment thereof, e.g., nsP1, nsP2, nsP3, and/or nsP4. In one embodiment, all four of nsP1, nsP2, nsP3, and nsP4 are encoded.

In some embodiments, the coding segment comprises a structural EILV coding region, e.g., SEQ ID NO:4, or a fragment thereof. In some embodiments, the coding segment encodes a structural EILV protein or fragment thereof, e.g., C, E1, E2, E3, and/or 6K. In some embodiments, the coding segment encodes structural EILV protein C, E1, and/or E2.

In one embodiment, the present invention provides a chimera encoding at least one EILV protein or fragment thereof and a heterologous gene. In one embodiment, the chimera encodes at least one structural EILV protein; in another, it encodes at least one non-structural EILV protein. The heterologous gene can be, e.g., a therapeutic protein, an antigen, a toxin, or a marker. An antigen can be, e.g., a structural protein of another virus, e.g., a non-EILV *alphavirus*, e.g., VEEV, EEEV, or WEEV. In one embodiment, the heterologous gene encodes C, E1, and/or E2 of a non-EILV *alphavirus*. In one embodiment, the chimera encodes all three of C, E1, and E2 of a non-EILV *alphavirus*. Alternatively, the antigen can be a non-viral antigen. Such viral and non-viral antigens are useful in the manufacture of immunogenic compositions, and in methods for eliciting immune response in mammals including humans as discussed below.

In another embodiment, the heterologous gene is selected for selective expression in arthropods. Particular genes of interest include those that disrupt replication or hinder transmission of an arthropod-borne infectious disease and/or reduce the lifetime of the arthropod. Particularly useful hosts for such host-selective expression systems include mosquitoes (*Aedes* sp., *Culex* sp., *Anopheles* sp.). In one embodiment, the heterologous gene is expressed in *Aedes* sp., e.g., *Aedes albopictus* or *Aedes aegypti*.

In certain embodiments, the isolated nucleic acid is incorporated into an *alphavirus* vector capable of replicating in arthropods, e.g., *Aedes* sp., but not in mammals, e.g., humans.

II. PHARMACEUTICAL COMPOSITIONS

Certain embodiments are directed to pharmaceutical or immunogenic compositions comprising an *alphavirus* nucleic acid, *alphavirus* vector, *alphavirus* particle, *alphavirus* protein, or *alphavirus* virus, in combination with a pharmaceutically acceptable carrier, diluent, adjuvant, or recipient.

Briefly, the compositions described herein may be formulated in crude or purified forms. To produce virus in a crude form, virus-producing cells may first be cultivated in a bioreactor, wherein viral particles are released from the cells into the culture media. Virus may then be preserved in crude form by adding a formulation buffer to the culture media containing the virus to form an aqueous suspension. Within certain embodiments, the formulation buffer is an aqueous solution that contains one or more saccharide, high molecular weight structural additive, and buffering component in water. The aqueous solution may also contain one or more amino acids.

The virus or viral particle can be formulated in a purified form. More specifically, before adding the formulation buffer, the crude virus or viral particle described above may be clarified by passing it through a filter and then concentrated, e.g., by a cross flow concentrating system (Filtron Technology Corp., Nortborough, Mass.). DNase can be added to the concentrate to digest exogenous DNA. The digest is then filtered to remove excess media components and to establish the virus or viral particle in a more desirable buffered solution. The filtrate may then be passed over an affinity column, e.g., Sephadex® S-500 gel column, and a purified virus or viral particle is eluted. A sufficient amount of formulation buffer is then added to this eluate to reach a desired final concentration of the constituents and to minimally dilute the virus or viral particle. The aqueous suspension may then be stored, e.g., at −70° C., or immediately dried. The formulation buffer may be an aqueous solution that contains one or more saccharide, high molecular weight structural additive, and/or buffering component in water. The aqueous solution may also contain one or more amino acids.

Crude virus or viral particle may also be purified by ion exchange column chromatography. Briefly, crude virus or viral particles may be clarified by passing it through a filter, followed by loading the filtrate onto a column containing a highly sulfonated cellulose matrix. The virus or viral particle may then be eluted from the column in purified form by using a high salt buffer, and the high salt buffer exchanged for a more desirable buffer by passing the eluate over a molecular exclusion column. A sufficient amount of formulation buffer is then added to the purified virus or viral particle and the aqueous suspension is either dried immediately or stored, e.g., at −70° C.

The aqueous suspension in crude or purified form can be dried by lyophilization or evaporation at ambient temperature.

In certain aspects, the aqueous solutions used for formulation are composed of a saccharide, high molecular weight structural additive, a buffering component, and water. The solution may also include one or more amino acids. The components act to preserve the activity of the virus or viral particle upon freezing and lyophilization or drying through evaporation. A saccharide can be lactose, or other saccharides, such as sucrose, mannitol, glucose, trehalose, inositol, fructose, maltose, or galactose. In addition, combinations of saccharides can be used, for example, lactose and mannitol, or sucrose and mannitol.

The high molecular weight structural additive aids in preventing viral aggregation during freezing and provides structural support in the lyophilized or dried state. Within the context of the present invention, structural additives are considered to be of "high molecular weight" if they are greater than 5000 m·w. In certain aspects, a high molecular weight structural additive is human serum albumin. However, other substances may also be used, such as hydroxyethyl-cellulose, hydroxymethyl-cellulose, dextran, cellulose, gelatin, or polyvinylpyrrolidone.

The amino acids, if present, function to further preserve viral or viral particle integrity upon cooling and thawing of the aqueous suspension. A preferred amino acid is arginine, but other amino acids such as lysine, ornithine, serine, glycine, glutamine, asparagine, glutamic acid or aspartic acid can also be used.

The buffering component maintains a relatively constant pH. A variety of buffers may be used, depending on the pH range desired, preferably between 7.0 and 7.8. Suitable buffers include phosphate buffer, citrate buffer, and tromethamine.

In certain aspects, a viral or viral particle formulation can contain a neutral salt to adjust the final formulation to an appropriate iso-osmotic salt concentration. Suitable neutral salts include sodium chloride, potassium chloride or magnesium chloride.

The lyophilized or dehydrated viruses can be reconstituted using a variety of substances, such as water. In certain instances, dilute salt solutions that bring the final formulation to isotonicity may also be used.

III. ASSAYS USING CHIMERIC ALPHAVIRUSES

The methods described herein may comprise, for example, a method using chimeric Eilat *alphavirus* having an affinity and specificity for non-Eilat antibodies as a reagent. The methods may include, for example, radioimmunoassay, enzyme immunoassay such as ELISA or immunochromatography assay, coagulation assay (e.g., latex coagulation assay), and/or luminescence immunoassay (e.g., fluorescence immunoassay or chemiluminescence immunoassay). The methods are not limited to a particular assay method as long as a chimeric Eilat *alphavirus* described herein is used.

In certain aspects the method is an enzyme immunoassay such as ELISA or immunochromatography. Methods can be described by taking an ELISA or immunochromatography as an example; however, it is understood as a matter of course that the methods are not limited in any respect to the examples described. In particular, the chimeric Eilat *alphavirus* can be complexed with various antibodies in any desired order that results in the detection of antibodies that bind non-Eilat proteins or viruses. Thus, the methods described herein may include a variety of variants including, for example, direct methods, indirect methods, competitive methods, non-competitive methods, and sandwich methods. The methods may be carried out utilizing conventional detection and measurement principles well known in the art.

In one example, the methods may comprise a step of immobilizing an antibody (a capture antibody) that binds a chimeric Eilat *alphavirus* on a support, such as a 96-well plate, beads (e.g., polystyrene beads), a tube, or a membrane (e.g., nitrocellulose membrane) and incubating the captured chimeric Eilat *alphavirus* with a sample such as the blood or serum containing an antibody to be detected and/or measured. The chimeric Eilat *alphavirus*/target antibody complex is then incubated with a detection reagent, e.g., another reagent that specifically binds the target antibody (e.g., a secondary antibody) labeled with an enzyme and forming the enzyme-labeled antibody-chimeric *alphavirus* conjugate. The target antibody is detected using the detection reagent. These steps may be carried out by conventional procedures as are well known in the art, with the exception of the chimeric Eilat *alphavirus* used. For the other reagents to be used in these steps, conventional reagents may be used. In certain aspects the chimeric Eilat *alphavirus*/target antibody complex can be formed prior to capture of the complex on a support or detection medium.

One example of a representative enzyme immunoassay, ELISA will be briefly described below in generic terms. It should be understood, however, that the present invention is not intended to be limited to this example, and this is illustrated solely for the purpose of describing and example of the ELISA.

Enzyme-linked immunosorbent assays (ELISA) generally comprise binding a chimeric Eilat *alphavirus* with a target antibody to be measured in a sample; reacting the antibody bound by the chimeric Eilat *alphavirus* with a detection reagent directly or indirectly coupled to a label forming a detectable conjugate; detecting the conjugate, for example contacting the conjugate with a chromogenic substrate to convert the substrate into a pigment via the action of the enzyme; and detecting or measuring the label to identify the presence of a target antibody in a sample.

In certain aspects the chimeric Eilat *alphavirus* can be directly or indirectly coated or immobilized, for example, on the surfaces of the wells of a 96-well microplate as a support member in order to capture a target antibody. To the wells of the microplate, a sample or a standard solution containing the target antibody is then added to form a chimeric Eilat *alphavirus*/target antibody conjugate coated or immobilized on the wells of the microplate. In certain aspects the chimeric Eilat *alphavirus* can be added to the sample first forming the *alphavirus*/target antibody conjugate that is subsequently captured or detected.

Next, a detection reagent (e.g., a secondary antibody) labeled with a detectable label is added to the wells and reacted with the conjugate coated or immobilized thereon to form a detectable conjugate. The detection reagent may be chemically labeled with an enzyme to form a detection reagent that specifically binds the conjugate or the target antibody.

After the formation of a detectable conjugate or complex, a chromogenic substrate solution may be added to convert the chromogenic substrate into a pigment by means of the reaction with the enzyme of the enzyme-labeled secondary antibody. The enzyme reaction is then terminated with a quenching agent including an acid such as sulfuric acid. After the termination of the enzyme reaction, the target antibody complexed with the chimeric Eilat *alphavirus* is detected or measured by measuring the absorbance by means of measurement for the coloration of the pigment by the colorimetric method. The amount of target antibody in the sample may be computed from the absorbance. As described above, it is preferred to carry out the sandwich ELISA using a three-component sandwich system, that is, an antibody-antigen-antibody sandwich system.

In certain aspects an immunochromatographic assay can be used. A chromatographic support can be used in a kit and/or immunochromatography assay. An immunochromatographic support can comprise a sample pad disposed at one end of the support, a conjugate pad disposed under the sample pad to allow lateral flow of the sample from the sample pad to the conjugate pad. Underneath the conjugate pad, a migration zone is disposed extending in a downstream direction to an absorbent pad disposed at the other end of the support so as for the sample migrated from the conjugate pad to laterally flow in and through the migration membrane through a test line to a control line. Underneath the migration zone is a backing sheet supporting the support. The immunochromatographic support may be structured in such a manner that the sample introduced on the sample pad flows laterally and continuously by the capillary action of the structuring materials through the conjugate pad and the migration zone to the absorbent pad.

The sample pad can be made of a material having the physical property of lateral flow, that is, permeating the sample in and through the chromatographic support material by means of capillary action. The material to be used for the sample pad may include, for example, cellulose fibers, glass fibers, polyurethanes, polyacetates, acetate celluloses, and nylons.

The conjugate pad holds a detection reagent (e.g., a labeled chimeric Eilat *alphavirus* or antibody). The conjugate pad can be made of materials including, for example, cellulose fibers, glass fibers or non-woven cloth. The conjugate pad may be prepared by introducing or impregnating a given amount of the detection reagent (e.g., a labeled chimeric Eilat *alphavirus* or antibody) into the conjugate pad and drying the material. At the conjugate pad, the target antibody contained in the sample migrates from the sample pad and forms a conjugate with the detection reagent on or in the conjugate pad, followed by capturing and recognizing the target antibody in the form of a labeled antibody-antigen complex.

The detection reagent for the conjugate pad may be prepared by coating or labeling a chimeric Eilat *alphavirus* with a label, e.g., colloidal metal particles. Average particle sizes of such colloidal metal particles may be in the range from approximately 1 to 500 nm, preferably from approximately 1 to 50 nm. The labeling reaction may be performed in accordance with conventional procedures well known in the art.

The migration zone is a chromatographic carrier and may be in the form of a sheet and can be made of a porous material include, but are not limited to nitrocellulose membrane, cellulose membrane, nylon membrane, glass fibers, or non-woven cloth. The materials will allow the migration of the sample in and through the membrane by capillary action. The migration zone can be configured to allow the sample in the conjugate pad to lateral flow through the membrane toward the adsorbent pad.

The migration zone can be configured to have a test line positioned between the conjugate pad and the adsorbent pad. The test line works as a zone for deciding the presence (positive) or absence (negative) of a target antibody in a sample. The test line may contain a immobilizing reagent that binds chimeric Eilat *alphavirus*/target antibody complex. If the labeled chimeric Eilat *alphavirus* is provided in the conjugate pad then the immobilizing reagent can comprise a reagent having an affinity for the target antibody. In certain aspects, an Eilat specific antibody or an antibody that binds the constant region of a target antibody is immobilized on the membrane.

At the test line of the migration zone, the immobilized complex forms a detectable signal or composition. In certain aspects the immobilized complex is visualized by using particles as a label. By using the colloidal metal particles or other substances as the label the presence or absence of the target antibody in the sample is visualized, resulting in realizing precise and simple measurement and an extremely useful tool for point of care detection or measurement. The migration zone may also contain a control line downstream the test line. The control line will comprise an immobilizing agent specific for the detectably labeled reagent allowing the labeled reagent to be captured and visualized in the absence of a target antibody.

In one aspects the immunochromatography assay comprises the steps of introducing a sample containing an antibody to be measured onto a sample inlet. The sample migrates to the conjugate pad where the sample containing the target antibody flows laterally through the conjugate pad and through the migration zone. When entering the conjugate pad any target antibody present in the sample is conjugated to a detection reagent forming a labeled antibody complex. The labeled antibody complex migrates through the conjugate pad, to and through the migration zone. During migration through the migration zone the complex is brought into contact with the test line. In the test line, the labeled antibody complex is then conjugated with an immobilizing reagent of the test line, forming a three-component conjugate, which is in turn visualized using the label. If a target antibody is in the sample, the test line is visualized and determined to be positive. If the sample does not contain detectable levels of the target antibody the assay would be negative and only the control line is visualized.

The chimeric alphaviruses described herein can be used to prepare various compositions or kits for performing the assays described above and detecting or diagnosing infection or a pathologic condition. For the preparation of compositions or kits for diagnosing *alphavirus* infection, the chimeric *alphavirus* can be coupled to a substrate. In addition, enzyme-linked immunosorbent assay (ELISA) diagnostic kits comprising the chimeric *alphavirus* can be used to test samples, and rapid immunochromatographic diagnostic kits can also be prepared for simple and easy tests.

Certain embodiments are directed to assays for detection of *alphavirus* infection. Chimeras containing EILV replicative machinery (i.e. non-structural proteins, 5' and 3' UTRs) and structural proteins of a non-EILV *alphavirus* are used as a capture agent for detecting non-EILV *alphavirus* antibodies in a sample. Supernatants or concentrated EILV chimeras generated in mosquito cells can be utilized as antigens or reagents in a variety of immunoassay formats, inlcuding ELISAs. The kits using chimeric virus described herein can be used to detect target antibodies such as anti-virus antibodies with minimal cross reactivity. In certain aspects the chimeric Eilat *alphavirus* can be inactivated using irradiation or other means of virus inactivation known in the art.

A sample can be assayed for *alphavirus* by an antigen-antibody reaction in a conventional immunoassay method. Examples of the immunoassay methods include radioimmunoassay (RIA), enzyme immunoassay (EIA), enzyme-linked immunosorbent assay (ELISA), fluorescence immunoassay (FIA), fluorescence polarization, and immunochromatography.

The capture agent used in one aspect is a chimeric *alphavirus* that binds specifically to non-Eilat *alphavirus* antibodies in a sample. Depending on the method, the capture agent may be labeled with a labeling substance or may be immobilized on a solid phase. In another aspect a secondary antibody may be labeled and used as a detection reagent.

The label or detection moiety is selected depending on the measurement method. For example, when the measurement method is radioimmunoassay (RIA), the labeling substance used is a radioisotope such as $^{125}I$, $^{14}C$ or $^{32}P$. The label used in enzyme immunoassay (EIA) or enzyme-linked immunosorbent assay (ELISA) may be an enzyme such as β-galactosidase, peroxidase, alkali phosphatase, or the like. The label used in fluorescent immunoassay (FIA) or fluorescence polarization is a fluorescent dye such as a fluorescein derivative or a rhodamine derivative. In immunochromatography, an insoluble granular marker or the like can be used. The various particles can be used for labeling, and particles may include, but are not limited to latex coloring particles of organic polymers such as polystyrenes, styrenes, or styrene-butadiene copolymers, or metal particles such as metal colloids, e.g., gold colloid or silver colloid, or metal sulfides.

The substrate or solid phase for immobilizing the capture agent is appropriately selected depending on the measurement method. The material of the substrate or solid phase is not particularly limited insofar as it has an affinity for the capture agent. Examples of a substrate or solid phase include synthetic organic polymer compounds such as polyvinyl chloride, polyvinylidene fluoride (PVDF), polystyrene, a styrene-divinyl benzene copolymer, a styrene-maleic anhydride copolymer, nylon, polyvinyl alcohol, polyacrylamide, polyacrylonitrile and polypropylene, polysaccharides such as a dextran derivative, agarose gel and cellulose, and inorganic polymer compounds such as glass, silica gel and silicone. These materials maybe those into which functional groups such as an amino group, an aminoacyl group, a carboxyl group, an acyl group, a hydroxyl group and a nitro group have been introduced. The shape of the substrate or solid phase is also appropriately selected depending on the measurement method. For example, the solid phase may be placoid (e.g., a microtiter plate (ELISA plate) and a disk), particulate (e.g., beads), tubular (e.g., a test tube and a tube), fibrous and membranous. The method of immobilizing the capture agent on the solid phase may be a method known in the art, such as a physical adsorption method, an ionic bonding method, a covalent bonding method or an inclusion method.

In addition to the capture agent, a kit can contains first and second antibodies that bind specifically to target. A kit can comprises a number of capture agent specific for a particular target.

The kit described herein is used to measure *alphavirus* antibodies in a specimen by the methods described above. In certain aspects the assay methods is an enzyme immunoassay method. In a further aspect the assay method is an enzyme immunoassay method using a chemiluminescence substrate.

At least one antibody contained in the kit is an antibody that binds specifically to an antibody produced by the subject from which the sample is obtained.

The kit may further contain a substrate or solid phase for immobilizing the capture agent. This substrate or solid phase may be the same as described above. When the substrate or solid phase is contained in the kit, the substrate or solid phase may be supplied with the capture agent coupled to the substrate or solid phase, or the capture agent can be supplied in a separate container.

In addition to those components mentioned above, the kit may further contain, for example, a wash for washing wells of a microplate, a substrate for an enzyme labeling antibodies, and the like. The wash includes a buffer solution containing a salt at a predetermined concentration.

In certain aspects a capture agent is contacted with a sample forming a complex between the capture agent and any target present in the sample. The capture agent/target complex may then be directly detected or contacted with a detection reagent. In certain aspects the detection reagent is an antibody that specifically binds antibodies produced by the subject from which the sample has been obtained. The complex between the capture reagent/target/detection reagent can then be detected or measured. When a substrate or solid phase for immobilizing the capture agent, the capture agent in the complex formed in the complex-forming step has been immobilized on a substrate or solid phase. A detection reagent (e.g., antibody) in the complex is labeled. Accordingly, the complex can be detected by detecting the label of the detection reagent in the detection step.

Examples of a substrate or solid phase include a microtiter plate, a plastic tube, glass beads, etc. The label may be bound directly or indirectly to the detection reagent. For example, the detection reagent is labeled with biotin, then, avidin that binds specifically to biotin is coupled with a label, the detection reagent can be label via a biotin-avidin bonding.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Eliat Virus, a Newly Identified Host Restricted *Alphavirus*

A. Results

Virus Isolation.

EILV was one of 91 viruses collected during a survey of the Negev desert in Israel between 1982-84 (Muriu et al., *Malar J.* 2008, 7:43). Mosquitoes were collected from many parts of the desert including in the city of Eilat and the isolation was from a pool of *Anopheles coustani* (Fornadel et al., *Vector Borne Zoonotic Dis.* 2011, 11(8):1173-9). Preliminary characterization showed that the virus was unable to grow in mammalian cells but could grow to high titers in insect cells.

Genomic Analysis.

The sequence of EILV was determined by 454 Sequencing™. EILV genomic sequence was translated and compared with Sindbis virus to determine the length of each gene product. A schematic of EILV genome is shown in FIG. 1. The length of untranslated regions (UTRs), intergenic region, and each gene product is similar to that of other alphaviruses. The coding region nucleotides and deduced amino acids of EILV were compared with other members within the genus. The nucleotide and amino acid identity of EILV with other members ranged from 57%-43% and 58% to 28%, respectively (Table 1).

Comparison of nucleotide and amino acid identity of structural and nonstructural coding regions of alphaviruses. Upper diagonal displays percent amino acid identity; lower diagonal contains percent nucleotide identity.

|       | EV | TROV | AURAV | WHATV | SINV | WEEV | EEEV | VEEV | CHIKV |
|-------|----|------|-------|-------|------|------|------|------|-------|
| EV    |    | 52   | 43    | 58    | 44   | 37   | 36   | 37   | 49    |
| TROV  | 53 |      | 43    | 57    | 43   | 38   | 38   | 39   | 51    |
| AURAV | 55 | 57   |       | 47    | 65   | 38   | 39   | 51   | 41    |
| WHATV | 57 | 56   | 61    |       | 55   | 39   | 39   | 39   | 53    |
| SINV  | 56 | 57   | 61    | 70    |      | 39   | 39   | 52   | 40    |
| WEEV  | 52 | 54   | 55    | 58    | 57   |      | 70   | 46   | 40    |
| EEEV  | 51 | 53   | 53    | 54    | 54   | 64   |      | 47   | 41    |
| VEEV  | 51 | 54   | 54    | 55    | 54   | 58   | 60   |      | 41    |
| CHIKV | 52 | 53   | 53    | 55    | 54   | 53   | 54   | 54   |       |
| RRV   | 51 | 53   | 54    | 55    | 55   | 55   | 55   | 54   | 62    |
| UNAV  | 52 | 54   | 54    | 54    | 55   | 53   | 54   | 53   | 62    |
| SFV   | 53 | 53   | 54    | 55    | 55   | 54   | 55   | 54   | 62    |
| MIDV  | 52 | 53   | 54    | 55    | 54   | 53   | 54   | 54   | 60    |
| BFV   | 52 | 52   | 53    | 54    | 53   | 53   | 54   | 53   | 56    |
| NDUV  | 51 | 52   | 53    | 54    | 53   | 53   | 53   | 53   | 58    |
| SESV  | 50 | 51   | 52    | 52    | 51   | 52   | 52   | 52   | 54    |
| SPDV  | 43 | 44   | 44    | 44    | 45   | 44   | 45   | 45   | 45    |

|       | RRV | UNAV | SFV | MIDV | BFV | NDUV | SESV | SPDV |
|-------|-----|------|-----|------|-----|------|------|------|
| EV    | 48  | 39   | 28  | 39   | 38  | 49   | 47   | 28   |
| TROV  | 52  | 39   | 28  | 39   | 38  | 51   | 47   | 29   |
| AURAV | 41  | 41   | 30  | 40   | 39  | 41   | 37   | 21   |
| WHATV | 54  | 41   | 31  | 41   | 40  | 53   | 49   | 30   |
| SINV  | 41  | 41   | 31  | 41   | 39  | 41   | 37   | 22   |
| WEEV  | 40  | 40   | 30  | 40   | 39  | 40   | 38   | 21   |
| EEEV  | 41  | 40   | 30  | 40   | 40  | 40   | 38   | 21   |
| VEEV  | 40  | 40   | 30  | 40   | 39  | 40   | 38   | 22   |
| CHIKV | 66  | 48   | 36  | 46   | 42  | 58   | 53   | 30   |
| RRV   |     | 49   | 38  | 47   | 42  | 60   | 53   | 30   |
| UNAV  | 64  |      | 59  | 46   | 42  | 44   | 39   | 22   |
| SFV   | 65  | 66   |     | 36   | 33  | 33   | 29   | 29   |
| MIDV  | 62  | 61   | 63  |      | 59  | 44   | 39   | 22   |
| BFV   | 57  | 56   | 58  | 58   |     | 42   | 39   | 22   |
| NDUV  | 58  | 57   | 59  | 59   | 57  |      | 53   | 29   |
| SESV  | 54  | 54   | 54  | 54   | 54  | 54   |      | 29   |
| SPDV  | 46  | 45   | 46  | 45   | 45  | 43   | 43   |      |

In both analyses, EILV had the highest identity to Whataroa virus (WHATV) and lowest identity to SPDV. Amino acid comparison of individual protein was also performed (Table 2). EILV polymerase, nsP4, displayed the highest amino acid identity with other alphaviruses, whereas nsP3 had the least. Overall, EILV proteins shared greater identity with Aura (AURAV), WHATV and SINV than other members. The putative cleavage sites for the polyproteins were also compared (FIG. 2B). The nsP4 cleavage site was the most conserved within the genus even amongst the distantly related aquatic alphaviruses, SESV and SPDV. The cleavage sites of EILV non-structural and structural proteins had a greater identity with Trocara (TROV), AURAV, WHATV and SINV.

TABLE 2

Comparison of individual EILV proteins within the genus *Alphavirus*. Percent amino acid identities are shown.

| Virus | nsP1 | nsP2 | nsP3 | nsP4 | capsid | E3 | E2 | 6k | E1 |
|---|---|---|---|---|---|---|---|---|---|
| Trocara | 64 | 58 | 30 | 72 | 49 | 41 | 34 | 41 | 46 |
| Aura | 73 | 60 | 36 | 74 | 53 | 46 | 36 | 36 | 47 |
| Whataroa | 72 | 65 | 36 | 74 | 50 | 42 | 43 | 40 | 49 |
| Sindbis | 71 | 65 | 34 | 77 | 53 | 45 | 40 | 45 | 50 |
| WEE | 57 | 49 | 29 | 68 | 43 | 44 | 42 | 38 | 49 |
| EEE | 56 | 50 | 29 | 69 | 43 | 42 | 36 | 40 | 47 |
| VEE | 56 | 51 | 29 | 68 | 40 | 47 | 34 | 39 | 45 |
| Chikungunya | 56 | 53 | 34 | 69 | 44 | 43 | 36 | 44 | 42 |
| Ross River | 60 | 52 | 30 | 69 | 41 | 45 | 35 | 25 | 42 |
| *Una* | 58 | 53 | 32 | 71 | 42 | 45 | 36 | 28 | 43 |
| Semliki Forest | 58 | 53 | 36 | 69 | 42 | 53 | 35 | 28 | 43 |
| Middelburg | 59 | 53 | 37 | 70 | 42 | 46 | 37 | 32 | 42 |
| Barmah Forest | 58 | 52 | 35 | 70 | 45 | 42 | 32 | 34 | 42 |
| Ndumu | 60 | 52 | 32 | 70 | 42 | 50 | 33 | 18 | 42 |
| SES | 53 | 51 | 28 | 65 | 44 | 47 | 30 | 42 | 42 |
| SPD | 41 | 38 | 21 | 52 | 31 | 25 | 24 | 26 | 36 |

Figure 3C:
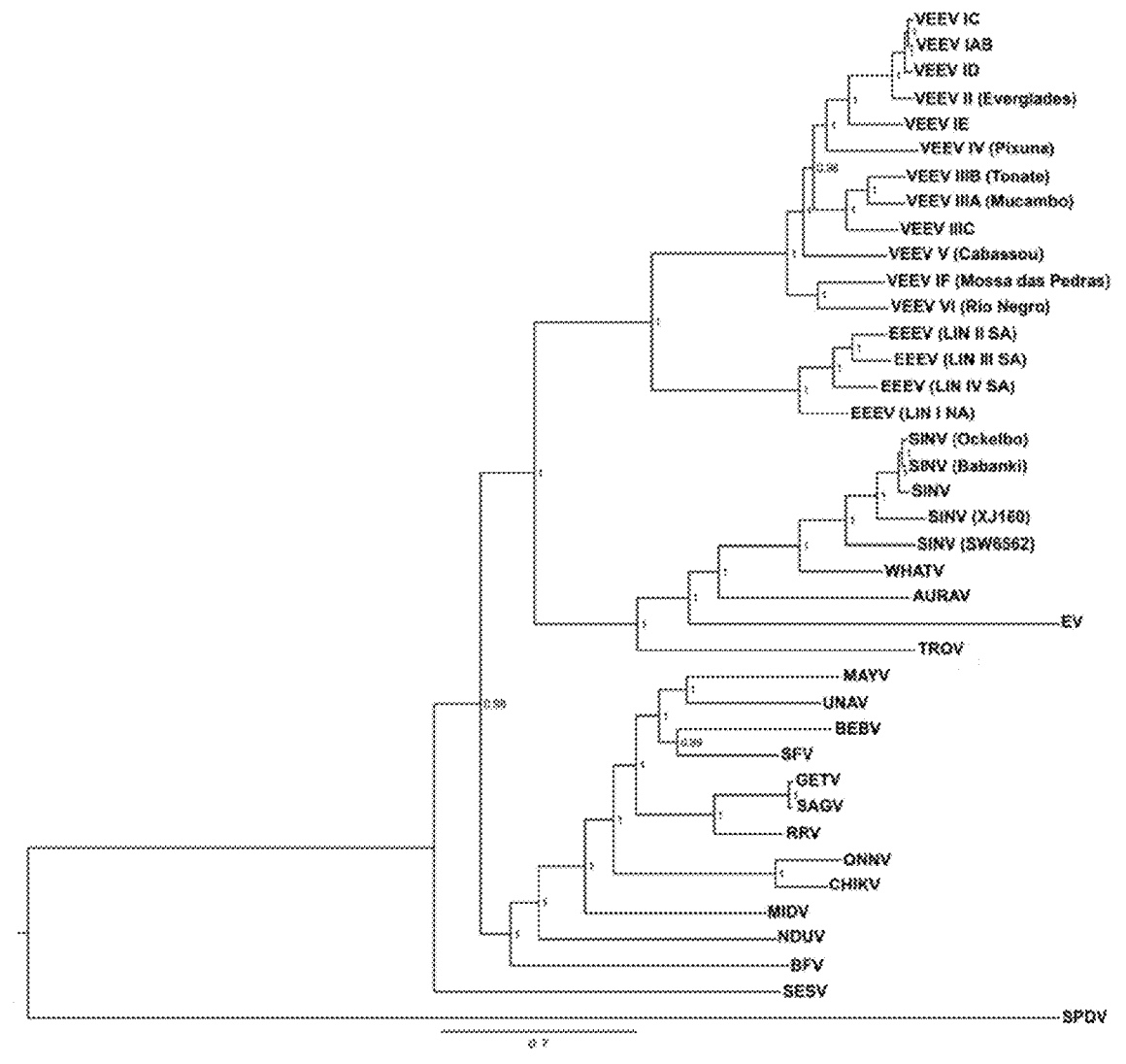

The four conserved sequence elements (CSE) were also compared. First CSE is located in the 5' UTR that serves as a core promoter for RNA synthesis and is structurally conserved. Utilizing mFold EILV 5'UTR could form hairpin structures similar to that of SINV (data not shown). The second CSE is a 51 nt sequence within nsP1 gene which likely functions as a replication enhancer. EILV nsP1 CSE shared identity with AURAV, WHATV and SINV (FIG. 2). Similar to 5' CSE, EILV nsP1 CSE was able to form similar hairpin structures as SINV (data not shown). The third CSE is the 24-nt subgenomic promoter that serves as the promoter for transcription of the subgenomic RNA. EILV subgenomic CSE shared significant identity with WEEV and EEEV (FIG. 3A). Lastly, the 3' CSE is a 19-nt element located immediately before the poly-A tail, which serves as the promoter for negative strand synthesis. EILV 3' CSE was almost identical to AURAV, EEEV, VEEV and SFV (FIG. 3B).

Lastly, the putative E1 fusion peptide and ribosomal binding site in capsid of EILV were also compared. EILV E1 fusion peptide was identical to WHATV and shared significant identity with SINV, WEEV, EEEV, VEEV and CHIKV (FIG. 4). Whereas the ribosomal binding site showed greater sequence divergence, with greater identity with AURAV and SINV (FIG. 4). Many of the amino acid differences in the EILV ribosomal binding site were present in other viruses.

Phylogenetic Analysis.

Figure 5A:
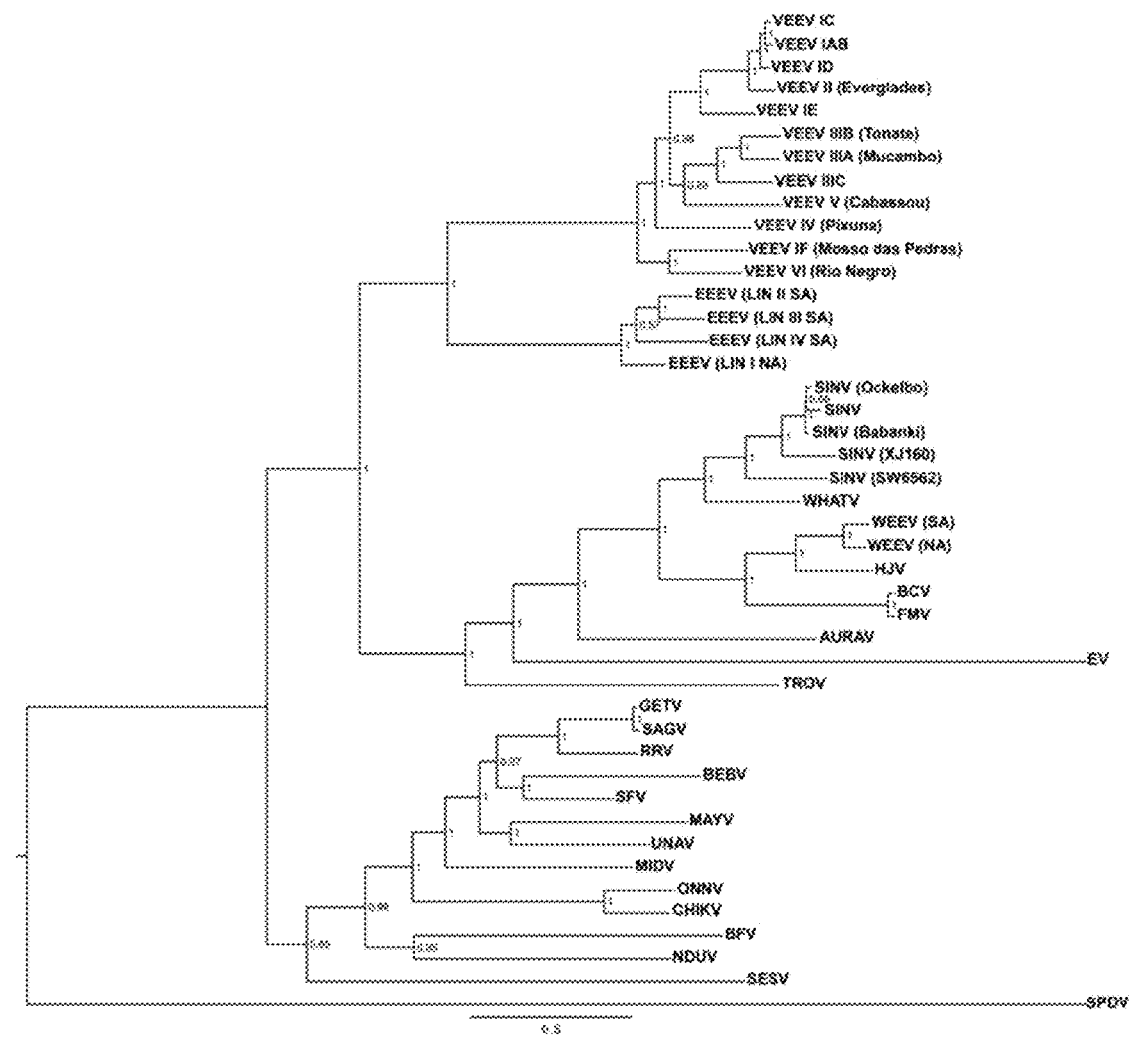
Figure 5B:
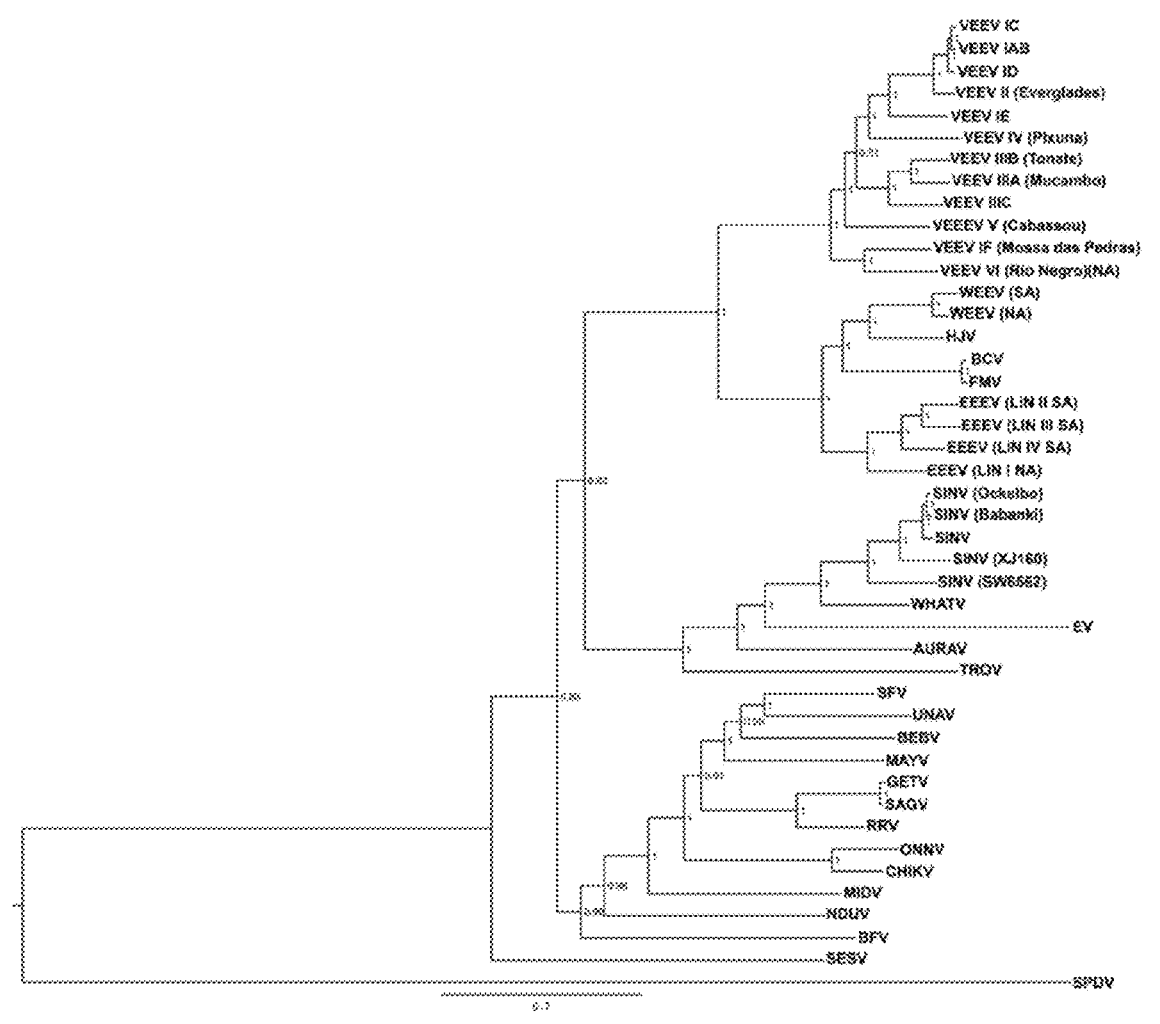

Neighbor joining, maximum likelihood and Bayesian methods were utilized to determine the relationship of EILV within the *alphavirus* genus. Trees were generated using full-length, non-structural and structural nucleotide alignments. The full-length and structural nucleotide analysis utilizing all three methods placed EILV sister to the WEE complex (FIG. 5A, FIG. 3C, and data not shown) with high posterior and bootstrap support. The analysis of the non-structural alignment showed some inconsistency. The neighbor joining method placed EILV sister to WEE complex where as Bayesian and maximum likelihood analyses placed EILV within the WEE complex basal to WHATV (FIG. 5B, and data not shown).

Serological Analysis.

Both complement fixation (CF) and hemagglutination inhibition (HI) tests were also performed to determine the antigenic relationship of EILV with the genus. In CF test, EILV antigen did not cross react with sera against most members and had minimal cross reactivity with TROV, AURAV, SINV, EEEV, and VEEV (FIG. 6A). In HI test, EILV anti-sera minimally cross-reacted with TROV, SINV, WEEV, and EEEV (FIG. 6B). Purified EILV did not hemagglutinate and EILV anti-sera yielded high background with homologous antigen therefore these data were removed from the analysis.

Rescue of Infectious EILV Clone, In Vitro Characterization and TEM.

EILV cDNA clone was constructed utilizing standard molecular techniques.

Figure 7A:
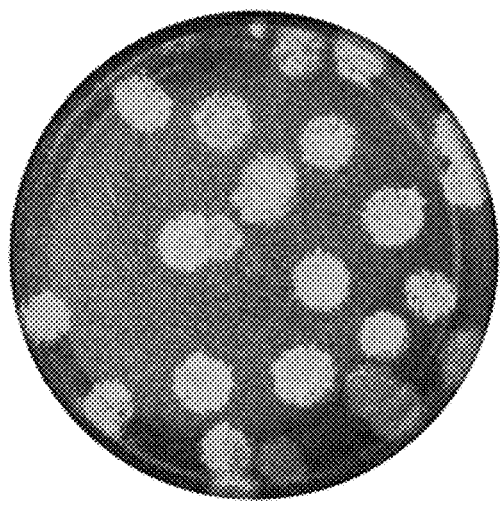
Figure 7B:
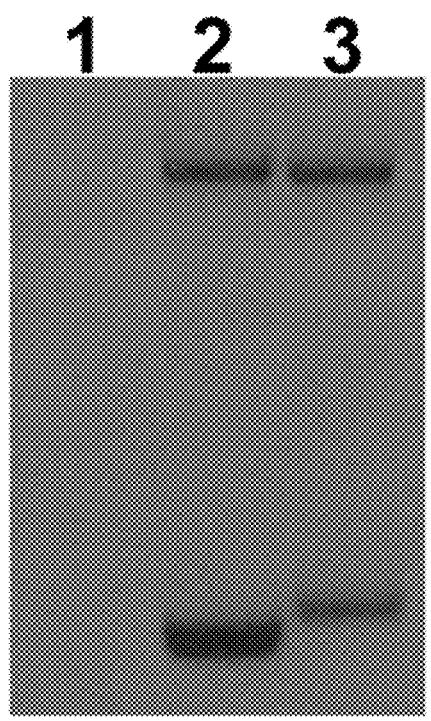
Figures 8A, 8B:
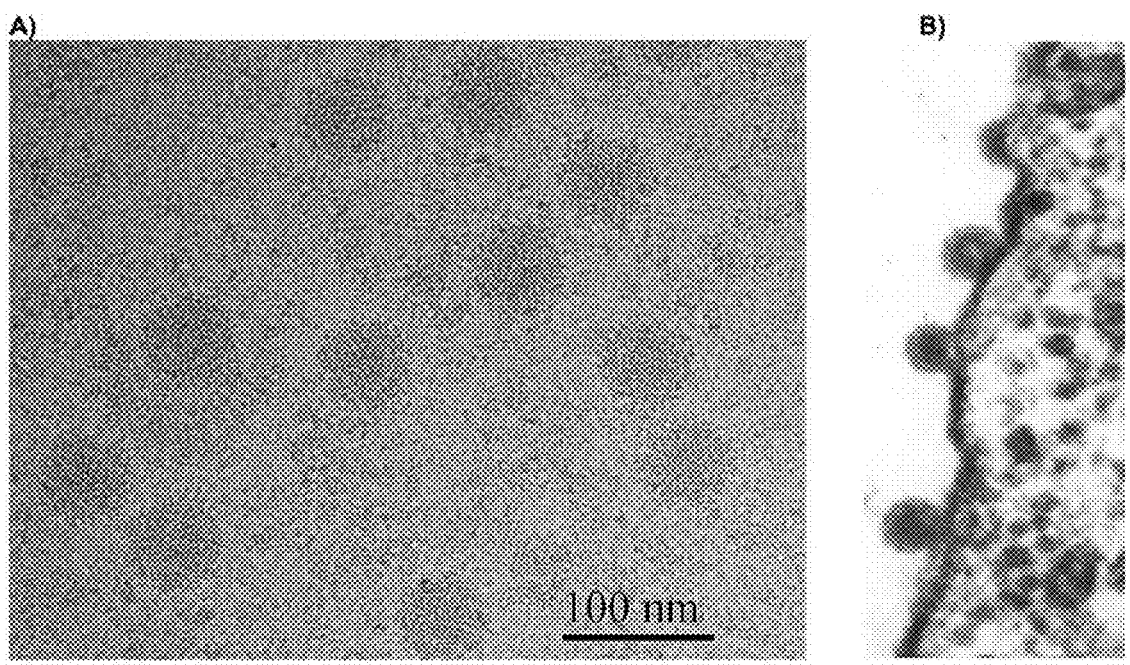
Figures 9A, 9B:
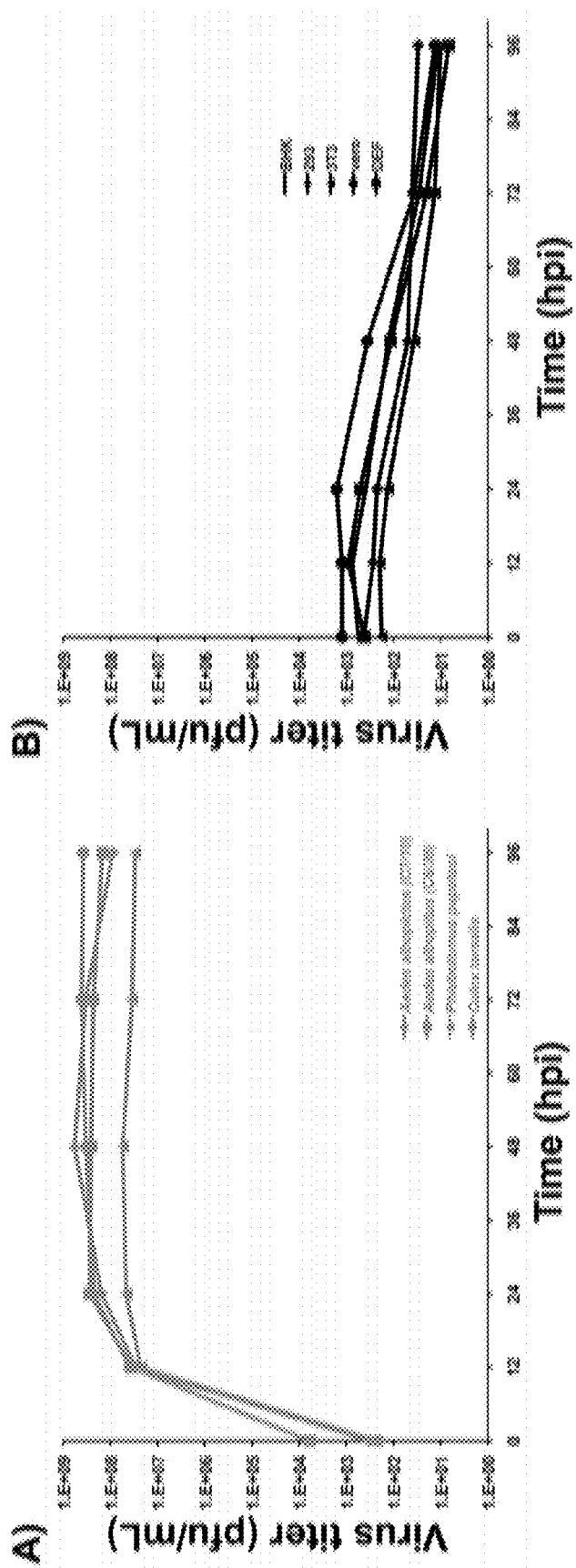
Figures 10A, 10B, 10C:
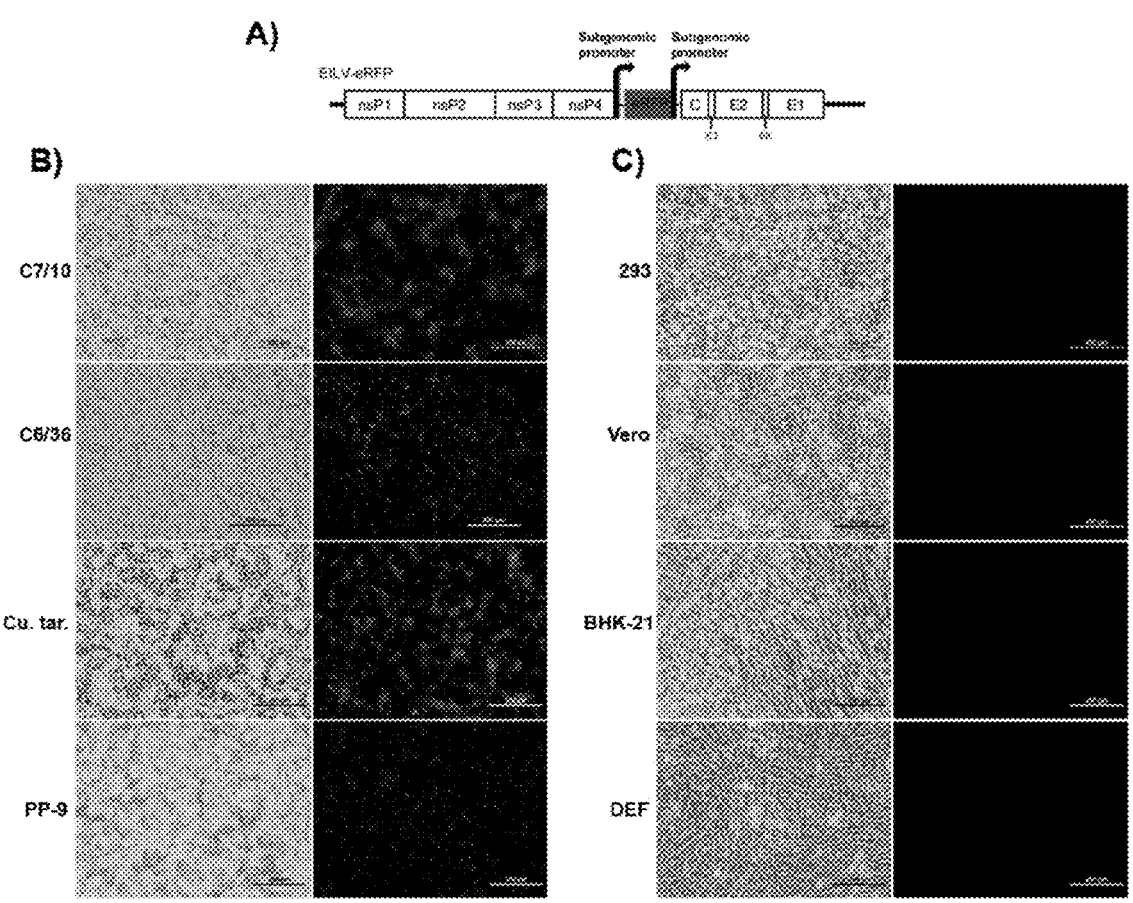

Virus did not cause any overt cytopathology on C7/10, however at lower cell density EILV infected cells grew at a slower rate (data not shown). EILV formed 3-4 mm plaques 3 days post infection on C7/10 cells (FIG. 7A). RNA analysis of EILV infected C7/10 demonstrated that EILV could produce similar RNA species as SINV, indicating the synthesis of genomic RNA as well as expression of subgenomic RNA (FIG. 7B). TEM analysis of EILV virions showed that the virions are spherical in shape, roughly 60-70 nm in diameter and bud from the plasma membrane (FIGS. 8A-8B).

In Vitro Host Range.

Figures 11A, 11B:
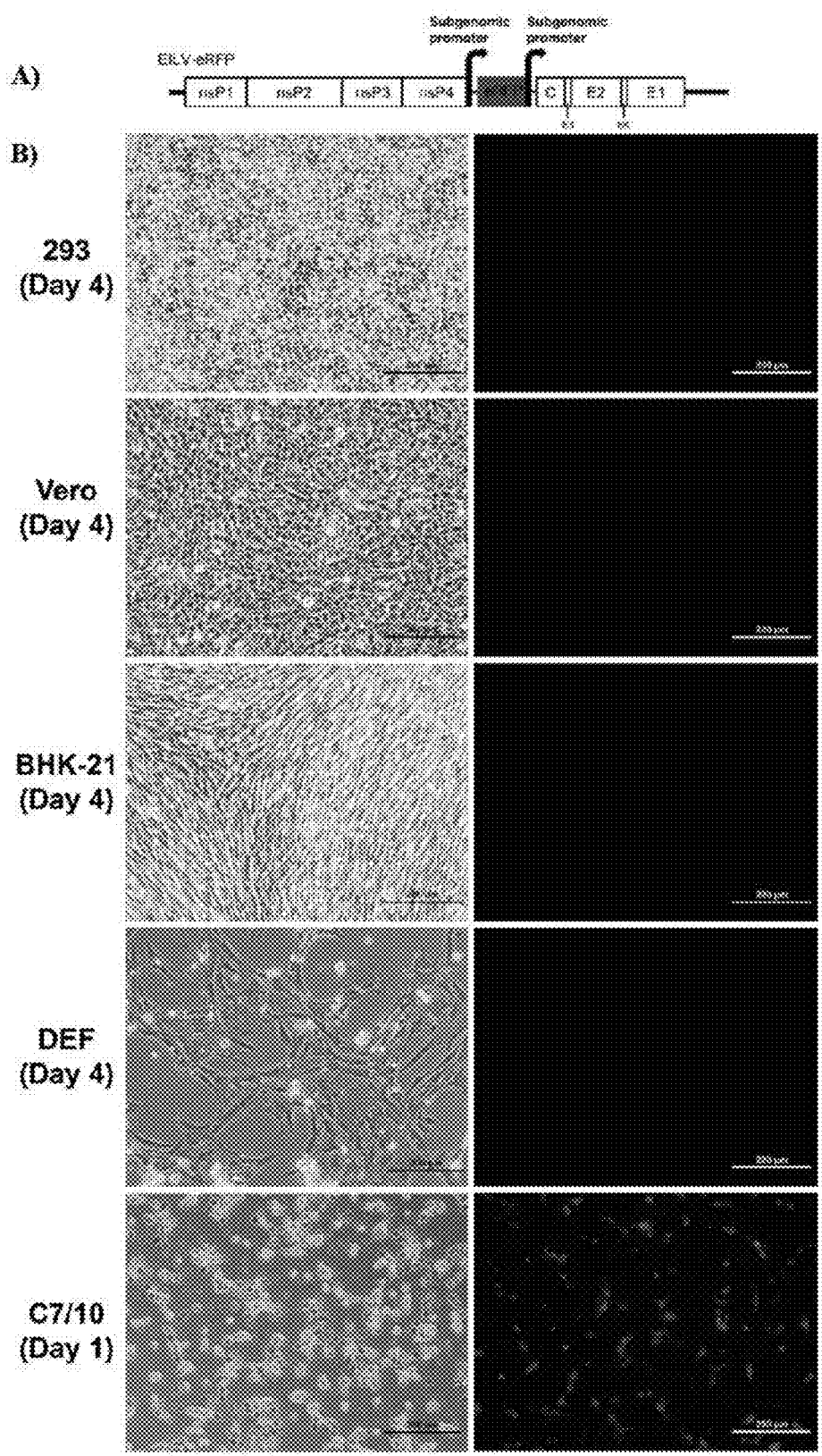

Representative vertebrate (Vero, BHK-21, 293, NIH 3T3, and DEF) and invertebrate (C6/36, C7/10, *Cu. tarsalis*, and *P. papatasi*) cell lines were used to determine the in vitro host range of EILV. SINV was used as a positive control as it has been shown to have a broad in vitro host range (Way et al., *J Gen Virol.* 1976, 30(1):123-30; Sarver and Stollar, *Virology.* 1977, 80(2):390-400; Igarashi, *J Gen Virol.* 1978, 40(3):531-44).

Both SINV and EILV were able to infect *Cu. tarsalis, P. papatasi*, C6/36, and C7/10 cells (FIG. 9A and data not shown). EILV grew rapidly to high titers (>$10^7$ pfu/mL) 12-hrs-post infection (hpi) with peak titer ranging from $5\times10^7$ to $5\times10^8$ pfu/mL at 48-hpi. Although both SINV and EILV were able to infect all four invertebrate cell lines, the infection did not yield any overt cytopathology (data not shown). All vertebrate cell lines were readily infected by SINV and showed extensive cytopathology at 12-hpi (data not shown). Whereas EILV was unable to infect any of the vertebrate cell lines tested and no overt cytopathology was observed (FIG. 9B and data not shown). The initial EILV inoculum decayed significantly by 72-hpi and was barely above the limit of detection at 96-hpi. These results were also confirmed by infection with EILV-eRFP at MOI of 10 (FIG. 10). EILV infected invertebrate cells expressed eRFP 24-hrs-post-infection, whereas no fluorescent signal was observed in any vertebrate cell lines up to 4-days-post-infection (FIGS. 10B-10C).

Analysis of EILV RNA Replication in Vertebrate Cells.

To ascertain whether the host range restriction was present at the RNA levels, EILV-eRFP clone was in vitro transcribed and electroporated into vertebrate and invertebrate cells. EILV-eRFP was unable to replicate in vertebrate cells up to 4 days-post-electroporation, whereas it readily replicated in invertebrate cells (FIGS. 11A-11B). This indicates that the EILV RNA itself in incapable of replication in vertebrate cells.

Chimeric Virus Host Range.

Figures 12A, 12B:
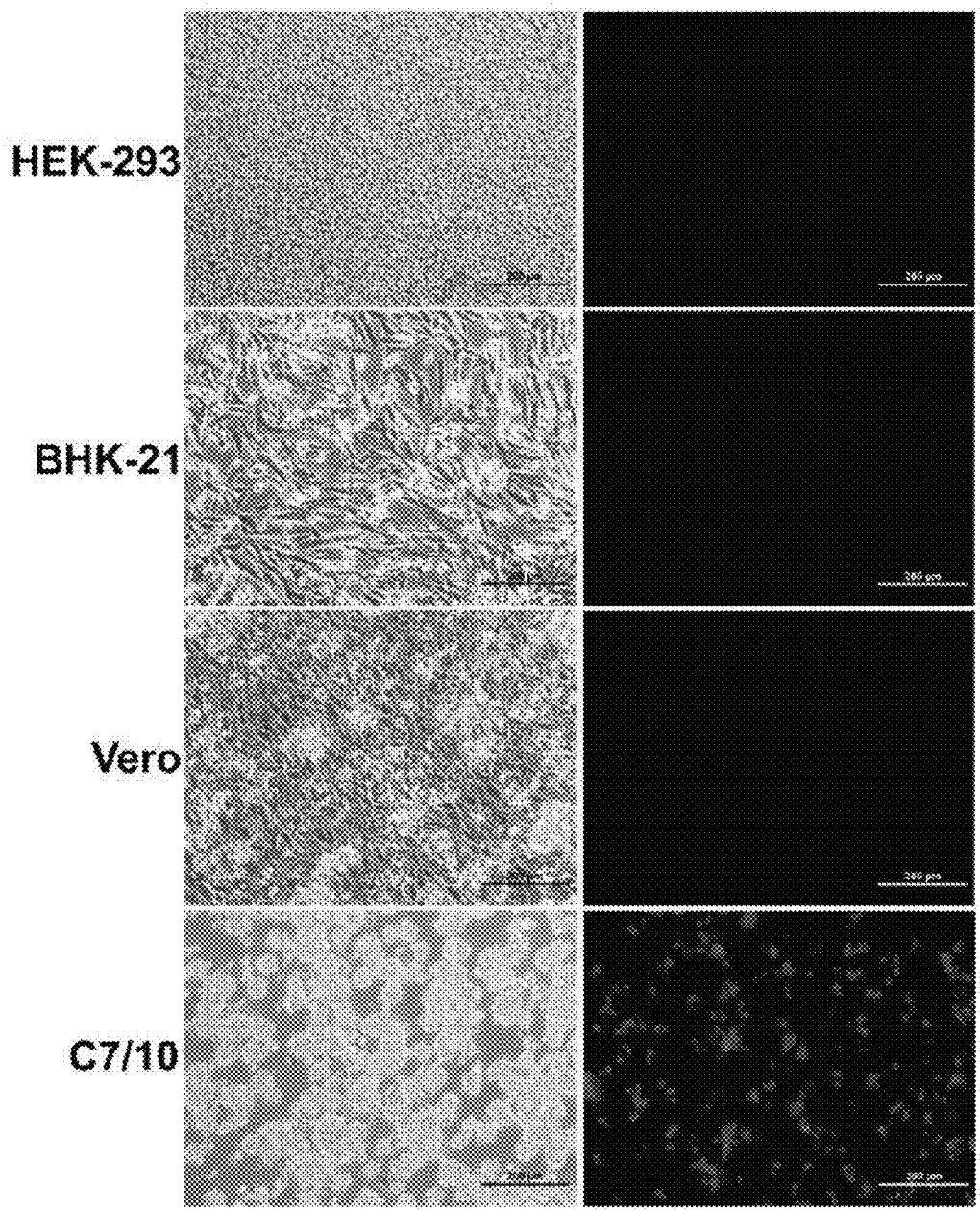
Figures 13A, 13B:
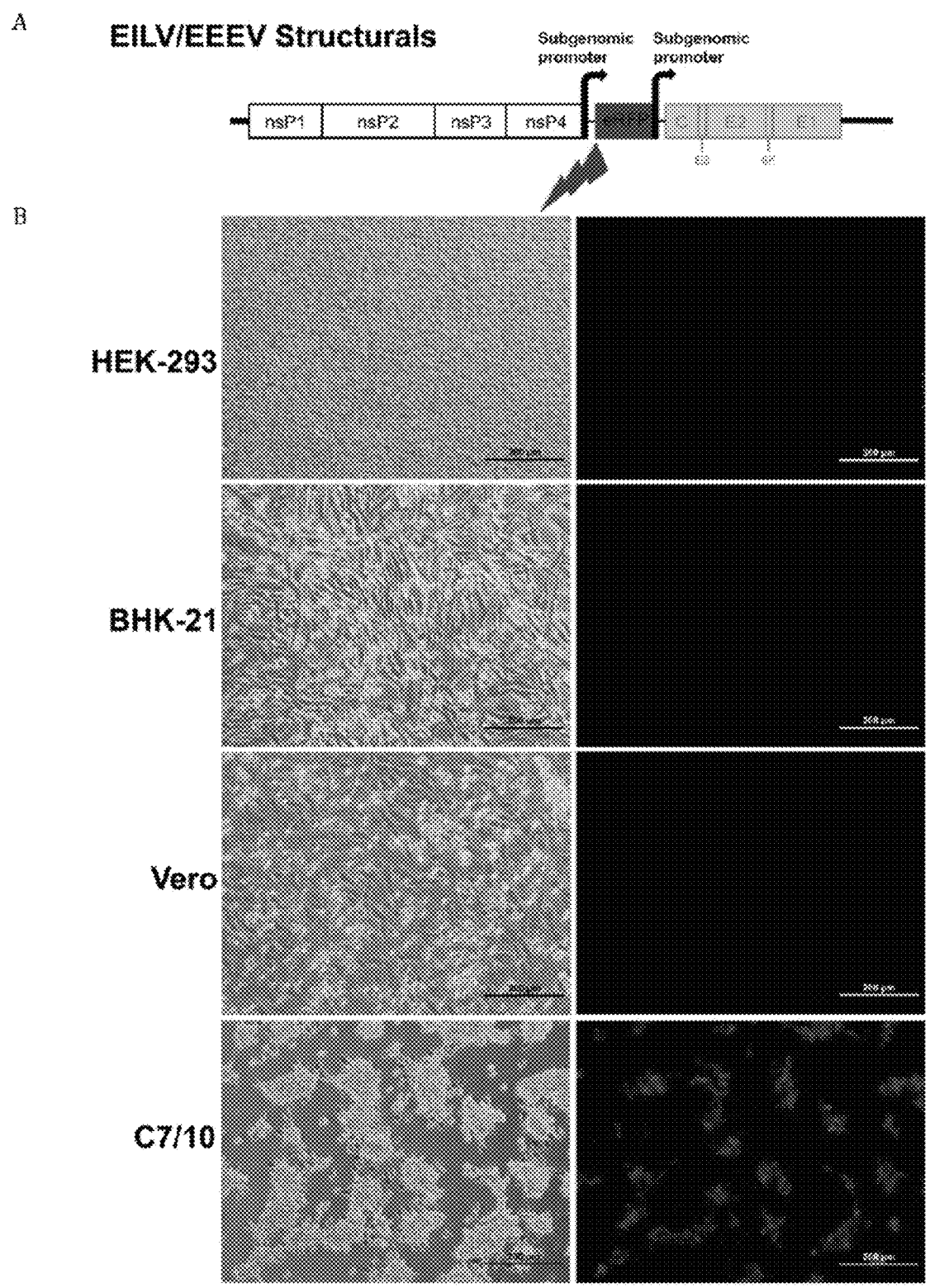
FIGS. 13A-13B. Illustrates the infectivity of EILV/EEEV structural construct across various host cells. (A) Diagram of an EILV/EEEV marker construct. (B) Results of infection of cell lines with a virus comprising the EILV marker genome, light and fluorescent image.

Representative vertebrate and invertebrate cell lines were used to determine the in vitro host range of EILV/SIN and EILV/EEEV chimeras (FIG. 12 and FIG. 13). The chimeras were EILV backbones having the structural proteins substituted with sindbis virus (SIN) or eastern equine encephalitis virus (EEEV) structural protein genes. The chimeric virus maintained the EILV host range, i.e., arthropod specific replication.

B. Materials and Methods:

Viruses and cells. Eilat and Sindbis (Eg 339) viruses were obtained from Arbovirus Reference Center at the University of Texas Medical Branch. Both viruses were amplified on C7/10 cells and stored at −80° C.

Vero, baby hamster kidney (BHK-21), human embryonic kidney (HEK-293), Duck embryo fibroblast (DEF), mouse fibroblast (NIH 3T3), and *Aedes albopictus* (C6/36 and C7/10) cell lines were obtained from the American Type Culture Collection. *Culex tarsalis* and *Phlebotomus papatasi* cells were obtained from the Arbovirus Reference Center at the University of Texas Medical Branch. Cell lines were propagated under conditions of 37° C. or 28° C. and 5% $CO_2$ in Dulbecco's modified Eagle's medium containing 10% fetal bovine serum, sodium pyruvate (1 mM), and Penicillin (100 units/mL)-Streptomycin (100 μg/ml). C6/36, C7/10 and *Culex tarsalis* media was additionally supplemented with 1% tryptose phosphate broth solution (Sigma). *Phlebotomus papatasi* cells were maintained in Schneider's media (Sigma) supplemented with 10% fetal bovine serum and Penicillin (100 units/mL)-Streptomycin (100 μg/ml).

Genomic Sequencing.

EILV genome was sequenced by 454 sequencing (Roche Diagnostics Corp.). Briefly, viral RNA was extracted using TRIzol® LS (Invitrogen), DNase I (Ambion) treated and cDNA was generated by reverse transcription utilizing Superscript™ II system (Invitrogen) using random hexamers linked to an arbitrary 17-mer primer sequence. The cDNA was RNase H treated and randomly amplified by PCR with random hexamer linked 17-mer primer. Products were purified (Qiagen) and ligated to specific adapters for sequencing on the 454 Genome Sequencer FLX (454 Life Sciences) without fragmentation. The removal of primer sequences, redundancy filtering, and sequence assembly was performed by utilizing software programs at the GreenePortal website (available on the WorldWideWeb at tako.cpmc.columbia.edu/Tools/). Sequence gaps were filled by using primers based on pyrosequencing in both directions with ABI PRISM® Big Dye™ Terminator 1.1 Cycle Sequencing kits on ABI PRISM® 3700 DNA Analyzers (Perkin-Elmer Applied Biosystems). The terminal sequences for each virus were amplified using the Clontech SMARTer® RACE kit (Clontech). Full-length genome was verified by classical dideoxy sequencing using primers designed from the draft sequence to create products of 1,000 basepairs (bp) with 500 by overlaps.

Cloning and Rescue of Full-Length Infectious EILV Clone.

Figure 1B:
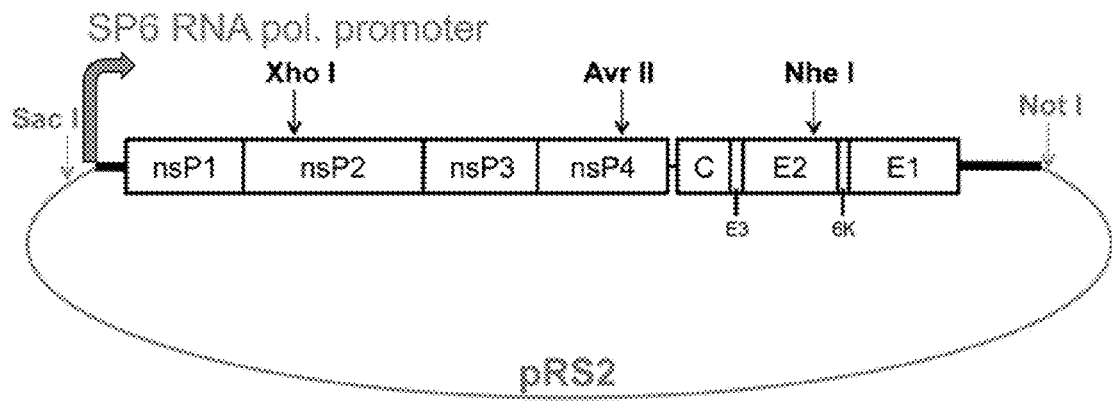

EILV cDNA clone was constructed utilizing standard molecular techniques. Briefly, EILV RNA was obtained by infecting C7/10 cells. Viral RNA was isolated from cell culture supernatant using the QIAamp® Viral RNA Mini kit (Qiagen). cDNA was produced by using random hexamers and Superscript® III (Invitrogen). cDNA fragments were amplified with Phusion® DNA polymerase (New England BioLabs) and EILV primers. Amplified PCR products were purified using QIAquick® Gel Extraction Kit (Qiagen). Fragments were cloned into pRS2 (FIG. 1B). The full-length cDNA clone was confirmed by ABI PRISM® Big Dye™ sequencing (Applied Biosystems). EILV infectious clone was rescued using standard techniques. EILV cDNA was linearized with Not I and in vitro transcribed using SP6 RNA polymerase transcription kit (Ambion). Approximately 4 pg of RNA was electroporated into C7/10 cells and supernatants were harvested at 48 hrs post-electroporation and stored at −80° C.

Phylogenetic Analysis.

Phylogenetic analysis was performed. *Alphavirus* sequences were downloaded from GenBank, aligned in SeaView utilizing the MUSCLE algorithm (Edgar, 2004, *Nucleic Acids Research*, 32:1792-97; Gouy et al., 2010. *Molecular Biology and Evolution*, 27:221-224). The sequences were aligned by deducing the amino acid sequence from open reading frames (ORFs) aligned and then returned to nucleotide sequences for subsequent analyses. Sequences were aligned as deduced amino acids (aa) from ORFs and then returned to nucleotide sequences for most analyses. The two ORFs were concatenated, and the C-terminus of nsP3 and the N-terminus of the capsid genes were removed from the analysis as these sequences display significant sequences divergence and produce poor alignments. Following manual adjustments, the complete alignment was split into non-structural and structural protein ORFs. Three analyses were performed; neighbor joining (NJ), maximum-likelihood (ML), and Bayesian. NJ analysis was performed utilizing PAUP* version 4.0 (Swofford, 1998, PAUP*: phylogenetic analysis using parsimony (*and other methods), version 4. Sunderland, Mass.: Sinauer Associates). Trees were generated utilizing p-distance algorithm and the robustness of NJ phylogeny was evaluated by bootstrap resampling of 1,000 replicates. ML and Bayesian analyses were performed utilizing the PHYLIP package and Metropolis-coupled Markov Chain Monte Carlo (MCMCMC) in MrBayes v3.1.2, respectively (Felsenstein, 1989, *Cladistics*, 5, 164-166; Ronquist and Huelsenbeck, 2003, *Bioinformatics* 19, 1572-74). Model test in PAUP was used to identify the best-fit nucleotide substitution model, GTR+I+G model (Posada and Crandall, 1998, *Bioinformatics* 14, 817-18). The robustness of ML and Bayesian phylogeny was evaluated by boostrap resampling of 100 and five million generations, respectively.

Serologic Tests.

Complement fixation (CF) and Hemagglutination-inhibition (HI) tests were performed using microtechniques described previously (Beaty et al., 1989, Arboviruses. Schmidt N J, Emmons R W, eds. Diagnostic Procedures for Viral, Rickettsial and Chlamydial Infections, Sixth Edition, Washington D.C.: American Public Health Association, 797-855). CF was performed using two full units of guinea pig complement and titers were recorded as the highest dilutions giving 3 or 4 fixation of complement on a scale of 0 to 4. HI tests were performed using immune sera and acetone-extracted ascitic fluids. Antigens and anti-sera were obtained from the Arbovirus Reference Center at the University of Texas Medical Branch.

Transmission Electron Microscopy.

Thin section and cryo-electron (cryo-EM) microscopy were performed as described previously (Ito and Rikihisa, 1981. Techniques for electron microscopy of rickettsiae. Burgdorfer W, Anacker R L, eds. Rickettsiae and Rickettsial Diseases. New York: Academic Press, 213-27; Travassos da Rosa et al., *Am J Trop Med Hyg.* 2001, 64(1-2):93-7; Sherman and Weaver, *J Virol.*, 2010, 84(19):9775-82). Briefly, monolayers of C7/10 cells infected at MOI of 10, 24 hours-post-infection, cell were fixed in 1.25% formaldehyde, 2.5% glutaraldehyde, 0.03% trinitrophenol and 0.03% $CaCl_2$ in 0.05 M cacodylate buffer pH 7.3, and washed in 0.1 M cacodylate buffer. Cells were scraped, pelleted 1% $OsO_4$ in 0.1 M cacodylate buffer, en bloc stained with 1% uranyl acetate in 0.1 M maleate buffer pH 5.2, dehydrated in ethanol and embedded in Poly/Bed® 812 (Polysciences). Ultrathin sections were cut on Reichert Ultracut S ultramicrotome, stained with 2% aqueous uranyl acetate and 0.4% lead citrate, and examined in a Philips 201 electron microscope at 60 kV.

For cryo-EM, virus was amplified on C7/10 cells at MOI of 0.5. 48-hrs-post-infection supernatants were harvested and clarified by centrifugation at 2,000 g for 10 min. Virus was precipitated overnight at 4° C. by adding polyethylene glycol and NaCl to 7% and 2.3% (wt/vol) concentrations, respectively. Virus was pelleted by centrifugation at 4,000 g for 30 min at 4° C. and precipitate was resuspended in TEN buffer (0.05 M Tris-HCl [pH 7.4], 0.1 M NaCl, 0.001 M EDTA). Virus was loaded onto a 20-to-70% continuous sucrose (wt/vol) gradient in TEN buffer and centrifuged at 270,000 g for 1 hr. Following centrifugation, visible virus band was harvested using a Pasteur pipette and centrifuged 4 times through an Amicon® Ultra-4 100-kDa-cutoff filter (Millipore) and resuspended in 1 mL of TEN buffer. The purified virus was applied to the holey films (R2×2 Quantifoil; Micro Tools GmbH; or C-flat; Protochips), blotted with filter paper, and plunged into liquid ethane cooled in a liquid nitrogen bath. Frozen grids were stored under liquid nitrogen and transferred to a cryo-specimen 626 holder (Gatan, Inc.) under liquid nitrogen before being loaded into a JEOL 2200FS electron microscope, equipped with an in-column energy filter (omega type) and a field emission gun (FEG) operating at 200 keV.

RNA Analysis.

C7/10 monolayers were infected with SINV or EILV at MOI of 10, 4 hrs-post-infection cells were be labeled with [$^3$H]uridine (20 µCi/ml) in the presence of dactinomycin (ActD) (1 µg/ml) for 3 hrs. Following labeling total cellular RNA was isolated by TRIzol (Invitrogen), denatured with glyoxal in dimethyl sulfoxide and analyzed by agarose gel electrophoresis using previously described conditions (Gorchakov et al., *J Virol.*, 2004 78(1):61-75).

Plaque Assay.

Virus titration was performed on freshly confluent C7/10 cell monolayers in six-well plates. Duplicate wells were infected with 0.1-ml aliquots from serial 10-fold dilutions in growth medium, 0.4 mL of growth media was added to each well to prevent cell desiccation, and virus was adsorbed for 2 hrs. Following incubation, the virus inoculum was removed, and cell monolayers were overlaid with 3 mL of overlay containing 1:1 mixture of 2% tragacanth and 2× MEM with 5% FBS, 2% tryptose phosphate broth solution, 2% Pen-Strep. Cells were incubated at 28° C. in 5% $CO_2$ for 3 days for plaque development, the overlay was removed, and monolayers were fixed with 3 mL of 10% formaldehyde in PBS for 30 mins. Cells were stained with 2% crystal violet in 30% methanol for 5 min at RT and excess stain was removed under running water and plaques will be counted.

One-Step Growth Curves.

Growth curves were performed on representative vertebrate and invertebrate cell lines in triplicates. Three independent dilution curves of EILV and a single dilution of SINV virus stocks were performed to obtain a MOI of 10. Each replicate was used to infect 50% confluent monolayers in 25 cm² flasks. Virus was adsorbed in 1 ml of growth medium for 2 hrs at 37° C. or 29° C. with occasional rocking to prevent cell desiccation. After the inoculum was removed, monolayers were rinsed five times with 12 ml of PBS to remove unbound virus, and 5 ml of growth medium was added to each flask. 0.5-ml aliquot were taken immediately after as a "time hr 0" (T0) sample and replaced with 0.5 ml of fresh medium. Flasks were placed at 37° C. or 28° C. and further samples were taken at 12, 24, 48, 72, and 96 hrs-post-infection. All samples were flash frozen in ethanol-dry ice and stored at −80 C for titration.

Infection with EILV-eRFP Construct.

EILV construct encoding enhanced red fluorescent protein (eRFP) under control of subgenomic promoter was constructed utilizing standard cloning techniques. Representative vertebrate (293-HEK, Vero, BHK-21, DEF, NIH 3T3), and invertebrate cell lines (C6/36, C7/10 *Culex tarsalis* and *Phlebotomus papatasi*) cell lines were infected at an MOI of 10. Light and fluorescent microscopy images were obtained at 24 hour intervals post infection.

Electroporation of EILV-eRFP RNA in vertebrate cells. EILV-eRFP cDNA was linearized with Not I and in vitro transcribed using SP6 RNA polymerase transcription kit (Ambion). ≈4 µg of RNA was electroporated into representative vertebrate (293-HEK, Vero, BHK-21, DEF, NIH 3T3), and invertebrate cell lines (C6/36, C7/10). Light and fluorescent microscopy images were obtained at 24 hour intervals post infection. SINV-eGFP replicon was utilized as positive control.

Example 2

Assay for Detecting *Alphavirus* Infection Using Eilat Virus Chimeras

Chimeras containing EILV replicative machinery (i.e. nonstructural proteins, 5' and 3' UTRs) and structural proteins of Old (Sindbis) and New (EEEV) World viruses were generated. Supernatants or concentrated EILV chimeras generated in mosquito cells were utilized as antigens in ELISAs. EILV/EEEV chimera diluted 1:100 or 1:1,000 in PBS could be readily detected by mouse polyclonal anti-sera and produced minimal cross reactivity (Tables 3-5)

A chimera containing EILV replicative machinery and structural proteins of Chikungunya virus (CHIKV) was generated. Supernatants of mosquito cells, infected with EILV/CHIKV, were diluted 1:2000 in PBS and utilized as antigen in ELISAs to detect mouse polyclonal anti-sera (Table 6).

TABLE 3

ELISA data generated with EILV/EEEV chimera diluted to 1:100 in PBS. Each data point represents average of 4-5 wells. O.D. (450 nm)

| Serum Dilution | EEEV-antisera | VEEV-antisera |
|---|---|---|
| 1:25 | 3.45 | 2.50 |
| 1:50 | 2.93 | 1.73 |
| 1:100 | 2.64 | 1.17 |
| 1:200 | 2.56 | 1.10 |
| 1:400 | 2.22 | 0.93 |
| 1:800 | 1.50 | 0.67 |
| 1:1600 | 1.42 | 0.60 |
| 1:3200 | 0.65 | 0.31 |

| Antibody | Dilution | O.D. (450 nm) |
|---|---|---|
| Primary antibody | 1:5,000 | 0.07 |
| Secondary conjugate | 1:5,000 | 0.06 |
| VSV-anti G antibody | 1:1,000 | 0.06 |
| Diluent |  | 0.06 |

TABLE 4

ELISA data generated with EILV/EEEV chimera diluted to 1:1,000 in PBS. Primary antibody and secondary conjugate were diluted 1:5,000. Each data point represents average of 3-4 wells.
O.D. (450 nm)

| Serum Dilution | EEEV-antisera | VEEV-antisera | CHIKV-antisera |
|---|---|---|---|
| 1:40 | 2.34 | 1.15 | 0.15 |
| 1:80 | 1.76 | 0.65 | 0.13 |
| 1:160 | 1.39 | 0.44 | 0.10 |
| 1:320 | 0.97 | 0.37 | 0.09 |
| 1:640 | 0.85 | 0.29 | 0.08 |
| 1:1280 | 0.53 | 0.18 | 0.07 |
| 1:2560 | 0.34 | 0.24 | 0.07 |
| 1:5120 | 0.22 | 0.13 | 0.08 |

| Antibody | Dilution | O.D. (450 nm) |
|---|---|---|
| Primary antibody | 1:5,000 | 0.06 |
| Secondary conjugate | 1:5,000 | 0.06 |
| VSV-anti G antibody | 1:1,000 | 0.06 |
| Diluent | | 0.06 |

TABLE 5

ELISA data generated with EILV/EEEV chimera diluted to 1:1,000 in PBS. Primary antibody and secondary conjugate were diluted 1:10,000. Each data point represents average of 3-4 wells.
O.D. (450 nm)

| Serum Dilution | EEEV-antisera | VEEV-antisera | CHIKV-antisera |
|---|---|---|---|
| 1:40 | 2.30 | 1.06 | 0.15 |
| 1:80 | 1.71 | 0.60 | 0.12 |
| 1:160 | 1.80 | 0.42 | 0.10 |
| 1:320 | 0.96 | 0.37 | 0.09 |
| 1:640 | 0.81 | 0.28 | 0.08 |
| 1:1280 | 0.52 | 0.18 | 0.08 |
| 1:2560 | 0.34 | 0.25 | 0.07 |
| 1:5120 | 0.22 | 0.13 | 0.07 |

| Antibody | Dilution | O.D. (450 nm) |
|---|---|---|
| Primary antibody | 1:10,000 | 0.06 |
| Secondary conjugate | 1:10,000 | 0.06 |
| VSV-anti G antibody | 1:1,000 | 0.07 |
| Diluent | | 0.06 |

TABLE 6

ELISA data generated with EILV/CHIKV chimera diluted to 1:2,000 in PBS. Primary antibody and secondary conjugate were diluted 1:10,000. Each data point represents average of 3-4 wells.
CHIKV ELISA O.D. (450 nm)

| Serum Dilution | CHIKV-antisera | EEEV-antisera |
|---|---|---|
| 1:50 | 1.53 | 0.23 |
| 1:100 | 1.40 | 0.14 |
| 1:200 | 1.19 | 0.10 |
| 1:400 | 1.08 | 0.07 |
| 1:800 | 0.94 | 0.06 |
| 1:1600 | 0.87 | 0.05 |
| 1:3200 | 0.79 | 0.05 |
| 1:6400 | 0.82 | 0.05 |

| Controls | Dilution | O.D. (450 nm) |
|---|---|---|
| Negative (Gamboa) | 1:100 | 0.09 |
| Primary Ab | 1:10000 | 0.05 |
| Secondary Ab | 1:10000 | 0.05 |
| Diluent | | 0.05 |

ELISA Protocol.

Antigen was bound to Immulon® 2HB flat bottom ELISA plates (Thermo Labsystem). EILV/EEEV chimera was diluted 1:1,000 in PBS (100 µL/well). Plates were incubated overnight 4° C. After incubation the plates were washed 5 times with 300 µL of 1×PBS containing 0.1% Tween™ 20 (Polyethylene glycol sorbitan monolaurate). The plates were then blocked with 1×PBS containing 0.1% Tween™ 20 (Polyethylene glycol sorbitan monolaurate) and 3% BSA, incubated for 1 hr at RT or overnight at 4° C., and washed 5 times with 300 µL of 1×PBS containing 0.1% Tween™ 20 (Polyethylene glycol sorbitan monolaurate).

The sample was diluted in 1×PBS containing 1% BSA and 0.1% Tween™ 20 (Polyethylene glycol sorbitan monolaurate). The desired starting dilution were determined. To identify the starting dilutions 2-3 fold serial dilutions were done. Incubated for 1 hr at RT or overnight at 4° C. and washed 5 times with 300 µL of 1×PBS containing 0.1% Tween™ 20 (Polyethylene glycol sorbitan monolaurate). 100 µL primary antibody biotin-SP-Affinipure Goat anti-Mouse IgG (Jackson Labs Cat#: 115-065-164) diluted 1:10,000 in 1×PBS supplemented with 0.1% Tween™ 20 (Polyethylene glycol sorbitan monolaurate) and 1% BSA was added. The plates were incubated for 1 hr at RT or overnight at 4° C. and washed 5 times with 300 µL of 1×PBS containing 0.1% Tween™ 20 (Polyethylene glycol sorbitan monolaurate).

After incubation with primary antibody, 100 µL streptavidin-horseradish peroxidase conjugate (500 units/ml stock, Roche Immunochemical, Indianapolis, Ind.) diluted 1:10,000 with 1×PBS supplemented with 0.1% Tween™ 20 (Polyethylene glycol sorbitan monolaurate) and 1% BSA was added. Incubated for 1 hr at RT or overnight at 4° C. and washed 5 times with 300 µL of 1×PBS containing 0.1% Tween™ 20 (Polyethylene glycol sorbitan monolaurate). After addition of conjugate, 100 µL of TMB (3,3',5,5'-tetramethyl benzidine, Sigma) was added per well. The reaction was stopped by adding 100 µL/well of IN sulfuric acid. The plates were read at 450 nm.

The invention claimed is:

1. A chimeric *alphavirus* having a genome comprising (a) a non-structural protein coding segment having at least 95% identity to a non-structural protein coding segment, nucleotides 57 to 7304, of SEQ ID NO:1 and (b) a structural protein coding segment of chikungunya virus.

2. The chimeric *alphavirus* of claim 1, wherein the structural protein coding segment of the chikungunya virus encodes C, E1, and/or E2.

3. The chimeric *alphavirus* of claim 1, wherein the structural protein coding segment of the chikungunya virus encodes C, E1, and E2.

4. An immunogenic composition comprising the *alphavirus* of claim 1.

5. A method of stimulating an immune response in a subject comprising administering an effective amount of an immunogenic composition of claim 4.

6. A diagnostic kit comprising a chimeric Eilat *alphavirus* comprising a heterologous polypeptide of a non-Eilat *alphavirus*.

7. The kit of claim 6, wherein the non-Eilat *alphavirus* is selected from the group consisting of Ross River (RRV), chikungunya (CHIKV), Sindbis (SINV) Venezuelan equine encephalitis (VEEV), Eastern equine encephalitis (EEEV) and Western equine encephalitis (WEEV) protein.

8. The kit of claim 6, wherein the non-Eilat *alphavirus* is chikungunya virus.

9. The kit of claim 6, wherein the chimeric Eilat *alphavirus* is coupled to a substrate.

10. The kit of claim 9, wherein the chimeric Eilat *alphavirus* is covalently coupled to a substrate.

11. The kit of claim 6, further comprising a detection reagent.

12. The chimeric *alphavirus* of claim 1, wherein the chimeric *alphavirus* has a nucleotide sequence that is 90% identical to SEQ ID NO:134.

13. The chimeric *alphavirus* of claim 1, wherein the chimeric *alphavirus* has a nucleotide sequence of SEQ ID NO:134.

* * * * *

SEQUENCE LISTING

<160> NUMBER OF SEQ ID NOS: 134

<210> SEQ ID NO 1
<211> LENGTH: 11634
<212> TYPE: DNA
<213> ORGANISM: Eilat virus
<220> FEATURE:
<221> NAME/KEY: 5'UTR
<222> LOCATION: (1)..(56)

```
<220> FEATURE:
<221> NAME/KEY: misc_feature
<222> LOCATION: (57)..(7304)
<223> OTHER INFORMATION: Non-structural protein coding region
<220> FEATURE:
<221> NAME/KEY: misc_feature
<222> LOCATION: (7387)..(11088)
<223> OTHER INFORMATION: Structural protein coding region
<220> FEATURE:
<221> NAME/KEY: 3'UTR
<222> LOCATION: (11089)..(11634)

<400> SEQUENCE: 1
ataggctgca cattacacat tagaaatcgt aacgtagcct tccactttca tcgaacatgg      60
agaaaccaac tgttaacgtc gacgtagacc cccaaagtcc gttcgtactg cagttgcaga     120
aacacttccc ccagtttgag atagtggcta acatggtcac cccgaatgac cacgccaatg     180
cgagagcctt ctcccattgc gccagtaaac tgatcgaagc ggaggtacct gttaccacgc     240
cgatcatcga catagggagc gcacctgctc gtagaatgta ttccgagcac cgctaccact     300
gcgtttgccc tatgaaatgc ccagaagatc cggaccgcct taccacctat gcgaaccgcc     360
ttgtcgaaaa cgccacgaag atcgctaaca acggctaga cgctaagcta caagaccta      420 agcaagtctt agaaactcct gacatagaaa cggactcgat ctgcttccac gacgacgcta     480
catgccgttg ggtagcggag gtctctgtca tgcaggacgt gtacatagac gcccccagct     540
ctatctacca ccaagcacta aaggcatcc gcaaaatata ctggattggc ttcgacacca      600
cgccgttcat gttcaaagca ctcgccggat cttacccctc gtacaacacc aactgggccg     660
acgagaaagt actcgaagca cgaaacatcg gcctatgcag taccacactg agcgaaggat     720
cgacagggaa actgtcgatc atgcgaaaga gagattgtt acctggtgct caggtctact       780
tttctgttgg gtcaacactg taccctgaaa accgctccaa tcttatgagt tggcacctcc     840
cttccgtgtt ccatctgaag ggtagaaacg cattcacttg ccgctgtgac acagtggtca     900
actgcgacgt ttacgtggtt aagaaaata ccattagccc caacctcata ggtacaccag      960
caggatacgc ggtgactaac aacagtgagg gattcttact ttgtaaagtc actgacactg    1020
tacgcggcga acgggtttcg ttccccgtgt gcatgagtat accggcaacc atctgcgacc    1080
aaatgactgg catactagcc acagacataa acccggaaga cgcacaaaaa ctgctggttg    1140
ggctcaacca gcgtattgtc gtcaacggaa agaccaaccg aaacgtcaac acgatgcaga    1200
accatcttct accggcagta gcacaaggat ttagcaaatg ggccaaggaa cgcaaagcag    1260
acggagacga cgagaaacat ctcgggactc gtgaacgctc cttaaccttc ggatgtctct    1320
gggcgtttag gaccaagaaa gtacactcat tctaccgccc acctggtaca cagaccatcg    1380
tcaaggtgga atcagtgttc acagcgtcgc cccttgccat ccccatccgg caaacatctt    1440
tgcctatctc actgcgcctg aagcttaaga tggcgatagc aaagaagcaa aacaacccca    1500
tcgctactat cacacagacg caaattacga acgccatcga attccaaaaa gaagctactg    1560
aaacggcgcg cgcggttgaa ctcaacaatg ctctcccgcc cctgcgtgcc accgaacagg    1620
atccgacacc ttctgtagaa cacgtcgtct gcgaggtaga agaactctcc gacgacatcg    1680
gcggggcgct ggtcgagacc ccacgtgac acgtgcgaat cttaccccag ccaaccgatg     1740
tcaaggtagg gaactacctt gtcatctccc cgcaagctgt gcttcgaaac gataaattaa    1800
gtagactaca ccccctagca gagcaaataa aggtcatcac acacaccggg cgcaagggcc    1860
gatacgaagt ggcgccgtat agcggaaaaa tgctactacc atgcgtacc tccgtcccat      1920 ggcctcagtt ctgcgcactt gctgaaagtg caaccctagt gttcaacgaa cgagaaatga    1980
```

```
tcgaccgtaa attagcgtat atcgcacagc acggcccagc cttgaacaca gacgaggaac    2040
aatacaaggt tatcaaagca tcagcagcag acagcgaata cgtgttcgac atcgaccgaa    2100
tgaggtgcgt gccgacaaaa gaggcaaacg gtctagtatt ggtagggggaa ctcacacaac   2160 caccctacca cgaactcgct atgcagggtc tatatactag accagccgca ccctatccaa    2220
tagagaccat aggtgtcatc ggcacgccag gctccgggaa atcagcgatc attaagaaca    2280
ccgtcaccac caaagacctc gtcactagtg gcaagaaaga gaactgcaaa gagatagaaa    2340
ctgacgtact ccgccttcgc aacctcgtca ttaagagccg cacggtggac tccgtgctac    2400
tcaacggttg cacccaagag gtagacgttc tacacgtaga cgaggcattc gcgtgtcacg    2460
ccggaacgtt gttagctctc atcgctatcg taaaaccgcg ttgtaaagta gtactgtacg    2520
gagacccgaa acaatgcggc ttcttcaatc tcatgcagat caaagtccat ttcaacaacc    2580
cggaggttga cgtctgctcc caattacact acaagtatat atccaggcgc tgcatcctgc    2640
ctgtcaccgc catcgtatct tccatacatt acgacggcaa aatgcgcaca acgaacaccg    2700
ccgaccaacg tatagagatt gatactacag ggacctcgaa gccgaaaccg accgacctca    2760
tcctcacatg cttccgcgga tgggttaaac agctccaact cgagtatccc cgtaacgaag    2820
taatgaccgc agccgcctct caaggcctga cccgtaaacg tgtatatgct gtccgctaca    2880
aggtcaatga gaaccccctc tacgccttta cttcagaaca cgtgaacgtg ctgcttacca    2940
ggacggaaca tacccctagta tggaaaacgc tacaaggaga tccatggatc aagcacctgt    3000
ccaatgtacc gaaaggaaac ttctccgcga cggtcgacga atggcacgcc gagcacgaac    3060
gcatcatgaa cgccatccgc atgcccaccc ccgaagtcaa tgccttctct tgtaagacta    3120
acgtatgctg ggcgaaggca cttgtaccgg tcttggcgac cgctggtctg aagctctctg    3180
gcgcccaatg gacagagctg ttcccccaat tcgaaagaga cgaaccgcac tcagctacgt    3240
ttgctcttga cgtcttatgc ataaagtact tcggaatgga cctcactagc ggcatcttcg    3300
ccaaaccgac agtgcccttg accttccacc cggtaagccg ttatcacccg caagcacact    3360
gggacaacgc caacggagaa caacgctacg gattcgaccc tgacatcgcc aaggcactcg    3420
cacgccgatt cccagtgttc tctcaggccg ctaaaggaca tgccatctca cctatccttg    3480
gtacgacgca cactctttca agccgcgaca actacgtgcc cgtcaaccgt attgtcccgc    3540
acacactgaa aggagagtac acgtatgtca aacaagattc ccttgcatcc gttctctctg    3600
ctgtgcaagc atttttcagtc ttagttgtct cgtcagagcc catcgcgagc gccacgaagc    3660
aaatcacttg ggtggccccg ctaggcacag ccggctgcat acacacgcac aggctgccct    3720
ggggcttccc aaaaatgtcg ttacacgatg ccgtggcagt caatatggag accgaatacc    3780
gaggacatca ctaccagcaa tgcgaagatc acgtcgccat cctcaagacc ctgggcaagt    3840
ctgccctcgc caacctaaga cctggcggca ccctgattct gcgcacctac ggttacgcgg    3900
accgcaacag cgagaatgta atcactgcac ttgcccgcaa gttcgcgaga gtaactgcag    3960
tcaggtctag taacccctca agcaataccg aaatctactt gatcttcagg aaattcgaca    4020
acaaccgatc cagacagttt accttgcatc atcttaaccg cgcgatttcc gcgctctacg    4080
aaagtccatg cgacccccgac ggagtgggcg ccgcccatc atactcggtg atcagaggcg    4140
acataaccgc gactaactcc cacgccattg tcgtccctgt cacgccggag cgaaaagacg    4200
gcgtgtatcg cgcttgtagc aagaaatggg gccccctacc tcgcctggag tggaccgaag    4260
gtgccacctt gttctcgccc ggttcaccag ccactctgca agtatgtgta ccctcgctcc    4320
```

```
agaatacgga cactacatca acccagcaag cctaccgcgc catcgccaaa gttgtcgtcg    4380
acgagcagat tccgtcacta tctctacccg tcctcaccat gaagaagacc ggcacagcag    4440
acaccgtatc agaatccttg aaccacctag ttaccgctct ggaccaaacc gatgcaaatg    4500
taactattta ctgtctcgac aaaagcaggc tcataaaaat caaggaagta attgcacgca    4560
aggaagccgt caccgagctt atcgacgacg acctagaaat cgacgaggaa ctgacatggg    4620
tccaccccga tagctgccta cgcaaccgca ccggttttag caccgacaaa ggaaaactgt    4680
actcatatct ggaagggacc aagttccacc agatggccaa ggacttcgca gagattaggt    4740
cactattccc tgacgagatg gaagctaacg aacacatatg ctcactcatc ttaggggaaa    4800
cgatagatgg catccgagaa cgctgtccag tgacagacaa tccgccatca tcaccgccca    4860
agactgtacc ctgcttgtgc atgtacgcca tgacccagaa acgcgcccta cggctcaaga    4920
gcaattctgt cacccaaatc acagtctgct cgtccttcgt tctcaagaag caccacatca    4980
aaggggtaca agaatccaa tgcacggcac ctatgttatt caacccgaca ccattaactt    5040
ccaggacggt ccgcactccg ccacaagtct cagcacgagc cgcactcgat cttcctcccg    5100
ttgcacctat gccttctgta cctgcaccgg ttagcctgac gcctacgagg cgtgcaccac    5160
caccgcccct taccaaacga cccgttgtcg tacgtccgtc gacgcctcca ccgccgccac    5220
cagtacgcca gacaccaacg ccagtgctcg cgccacggac tggttctacg gcagcaccca    5280
ctccgacgcc acgcctctcg ttatctacgg accagccatc cgtagacatt tcgttcggag    5340
acttttcccc cgcagaaacg atgtctttga tgctgtcgtc ccctggctct gacaccgcca    5400
gtatcacctt cggtgacttc gacgaggacg aggtagaatc tatagtagga cgggaatatt    5460
gactaaccgg agcgggaggg tacatatttt cttcagacac cggcagtggg catttacaac    5520
aacgttcggt ccttcaaaac cgcacgaccg agacaattat agagcgagtc acacatgacc    5580
gcatccacgc cccacagctc aatgaagcca gggaagaagt tctgaagtta aagtaccaaa    5640
tgtatccctc cgacgctaac aaaagtaggt accgcgcccg caaagtagag aaccaaaaag    5700
ccatatgcat cagccgcctc acggcaggta gccgcagtta ttctttcgga caacagaag    5760 ccgaatgcta cagagaaact taccctgcag tcatgtactc gtcttcgcta ccatcctcct    5820
actcggcgcc gaccacggct gtggctgtgt gcaacgcgta tctggcagct aattacccca    5880
ccgtcgcctc gtatcagatc actgacgagt acgacgcgta cttagacatg gtcgacggta    5940
ctatggcttg cttagacaca gcgtccttca acccttctaa actaaggagt tttccgaagg    6000
tccacaagta tctggaacct actatccgta gtgcagtacc atctcccttc cagaatacac    6060
tacaaaacgt tctaactgcc gccactaagc gtaactgtaa cgtcacccaa atgcgcgagc    6120
taccgacact cgattctgcc gcatttaacg tagagtgctt taggaaatac gcctgcaaca    6180
acgactactg gcaagaatat gcggataaac ctatccgcat aactacggaa tacgtcaccg    6240
cctacgttgc caagctaaag ggacctaaag ctgccgcctt gttttccaaa acacacgact    6300
taccggcgct cggcgaagta cctatggacc gcttcgtcat ggacatgaag agagacgtta    6360
aagtgacccc tggcagtaag cacaccgaag aacgcccgaa agttcaggta attcaagcag    6420
ctgaacctct ggccactgcc tactatgcg gcatccatcg tgaactggtc cggcgactca    6480
ctgctgcgct ccttcccaac atccacactc tttttgacat gtccgcagag gacttcgacg    6540
ccacactggc ccaccacttc aaaaagggcg accccgtact ggaaacagac atagcatcct    6600
tcgacaaaag tcaggatgac gccttagcac tcacagggct aatgatcctg gaggacctag    6660
gagtagacca gccccctcatg gacctgatcg aggcagcttt cggagatata accagcacgc    6720
```

```
acctacccac cggagcacgt tccggtttg gcgccatgat gaagtctggt atgtttctta      6780
ccctgttcat caacaccgtc cttaacgtgg taatagccag ccgtgtatta gaagacaagt      6840
taacgcactc cgcctgcgcc gcattcatcg gcgacgacaa catcatacac ggagtcatat      6900
ctgaccgtat aatggctgac cgatgcgcta catggatgaa tatggaagtc aaaattatag      6960
acgcggtcat gggagactac cctccctatt tctgtggcgg gttcctcatc atagacagcg      7020
tgaccaaaca cgcatgccga gtcgccgacc ccctgaagag actattcaaa cttgggaagc      7080
cgcttaccgc ggacgacgac cacgacgatg accggagaag agccctcgag gatgaaacta      7140
aagcatggtt tcgggtaggg atcagagaag gcatcaccgc cgccgtatca tcaagatacg      7200
aagtcgacaa catactgccc gttctcttag cccttagaac cttttgcttta tctacgcgca      7260
acttctctgc cttacgggga acacttaaga ccctctacaa ctaacctaaa tagtgcgcgt      7320
attatcaata ctactagcac actattaccc gtgtacgtac caacggcact acttgcacaa      7380
gtcaacatgt tccgcaccaa taacaaccgc caacgtcgtc aacagccacg ctcccgcagg      7440
caacgttcac cctcgcggcc cctgcagcgc cgacaagacg atgcactctc caaacaggtc      7500
cgcgccctaa ctaccgcagt tcagaaacta gtggtggcag gaaatcgccg cccaccgcct      7560
tccccccgag ccaaggcgcc tggaccagcc caaccacgac cagctaaagc gcccgtcaaa      7620
actccagcca agagaggacc agcccctaag cgtaaacccg gaaagagaga acgtaccgcg      7680
ctccgcctgc aggcagaccg agtcttcccc gtcgttaatg acaaacaagt cacggtcggc      7740
tatgctgtag cgctggaagg gcgtgtcatg aagcctttgc acgtcaaggg cactattgac      7800
caccctctcc ttgcctcact caagtttacc aaatccacgt ccttcgacat ggagtacgcc      7860
gctctaccaa ccaccatgcg ctctgaagcc tttgcttaca ccagcgagca cccagacggg      7920
ttctacagct gggtccatgg cgccgtacag tgcaccaacg ggcgcttctc catccctaca      7980
ggggcaggag gccctggcga cagcggcagg ccaatcctcg acaacacagg caaagtcgta      8040
gcccttgtcc ttggaggtgc aaatgaaggc actcgcacgt ctctctcggt agtcacgtgg      8100
aacaagtcag gcaccgcagc caagaccaca cccgacgaca cagtggagtg gtccgccatc      8160
gtgaccgcac tttgcgtact cggcaacgcc tccttcactt gcaccgagcc accgatttgc      8220
ttcgacaccc atccaggaga cacccctcgg atgctcgagg acaacgtcga ccaccccatg      8280
tactatgacc ttatgtacgc cgccctacta tgtaaccacc agcaaaaacg agcccgtaga      8340
gccgtcgccc cgaaaccgga cgaatatcgc cttgcgtctc cctacgtggg gcgatgcgca      8400
gcatgctcaa acggcatcac ctgcttcagc cccatcaagc ttgaatccgt atggacaaca      8460
ccacacagct cggtcctaaa aatgcaacta tcggtacttt tcggtataga cgaaacaggc      8520
aaattggaca acacagtcct cagttacatg tccccgacgg agcatacggt gaaaagcatg      8580
ccgatcacgg cactaaccgc atccacaacc ggaccatgta tcatcacggc cacacgaggc      8640
tatttcgcgc tggcacagtg cccaccaggt gacgtgctca ctgtagcaat gggctctcat      8700
cactgctcca ttgagtccga gcacctcaga ccctcagtgg tcgcgaaga attcgcctct      8760
acaccgctcc acggcgtccg gcgcccgtgc tctacctatg acgccgccaa atacaccagc      8820
acttctgaaa tgacccctcca ccgcgccaaa ccgcaggcct cagactcact cctgtctatc      8880
gtaaacgaca ctgtccaaat caccgtgtcg tccaacctga ccgtcagtta cgagtgcctc      8940
tgcgacggct accactccgg cttcgtacgt gcaacaacac ttatccctgg atgcactaat      9000
accaaccaat gcattgcatc cgtaaacgac aagacgcgct ggtatcccaa cacggacgac      9060
```

```
ttcatcagac acaccgacca cagccccaga ggtaaaatca acgttcctt  cccgctagag    9120
gcaggtgaat gcctggtccc gctagcccgc tccccagcta tccggtactc ccgaaatgag    9180
gtggagctca cactggtcac gacccgtaag gccctttgt  ccacacggca actcggctcc    9240
gaaccaaacg caacctctga gtggatcaca tcctccactc gtcggacctt ttacttgcct    9300
gccgcagggc tagagttcac ttggggtaac aacgaccccg tccgcgtttg gcctcaagcc    9360
tcagccgacg gggatgcgca cggtctccca cacgaaatcg ttgcgtacta ttacagcagg    9420
tccctctct  tcaccatcgt ggccgtcacc cttatctctg caatcgtgct cgcctcgctg    9480
gccttctgtt gctgcaagtg gacctctttc cgatccgcac tccgctcgcc atacgccctg    9540
gcaccgaacg caaccgtacc catgtgtctc acattgctgt gctgcatccg tcaagcaaaa    9600
gcagacacat acttcgacgc cgccagctat ctctggaaca actaccagcc gctattctgg    9660
gcacagttgg cgataccaac cgcctccatt tttgtgctct ttaaatgctg ctcactcgcc    9720
gtggcttttt tagctgttgt gggcgcatcg cttcccctag caagcgccca cgaacatgcg    9780
gccaatgttc ccaactctcc actcttgtcg tataaagccg tcgttacacg ccctggatat    9840
acaccccttg ccctagaaat tcgggttttg gaaaaccgta tccaaccgac aacactcacc    9900
cactattaca cttgctccta ccgcaccgta gtcccgtcgc ctacggtcaa atgctgtggt    9960
agtttgcagt gcggttcttc cagtctaccc gattaccgct gcaaggtgtt caccggagta   10020
tacccattta tgtggggagg ggcccagtgt ttctgcgata ctgagaactc ccaaatgagt   10080
gagagttacg tcgacaagga cccgtcctgc cctaccgacc acgcggaagc ggtagccacc   10140
cagaaccccg tggtacgcgc cacactacag atcactatag gcaacgccac tactcgcacc   10200
gacgtgtacg ttaacggcgt ttaccgagc  tacactaatg gagcgaaagt cattgccggg   10260
ccgctctcct ctgtatggag tcctttcgca gacaaggtgg tcatctacca gaggcgcgtt   10320
tacaatcacg cgttccccga atatggtgcc ggcactcctg gcactttcgg cgacctccaa   10380
ctccccagcc ttcgcgccaa ggactttttc gccaacaccg ggctagtcct caatcgaccc   10440
gacacttctt cgctgcacgt gccgtacaca caagtaccga gcgggtttgt cacctggaga   10500
gaccagcact tgcctgatct tcaacaaacc gctccatatg gctgcgccat tcaagcagt    10560
ccgctgcagg caattaattg ctcgtacggc agtatccctg tgtccatcga cattcccgac   10620
gcctccttca cccgctcctt cgacgcacca tccgttctt  cactgaaatg cactcctatt   10680
gagtgcgtcc actcggccgg gtacggaggc cttctcagac tagactacgt cgccgacaag   10740
gccggcactt gcagtcttca ttcgcacagt gatgccgtcc ttatgaagga ttcactcctc   10800
agcattaacg caacgggatc ctacacaggt ctttttctcga cggccagccc ccaagtcaag   10860
ttcaccatca ccctgtgctc ggcggaggtc agctgcgaga ctgcgtgcaa gccaccactc   10920
gaacacgcct catcacaccc gcacctgacg tcacagactt tcgactccgc tatatcaaca   10980
tccgcctgga catggttgct cagcctattc ggagggtcaa tatcacttgt gaccgtaggc   11040
atctttattg cggcagcctt gtacatcgtc aattgcagac gtcgctaaca ttatcactta   11100
agaacccgcc cacatatata gggctacata gttcacggga agaacaaccc ccctaatagt   11160
aacaaaacaa taaagtaca  aaaacaggta tcagccccctt agcgctgcat aatctatagt   11220
tcacgggaaa gaacaaaccc ctaatagtaa caaaactgca aaacacaaaa acaggtatca   11280
gccccttaga gctgcataat cacatagtcc acgggacaga tcaacccccct attagcaaca   11340
aaacacaaaa tcccaaaaac aggtataagt acccttagta cttactagta ctcactctag   11400
ttcacaggga agaacaaccc ctaaatagta actaaacaca aaacccaaaa acaggtatag   11460
```

-continued

| | | |
|---|---|---|
| gtacccttag tacctccaat ttgcccatcc atcgggcccg ctcaagccga actcacagag | 11520 |
| acgtaggccc cgaactccaa ggagacgtag ggataaaagt gctgaactca cagagacgta | 11580 |
| agcacaacaa tttgttttta atatttccaa aaaaaaaaaa aaaaaaaaaa aaaa | 11634 |

<210> SEQ ID NO 2
<211> LENGTH: 7248
<212> TYPE: DNA
<213> ORGANISM: Eilat virus

<400> SEQUENCE: 2

| | | |
|---|---|---|
| atggagaaac caactgttaa cgtcgacgta gaccccaaa gtccgttcgt actgcagttg | 60 |
| cagaaacact tcccccagtt tgagatagtg gctaacatgg tcaccccgaa tgaccacgcc | 120 |
| aatgcgagag ccttctccca ttgcgccagt aaactgatcg aagcggaggt acctgttacc | 180 |
| acgccgatca tcgacatagg gagcgcacct gctcgtagaa tgtattccga gcaccgctac | 240 |
| cactgcgttt gccctatgaa atgcccagaa gatccggacc gccttaccac ctatgcgaac | 300 |
| cgccttgtcg aaaacgccac gaagatcgct aacaaacggc tagacgctaa gctacaagac | 360 |
| cttaagcaag tcttagaaac tcctgacata gaaacggact cgatctgctt ccacgacgac | 420 |
| gctacatgcc gttgggtagc ggaggtctct gtcatgcagg acgtgtacat agacgccccc | 480 |
| agctctatct accaccaagc actaaaaggc atccgcaaaa tatactggat tggcttcgac | 540 |
| accacgccgt tcatgttcaa agcactcgcc ggatcttacc cctcgtacaa caccaactgg | 600 |
| gccgacgaga agtactcga agcacgaaac atcggcctat gcagtaccac actgagcgaa | 660 |
| ggatcgacag ggaaactgtc gatcatgcga agaagagat tgttacctgg tgctcaggtc | 720 |
| tactttctg ttgggtcaac actgtaccct gaaaaccgct ccaatcttat gagttggcac | 780 |
| ctcccttccg tgttccatct gaagggtaga aacgcattca cttgccgctg tgacacagtg | 840 |
| gtcaactgcg acggttacgt ggttaagaaa ataaccatta gccccaacct cataggtaca | 900 |
| ccagcaggat acgcggtgac taacaacagt gagggattct tactttgtaa agtcactgac | 960 |
| actgtacgcg gcgaacgggt ttcgttcccc gtgtgcatga gtataccggc aaccatctgc | 1020 |
| gaccaaatga ctggcatact agccacagac ataaacccgg aagacgcaca aaaactgctg | 1080 |
| gttgggctca accagcgtat tgtcgtcaac ggaaagacca accgaaacgt caacacgatg | 1140 |
| cagaaccatc ttctaccggc agtagcacaa ggatttagca aatgggccaa ggaacgcaaa | 1200 |
| gcagacggag acgacgagaa acatctcggg actcgtgaac gctccttaac cttcggatgt | 1260 |
| ctctgggcgt ttaggaccaa gaaagtacac tcattctacc gcccacctgg tacacagacc | 1320 |
| atcgtcaagg tggaatcagt gttcacagcg tcgccccttg ccatccccat ccggcaaaca | 1380 |
| tctttgccta tctcactgcg cctgaagctt aagatggcga tagcaaagaa gcaaaacaac | 1440 |
| cccatcgcta ctatcacaca gacgcaaatt cgaacgcca tcgaattcca aaaagaagct | 1500 |
| actgaaacgg cgcgcgcggt tgaactcaac aatgctctcc cgcccctgcg tgccaccgaa | 1560 |
| caggatccga caccttctgt agaacacgtc gtctgcgagg tagaagaact ctccgacgac | 1620 |
| atcggcgggg cgctggtcga gaccccacgt ggacacgtgc gaatcttacc ccagccaacc | 1680 |
| gatgtcaagg tagggaacta ccttgtcatc tcccccgcaag ctgtgcttcg aaacgataaa | 1740 |
| ttaagtagac tacacccct agcagagcaa ataaaggtca tcacacacac cgggcgcaag | 1800 |
| ggccgatacg aagtggcgcc gtatagcgga aaaatgctac taccatgcgg tacctccgtc | 1860 |
| ccatggcctc agttctgcgc acttgctgaa agtgcaaccc tagtgttcaa cgaacgagaa | 1920 |

```
atgatcgacc gtaaattagc gtatatcgca cagcacggcc cagccttgaa cacagacgag    1980
gaacaataca aggttatcaa agcatcagca gcagacagcg aatacgtgtt cgacatcgac    2040
cgaatgaggt gcgtgccgac aaaagaggca aacggtctag tattggtagg ggaactcaca    2100
caaccaccct accacgaact cgctatgcag ggtctatata ctagaccagc cgcaccctat    2160
ccaatagaga ccataggtgt catcggcacg ccaggctccg ggaaatcagc gatcattaag    2220
aacaccgtca ccaccaaaga cctcgtcact agtggcaaga agagaactg caaagagata    2280 gaaactgacg tactccgcct tcgcaacctc gtcattaaga gccgcacggt ggactccgtg    2340
ctactcaacg gttgcaccca agaggtagac gttctacacg tagacgaggc attcgcgtgt    2400
cacgccggaa cgttgttagc tctcatcgct atcgtaaaac gcgttgtaa agtagtactg    2460 tacggagacc cgaaacaatg cggcttcttc aatctcatgc agatcaaagt ccatttcaac    2520
aacccggagg ttgacgtctg ctcccaatta cactacaagt atatatccag gcgctgcatc    2580
ctgcctgtca ccgccatcgt atcttccata cattacgacg gcaaaatgcg cacaacgaac    2640
accgccgacc aacgtataga gattgatact acagggacct cgaagccgaa accgaccgac    2700
ctcatcctca catgcttccg cggatgggtt aaacagctcc aactcgagta tccccgtaac    2760
gaagtaatga ccgcagccgc ctctcaaggc ctgacccgta acgtgtata tgctgtccgc    2820 tacaaggtca atgagaaccc cctctacgcc tttacttcag aacacgtgaa cgtgctgctt    2880
accaggacgg aacatacccct agtatggaaa acgctacaag gagatccatg gatcaagcac    2940
ctgtccaatg taccgaaagg aaacttctcc gcgacggtcg acgaatggca cgccgagcac    3000
gaacgcatca tgaacgccat ccgcatgccc acccccgaag tcaatgcctt ctcttgtaag    3060
actaacgtat gctgggcgaa ggcacttgta ccggtcttgg cgaccgctgg tctgaagctc    3120
tctggcgccc aatggacaga gctgttcccc caattcgaaa gagacgaacc gcactcagct    3180
acgtttgctc ttgacgtctt atgcataaag tacttcggaa tggacctcac tagcggcatc    3240
ttcgccaaac cgacagtgcc cttgaccttc caccgggtaa gccgttatca cccgcaagca    3300
cactgggaca acgccaacgg agaacaacgc tacggattcg accctgacat cgccaaggca    3360
ctcgcacgcc gattcccagt gttctctcag gccgctaaag gacatgccat ctcacctatc    3420
cttggtacga cgcacactct ttcaagccgc gacaactacg tgcccgtcaa ccgtattgtc    3480
ccgcacacac tgaaaggaga gtacacgtat gtcaaacaag attcccttgc atccgttctc    3540
tctgctgtgc aagcattttc agtcttagtt gtctcgtcag agcccatcgc gagcgccacg    3600
aagcaaatca cttgggtggc cccgctaggc acagccggct gcatacacac gcacaggctg    3660
ccctggggct tcccaaaaat gtcgttacac gatgccgtgg cagtcaatat ggagaccgaa    3720
taccgaggac atcactacca gcaatgcgaa gatcacgtcg ccatcctcaa gaccctgggc    3780
aagtctgccc tcgccaacct aagacctggc ggcaccctga ttctgcgcac ctacggttac    3840
gcggaccgca acagcgagaa tgtaatcact gcacttgccc gcaagttcgc gagagtaact    3900
gcagtcaggt ctagtaaccc ctcaagcaat accgaaatct acttgatctt caggaaattc    3960
gacaacaacc gatccagaca gtttaccttg catcatctta accgcgcgat tccgcgctc    4020 tacgaaagtc catgcgaccc cgacggagtg ggcgccgccc catcatactc ggtgatcaga    4080
ggcgacataa ccgcgactaa ctcccacgcc attgtcgtcc ctgtcacgcc ggagcgaaaa    4140
gacggcgtgt atcgcgcttg tagcaagaaa tggggccccc tacctcgcct ggagtggacc    4200
gaaggtgcca ccttgttctc gcccggttca ccagccactg tgcaagtatg tgtaccctcg    4260
ctccagaata cggacactac atcaacccag caagcctacc gcgccatcgc caaagttgtc    4320
```

```
gtcgacgagc agattccgtc actatctcta cccgtcctca ccatgaagaa gaccggcaca    4380
gcagacaccg tatcagaatc cttgaaccac ctagttaccg ctctggacca aaccgatgca    4440
aatgtaacta tttactgtct cgacaaaagc aggctcataa aaatcaagga agtaattgca    4500
cgcaaggaag ccgtcaccga gcttatcgac gacgacctag aaatcgacga ggaactgaca    4560
tgggtccacc ccgatagctg cctacgcaac cgcaccggtt ttagcaccga caaggaaaa    4620 ctgtactcat atctggaagg gaccaagttc caccagatgg ccaaggactt cgcagagatt    4680
aggtcactat tccctgacga gatggaagct aacgaacaca tatgctcact catcttaggg    4740
gaaacgatag atggcatccg agaacgctgt ccagtgacag acaatccgcc atcatcaccg    4800
cccaagactg taccctgctt gtgcatgtac gccatgaccc cagaacgcgc cctacggctc    4860
aagagcaatt ctgtcaccca aatcacagtc tgctcgtcct tcgttctcaa gaagcaccac    4920
atcaaagggg tacagaagat ccaatgcacg gcacctatgt tattcaaccc gacaccatta    4980
acttccagga cggtccgcac tccgccacaa gtctcagcac gagccgcact cgatcttcct    5040
cccgttgcac ctatgccttc tgtacctgca ccggttagcc tgacgcctac gaggcgtgca    5100
ccaccaccgc cccttaccaa acgacccgtt gtcgtacgtc cgtcgacgcc tccaccgccg    5160
ccaccagtac gccagacacc aacgccagtg ctcgcgccac ggactggttc tacggcagca    5220
cccactccga cgccacgcct ctcgttatct acggaccagc catccgtaga catttcgttc    5280
ggagactttt cccccgcaga aacgatgtct ttgatgctgt cgtcccctgg ctctgacacc    5340
gccagtatca ccttcggtga cttcgacgag gacgaggtag aatctatagt aggacgggaa    5400
tattgactaa ccggagcggg agggtacata ttttcttcag acaccggcag tgggcattta    5460
caacaacgtt cggtccttca aaaccgcacg accgagacaa ttatagagcg agtcacacat    5520
gaccgcatcc acgccccaca gctcaatgaa gccagggaag aagttctgaa gttaaagtac    5580
caaatgtatc cctccgacgc taacaaaagt aggtaccgcg cccgcaaagt agagaaccaa    5640
aaagccatat gcatcagccg cctcacggca ggtagccgca gttattcttt cggaacaaca    5700
gaagccgaat gctacagaga aacttaccct gcagtcatgt actcgtcttc gctaccatcc    5760
tcctactcgg cgccgaccac ggctgtggct gtgtgcaacg cgtatctggc agctaattac    5820
cccaccgtcg cctcgtatca gatcactgac gagtacgacg cgtacttaga catggtcgac    5880
ggtactatgg cttgcttaga cacagcgtcc ttcaacccctt ctaaactaag gagttttccg    5940
aaggtccaca gtatctggaa acctactatc cgtagtgcag taccatctcc cttccagaat    6000
acactacaaa acgttctaac tgccgccact aagcgtaact gtaacgtcac ccaaatgcgc    6060
gagctaccga cactcgattc tgccgcattt aacgtagagt gctttaggaa atacgcctgc    6120
aacaacgact actggcaaga atatgcggat aaacctatcc gcataactac ggaatacgtc    6180
accgcctacg ttgccaagct aaagggacct aaagctgccg ccttgttttc caaaacacac    6240
gacttaccgg cgctcggcga agtacctatg gaccgcttcg tcatggacat gaagagagac    6300
gttaaagtga cccctggcag taagcacacc gaagaacgcc cgaaagttca ggtaattcaa    6360
gcagctgaac ctctgccacc tgcctactta tgcggcatcc atcgtgaact ggtccggcga    6420
ctcactgctg cgctccttcc caacatccac actctttttg acatgtccgc agaggacttc    6480
gacgccacac tggcccacca cttcaaaaag ggcgaccccg tactggaaac agacatagca    6540
tccttcgaca aaagtcagga tgacgcctta gcactcacag ggctaatgat cctggaggac    6600
ctaggagtag accagcccct catggacctg atcgaggcag ctttcggaga tataaccagc    6660
```

```
acgcacctac ccaccggagc acgtttccgg tttggcgcca tgatgaagtc tggtatgttt   6720
cttaccctgt tcatcaacac cgtccttaac gtggtaatag ccagccgtgt attagaagac   6780
aagttaacgc actccgcctg cgccgcattc atcggcgacg acaacatcat acacggagtc   6840
atatctgacc gtataatggc tgaccgatgc gctacatgga tgaatatgga agtcaaaatt   6900
atagacgcgg tcatgggaga ctaccctccc tatttctgtg gcgggttcct catcatagac   6960
agcgtgacca acaccgcatg ccgagtcgcc gaccccctga agagactatt caaacttggg   7020
aagccgctta ccgcggacga cgaccacgac gatgaccgga gaagagccct cgaggatgaa   7080
actaaagcat ggtttcgggt agggatcaga gaaggcatca ccgccgccgt atcatcaaga   7140
tacgaagtcg acaacatact gcccgttctc ttagccctta gaacctttgc tttatctacg   7200
cgcaacttct ctgccttacg gggaacactt aagaccctct acaactaa               7248

<210> SEQ ID NO 3
<211> LENGTH: 2414
<212> TYPE: PRT
<213> ORGANISM: Eilat virus
<400> SEQUENCE: 3

Met Glu Lys Pro Thr Val Asn Val Asp Val Asp Pro Gln Ser Pro Phe
1               5                   10                  15

Val Leu Gln Leu Gln Lys His Phe Pro Gln Phe Glu Ile Val Ala Asn
            20                  25                  30

Met Val Thr Pro Asn Asp His Ala Asn Ala Arg Ala Phe Ser His Cys
        35                  40                  45

Ala Ser Lys Leu Ile Glu Ala Glu Val Pro Val Thr Thr Pro Ile Ile
    50                  55                  60

Asp Ile Gly Ser Ala Pro Ala Arg Arg Met Tyr Ser Glu His Arg Tyr
65                  70                  75                  80

His Cys Val Cys Pro Met Lys Cys Pro Glu Asp Pro Asp Arg Leu Thr
                85                  90                  95

Thr Tyr Ala Asn Arg Leu Val Glu Asn Ala Thr Lys Ile Ala Asn Lys
            100                 105                 110

Arg Leu Asp Ala Lys Leu Gln Asp Leu Lys Gln Val Leu Glu Thr Pro
        115                 120                 125

Asp Ile Glu Thr Asp Ser Ile Cys Phe His Asp Asp Ala Thr Cys Arg
    130                 135                 140

Trp Val Ala Glu Val Ser Val Met Gln Asp Val Tyr Ile Asp Ala Pro
145                 150                 155                 160

Ser Ser Ile Tyr His Gln Ala Leu Lys Gly Ile Arg Lys Ile Tyr Trp
                165                 170                 175

Ile Gly Phe Asp Thr Thr Pro Phe Met Phe Lys Ala Leu Ala Gly Ser
            180                 185                 190

Tyr Pro Ser Tyr Asn Thr Asn Trp Ala Asp Glu Lys Val Leu Glu Ala
        195                 200                 205

Arg Asn Ile Gly Leu Cys Ser Thr Thr Leu Ser Glu Gly Ser Thr Gly
    210                 215                 220

Lys Leu Ser Ile Met Arg Lys Lys Arg Leu Leu Pro Gly Ala Gln Val
225                 230                 235                 240

Tyr Phe Ser Val Gly Ser Thr Leu Tyr Pro Glu Asn Arg Ser Asn Leu
                245                 250                 255

Met Ser Trp His Leu Pro Ser Val Phe His Leu Lys Gly Arg Asn Ala
            260                 265                 270
```

```
Phe Thr Cys Arg Cys Asp Thr Val Asn Cys Asp Gly Tyr Val Val
            275                 280                 285
Lys Lys Ile Thr Ile Ser Pro Asn Leu Ile Gly Thr Pro Ala Gly Tyr
290                     295                 300
Ala Val Thr Asn Asn Ser Glu Gly Phe Leu Leu Cys Lys Val Thr Asp
305                 310                 315                 320
Thr Val Arg Gly Glu Arg Val Ser Phe Pro Val Cys Met Ser Ile Pro
                325                 330                 335
Ala Thr Ile Cys Asp Gln Met Thr Gly Ile Leu Ala Thr Asp Ile Asn
            340                 345                 350
Pro Glu Asp Ala Gln Lys Leu Leu Val Gly Leu Asn Gln Arg Ile Val
        355                 360                 365
Val Asn Gly Lys Thr Asn Arg Asn Val Asn Thr Met Gln Asn His Leu
370                 375                 380
Leu Pro Ala Val Ala Gln Gly Phe Ser Lys Trp Ala Lys Glu Arg Lys
385                 390                 395                 400
Ala Asp Gly Asp Glu Lys His Leu Gly Thr Arg Glu Arg Ser Leu
                405                 410                 415
Thr Phe Gly Cys Leu Trp Ala Phe Arg Thr Lys Lys Val His Ser Phe
            420                 425                 430
Tyr Arg Pro Pro Gly Thr Gln Thr Ile Val Lys Val Glu Ser Val Phe
        435                 440                 445
Thr Ala Ser Pro Leu Ala Ile Pro Ile Arg Gln Thr Ser Leu Pro Ile
        450                 455                 460
Ser Leu Arg Leu Lys Leu Lys Met Ala Ile Ala Lys Lys Gln Asn Asn
465                 470                 475                 480
Pro Ile Ala Thr Ile Thr Gln Thr Gln Ile Thr Asn Ala Ile Glu Phe
                485                 490                 495
Gln Lys Glu Ala Thr Glu Thr Ala Arg Ala Val Glu Leu Asn Asn Ala
            500                 505                 510
Leu Pro Pro Leu Arg Ala Thr Glu Gln Asp Pro Thr Pro Ser Val Glu
        515                 520                 525
His Val Val Cys Glu Val Glu Glu Leu Ser Asp Asp Ile Gly Gly Ala
530                 535                 540
Leu Val Glu Thr Pro Arg Gly His Val Arg Ile Leu Pro Gln Pro Thr
545                 550                 555                 560
Asp Val Lys Val Gly Asn Tyr Leu Val Ile Ser Pro Gln Ala Val Leu
                565                 570                 575
Arg Asn Asp Lys Leu Ser Arg Leu His Pro Leu Ala Glu Gln Ile Lys
            580                 585                 590
Val Ile Thr His Thr Gly Arg Lys Gly Arg Tyr Glu Val Ala Pro Tyr
        595                 600                 605
Ser Gly Lys Met Leu Leu Pro Cys Gly Thr Ser Val Pro Trp Pro Gln
        610                 615                 620
Phe Cys Ala Leu Ala Glu Ser Ala Thr Leu Val Phe Asn Glu Arg Glu
625                 630                 635                 640
Met Ile Asp Arg Lys Leu Ala Tyr Ile Ala Gln His Gly Pro Ala Leu
                645                 650                 655
Asn Thr Asp Glu Glu Gln Tyr Lys Val Ile Lys Ala Ser Ala Ala Asp
            660                 665                 670
Ser Glu Tyr Val Phe Asp Ile Asp Arg Met Arg Cys Val Pro Thr Lys
        675                 680                 685
Glu Ala Asn Gly Leu Val Leu Val Gly Glu Leu Thr Gln Pro Pro Tyr
```

```
               690                 695                 700

His Glu Leu Ala Met Gln Gly Leu Tyr Thr Arg Pro Ala Ala Pro Tyr
705                 710                 715                 720

Pro Ile Glu Thr Ile Gly Val Ile Gly Thr Pro Gly Ser Gly Lys Ser
                725                 730                 735

Ala Ile Ile Lys Asn Thr Val Thr Thr Lys Asp Leu Val Thr Ser Gly
                740                 745                 750

Lys Lys Glu Asn Cys Lys Glu Ile Glu Thr Asp Val Leu Arg Leu Arg
                755                 760                 765

Asn Leu Val Ile Lys Ser Arg Thr Val Asp Ser Val Leu Leu Asn Gly
                770                 775                 780

Cys Thr Gln Glu Val Asp Val Leu His Val Asp Glu Ala Phe Ala Cys
785                 790                 795                 800

His Ala Gly Thr Leu Leu Ala Leu Ile Ala Ile Val Lys Pro Arg Cys
                805                 810                 815

Lys Val Val Leu Tyr Gly Asp Pro Lys Gln Cys Gly Phe Phe Asn Leu
                820                 825                 830

Met Gln Ile Lys Val His Phe Asn Asn Pro Glu Val Asp Val Cys Ser
                835                 840                 845

Gln Leu His Tyr Lys Tyr Ile Ser Arg Arg Cys Ile Leu Pro Val Thr
                850                 855                 860

Ala Ile Val Ser Ser Ile His Tyr Asp Gly Lys Met Arg Thr Thr Asn
865                 870                 875                 880

Thr Ala Asp Gln Arg Ile Glu Ile Asp Thr Thr Gly Thr Ser Lys Pro
                885                 890                 895

Lys Pro Thr Asp Leu Ile Leu Thr Cys Phe Arg Gly Trp Val Lys Gln
                900                 905                 910

Leu Gln Leu Glu Tyr Pro Arg Asn Glu Val Met Thr Ala Ala Ala Ser
                915                 920                 925

Gln Gly Leu Thr Arg Lys Arg Val Tyr Ala Val Arg Tyr Lys Val Asn
                930                 935                 940

Glu Asn Pro Leu Tyr Ala Phe Thr Ser Glu His Val Asn Val Leu Leu
945                 950                 955                 960

Thr Arg Thr Glu His Thr Leu Val Trp Lys Thr Leu Gln Gly Asp Pro
                965                 970                 975

Trp Ile Lys His Leu Ser Asn Val Pro Lys Gly Asn Phe Ser Ala Thr
                980                 985                 990

Val Asp Glu Trp His Ala Glu His Glu Arg Ile Met Asn Ala Ile Arg
                995                 1000                1005

Met Pro Thr Pro Glu Val Asn Ala Phe Ser Cys Lys Thr Asn Val
    1010                1015                1020

Cys Trp Ala Lys Ala Leu Val Pro Val Leu Ala Thr Ala Gly Leu
    1025                1030                1035

Lys Leu Ser Gly Ala Gln Trp Thr Glu Leu Phe Pro Gln Phe Glu
    1040                1045                1050

Arg Asp Glu Pro His Ser Ala Thr Phe Ala Leu Asp Val Leu Cys
    1055                1060                1065

Ile Lys Tyr Phe Gly Met Asp Leu Thr Ser Gly Ile Phe Ala Lys
    1070                1075                1080

Pro Thr Val Pro Leu Thr His Pro Val Ser Arg Tyr His Pro
    1085                1090                1095

Gln Ala His Trp Asp Asn Ala Asn Gly Glu Gln Arg Tyr Gly Phe
    1100                1105                1110
```

```
Asp Pro Asp Ile Ala Lys Ala Leu Ala Arg Arg Phe Pro Val Phe
1115                1120                1125

Ser Gln Ala Ala Lys Gly His Ala Ile Ser Pro Ile Leu Gly Thr
1130                1135                1140

Thr His Thr Leu Ser Ser Arg Asp Asn Tyr Val Pro Val Asn Arg
1145                1150                1155

Ile Val Pro His Thr Leu Lys Gly Glu Tyr Thr Tyr Val Lys Gln
1160                1165                1170

Asp Ser Leu Ala Ser Val Leu Ser Ala Val Gln Ala Phe Ser Val
1175                1180                1185

Leu Val Val Ser Ser Glu Pro Ile Ala Ser Ala Thr Lys Gln Ile
1190                1195                1200

Thr Trp Val Ala Pro Leu Gly Thr Ala Gly Cys Ile His Thr His
1205                1210                1215

Arg Leu Pro Trp Gly Phe Pro Lys Met Ser Leu His Asp Ala Val
1220                1225                1230

Ala Val Asn Met Glu Thr Glu Tyr Arg Gly His His Tyr Gln Gln
1235                1240                1245

Cys Glu Asp His Val Ala Ile Leu Lys Thr Leu Gly Lys Ser Ala
1250                1255                1260

Leu Ala Asn Leu Arg Pro Gly Gly Thr Leu Ile Leu Arg Thr Tyr
1265                1270                1275

Gly Tyr Ala Asp Arg Asn Ser Glu Asn Val Ile Thr Ala Leu Ala
1280                1285                1290

Arg Lys Phe Ala Arg Val Thr Ala Val Arg Ser Ser Asn Pro Ser
1295                1300                1305

Ser Asn Thr Glu Ile Tyr Leu Ile Phe Arg Lys Phe Asp Asn Asn
1310                1315                1320

Arg Ser Arg Gln Phe Thr Leu His His Leu Asn Arg Ala Ile Ser
1325                1330                1335

Ala Leu Tyr Glu Ser Pro Cys Asp Pro Asp Gly Val Gly Ala Ala
1340                1345                1350

Pro Ser Tyr Ser Val Ile Arg Gly Asp Ile Thr Ala Thr Asn Ser
1355                1360                1365

His Ala Ile Val Val Pro Val Thr Pro Glu Arg Lys Asp Gly Val
1370                1375                1380

Tyr Arg Ala Cys Ser Lys Lys Trp Gly Pro Leu Pro Arg Leu Glu
1385                1390                1395

Trp Thr Glu Gly Ala Thr Leu Phe Ser Pro Gly Ser Pro Ala Thr
1400                1405                1410

Leu Gln Val Cys Val Pro Ser Leu Gln Asn Thr Asp Thr Thr Ser
1415                1420                1425

Thr Gln Gln Ala Tyr Arg Ala Ile Ala Lys Val Val Asp Glu
1430                1435                1440

Gln Ile Pro Ser Leu Ser Leu Pro Val Leu Thr Met Lys Lys Thr
1445                1450                1455

Gly Thr Ala Asp Thr Val Ser Glu Ser Leu Asn His Leu Val Thr
1460                1465                1470

Ala Leu Asp Gln Thr Asp Ala Asn Val Thr Ile Tyr Cys Leu Asp
1475                1480                1485

Lys Ser Arg Leu Ile Lys Ile Lys Glu Val Ile Ala Arg Lys Glu
1490                1495                1500
```

```
Ala Val Thr Glu Leu Ile Asp Asp Leu Glu Ile Asp Glu Glu
    1505                1510                1515

Leu Thr Trp Val His Pro Asp Ser Cys Leu Arg Asn Arg Thr Gly
    1520                1525                1530

Phe Ser Thr Asp Lys Gly Lys Leu Tyr Ser Tyr Leu Glu Gly Thr
    1535                1540                1545

Lys Phe His Gln Met Ala Lys Asp Phe Ala Glu Ile Arg Ser Leu
    1550                1555                1560

Phe Pro Asp Glu Met Glu Ala Asn Glu His Ile Cys Ser Leu Ile
    1565                1570                1575

Leu Gly Glu Thr Ile Asp Gly Ile Arg Glu Arg Cys Pro Val Thr
    1580                1585                1590

Asp Asn Pro Pro Ser Ser Pro Pro Lys Thr Val Pro Cys Leu Cys
    1595                1600                1605

Met Tyr Ala Met Thr Pro Glu Arg Ala Leu Arg Leu Lys Ser Asn
    1610                1615                1620

Ser Val Thr Gln Ile Thr Val Cys Ser Ser Phe Val Leu Lys Lys
    1625                1630                1635

His His Ile Lys Gly Val Gln Lys Ile Gln Cys Thr Ala Pro Met
    1640                1645                1650

Leu Phe Asn Pro Thr Pro Leu Thr Ser Arg Thr Val Arg Thr Pro
    1655                1660                1665

Pro Gln Val Ser Ala Arg Ala Ala Leu Asp Leu Pro Pro Val Ala
    1670                1675                1680

Pro Met Pro Ser Val Pro Ala Pro Val Ser Leu Thr Pro Thr Arg
    1685                1690                1695

Arg Ala Pro Pro Pro Pro Leu Thr Lys Arg Pro Val Val Val Arg
    1700                1705                1710

Pro Ser Thr Pro Pro Pro Pro Pro Val Arg Gln Thr Pro Thr
    1715                1720                1725

Pro Val Leu Ala Pro Arg Thr Gly Ser Thr Ala Ala Pro Thr Pro
    1730                1735                1740

Thr Pro Arg Leu Ser Leu Ser Thr Asp Gln Pro Ser Val Asp Ile
    1745                1750                1755

Ser Phe Gly Asp Phe Ser Pro Ala Glu Thr Met Ser Leu Met Leu
    1760                1765                1770

Ser Ser Pro Gly Ser Asp Thr Ala Ser Ile Thr Phe Gly Asp Phe
    1775                1780                1785

Asp Glu Asp Glu Val Glu Ser Ile Val Gly Arg Glu Tyr Leu Thr
    1790                1795                1800

Gly Ala Gly Gly Tyr Ile Phe Ser Ser Asp Thr Gly Ser Gly His
    1805                1810                1815

Leu Gln Gln Arg Ser Val Leu Gln Asn Arg Thr Thr Glu Thr Ile
    1820                1825                1830

Ile Glu Arg Val Thr His Asp Arg Ile His Ala Pro Gln Leu Asn
    1835                1840                1845

Glu Ala Arg Glu Glu Val Leu Lys Leu Lys Tyr Gln Met Tyr Pro
    1850                1855                1860

Ser Asp Ala Asn Lys Ser Arg Tyr Arg Ala Arg Lys Val Glu Asn
    1865                1870                1875

Gln Lys Ala Ile Cys Ile Ser Arg Leu Thr Ala Gly Ser Arg Ser
    1880                1885                1890

Tyr Ser Phe Gly Thr Thr Glu Ala Glu Cys Tyr Arg Glu Thr Tyr
```

-continued

```
              1895                1900                1905
Pro Ala Val Met Tyr Ser Ser Leu Pro Ser Ser Tyr Ser Ala
        1910                1915                1920

Pro Thr Thr Ala Val Ala Val Cys Asn Ala Tyr Leu Ala Ala Asn
        1925                1930                1935

Tyr Pro Thr Val Ala Ser Tyr Gln Ile Thr Asp Glu Tyr Asp Ala
        1940                1945                1950

Tyr Leu Asp Met Val Asp Gly Thr Met Ala Cys Leu Asp Thr Ala
        1955                1960                1965

Ser Phe Asn Pro Ser Lys Leu Arg Ser Phe Pro Lys Val His Lys
        1970                1975                1980

Tyr Leu Glu Pro Thr Ile Arg Ser Ala Val Pro Ser Pro Phe Gln
        1985                1990                1995

Asn Thr Leu Gln Asn Val Leu Thr Ala Ala Thr Lys Arg Asn Cys
        2000                2005                2010

Asn Val Thr Gln Met Arg Glu Leu Pro Thr Leu Asp Ser Ala Ala
        2015                2020                2025

Phe Asn Val Glu Cys Phe Arg Lys Tyr Ala Cys Asn Asn Asp Tyr
        2030                2035                2040

Trp Gln Glu Tyr Ala Asp Lys Pro Ile Arg Ile Thr Thr Glu Tyr
        2045                2050                2055

Val Thr Ala Tyr Val Ala Lys Leu Lys Gly Pro Lys Ala Ala Ala
        2060                2065                2070

Leu Phe Ser Lys Thr His Asp Leu Pro Ala Leu Gly Glu Val Pro
        2075                2080                2085

Met Asp Arg Phe Val Met Asp Met Lys Arg Asp Val Lys Val Thr
        2090                2095                2100

Pro Gly Ser Lys His Thr Glu Glu Arg Pro Lys Val Gln Val Ile
        2105                2110                2115

Gln Ala Ala Glu Pro Leu Ala Thr Ala Tyr Leu Cys Gly Ile His
        2120                2125                2130

Arg Glu Leu Val Arg Arg Leu Thr Ala Ala Leu Leu Pro Asn Ile
        2135                2140                2145

His Thr Leu Phe Asp Met Ser Ala Glu Asp Phe Asp Ala Thr Leu
        2150                2155                2160

Ala His His Phe Lys Lys Gly Asp Pro Val Leu Glu Thr Asp Ile
        2165                2170                2175

Ala Ser Phe Asp Lys Ser Gln Asp Asp Ala Leu Ala Leu Thr Gly
        2180                2185                2190

Leu Met Ile Leu Glu Asp Leu Gly Val Asp Gln Pro Leu Met Asp
        2195                2200                2205

Leu Ile Glu Ala Ala Phe Gly Asp Ile Thr Ser Thr His Leu Pro
        2210                2215                2220

Thr Gly Ala Arg Phe Arg Phe Gly Ala Met Met Lys Ser Gly Met
        2225                2230                2235

Phe Leu Thr Leu Phe Ile Asn Thr Val Leu Asn Val Val Ile Ala
        2240                2245                2250

Ser Arg Val Leu Glu Asp Lys Leu Thr His Ser Ala Cys Ala Ala
        2255                2260                2265

Phe Ile Gly Asp Asp Asn Ile Ile His Gly Val Ile Ser Asp Arg
        2270                2275                2280

Ile Met Ala Asp Arg Cys Ala Thr Trp Met Asn Met Glu Val Lys
        2285                2290                2295
```

```
Ile Ile  Asp Ala Val Met Gly  Asp Tyr Pro Pro Tyr  Phe Cys Gly
    2300                 2305                 2310

Gly Phe  Leu Ile Ile Asp Ser  Val Thr Asn Thr Ala  Cys Arg Val
    2315                 2320                 2325

Ala Asp  Pro Leu Lys Arg Leu  Phe Lys Leu Gly Lys  Pro Leu Thr
    2330                 2335                 2340

Ala Asp  Asp Asp His Asp Asp  Asp Arg Arg Arg Ala  Leu Glu Asp
    2345                 2350                 2355

Glu Thr  Lys Ala Trp Phe Arg  Val Gly Ile Arg Glu  Gly Ile Thr
    2360                 2365                 2370

Ala Ala  Val Ser Ser Arg Tyr  Glu Val Asp Asn Ile  Leu Pro Val
    2375                 2380                 2385

Leu Leu  Ala Leu Arg Thr Phe  Ala Leu Ser Thr Arg  Asn Phe Ser
    2390                 2395                 2400

Ala Leu  Arg Gly Thr Leu Lys  Thr Leu Tyr Asn
    2405                 2410
```

<210> SEQ ID NO 4
<211> LENGTH: 3702
<212> TYPE: DNA
<213> ORGANISM: Eilat virus

<400> SEQUENCE: 4

```
atgttccgca ccaataacaa ccgccaacgt cgtcaacagc cacgctcccg caggcaacgt     60
tcaccctcgc ggcccctgca gcgccgacaa gacgatgcac tctccaaaca ggtccgcgcc    120
ctaactaccg cagttcagaa actagtggtg gcaggaaatc gccgcccacc gccttccccc    180
cgagccaagg cgcctggacc agcccaacca cgaccagcta aagcgcccgt caaaactcca    240
gccaagagag gaccagcccc taagcgtaaa cccggaaaga gagaacgtac cgcgctccgc    300
ctgcaggcag accgagtctt ccccgtcgtt aatgacaaac aagtcacggt cggctatgct    360
gtagcgctgg aagggcgtgt catgaagcct ttgcacgtca agggcactat tgaccaccct    420
ctccttgcct cactcaagtt taccaaatcc acgtccttcg acatggagta cgccgctcta    480
ccaaccacca tgcgctctga agcctttgct tacaccagcg agcacccaga cgggttctac    540
agctgggtcc atggcgccgt acagtgcacc aacgggcgct tctccatccc tacaggggca    600
ggaggccctg gcgacagcgg caggccaatc ctcgacaaca caggcaaagt cgtagccctt    660
gtccttggag gtgcaaatga aggcactcgc acgtctctct cggtagtcac gtggaacaag    720
tcaggcaccg cagccaagac cacacccgac gacacagtgg agtggtccgc catcgtgacc    780
gcactttgcg tactcggcaa cgcctccttc acttgcaccg agccaccgat ttgcttcgac    840
acccatccag gagacaccct cggcatgctc gaggacaacg tcgaccaccc catgtactat    900
gaccttatgt acgccgccct actatgtaac caccagcaaa aacgagcccg tagagccgtc    960
gccccgaaac cggacgaata tcgccttgcg tctccctacg tggggcgatg cgcagcatgc   1020
tcaaacggca tcacctgctt cagccccatc aagcttgaat ccgtatggac aacaccacac   1080
agctcggtcc taaaaatgca actatcggta cttttcggta tagacgaaac aggcaaattg   1140
gacaacacag tcctcagtta catgtccccg acggagcata cggtgaaaag catgccgatc   1200
acggcactaa ccgcatccac aaccggacca tgtatcatca cggccacacg aggctatttc   1260
gcgctggcac agtgcccacc aggtgacgtg ctcactgtag caatgggctc tcatcactgc   1320
tccattgagt ccgagcacct cagaccctca gtgggtcgcg aagaattcgc ctctacaccg   1380
```

```
ctccacggcg tccggcgccc gtgctctacc tatgacgccg ccaaatacac cagcacttct    1440
gaaatgaccc tccaccgcgc caaaccgcag gcctcagact cactcctgtc tatcgtaaac    1500
gacactgtcc aaatcaccgt gtcgtccaac ctgaccgtca gttacgagtg cctctgcgac    1560
ggctaccact ccggcttcgt acgtgcaaca acacttatcc ctggatgcac taataccaac    1620
caatgcattg catccgtaaa cgacaagacg cgctggtatc ccaacacgga cgacttcatc    1680
agacacaccg accacagccc cagaggtaaa atcaacgttc ctttcccgct agaggcaggt    1740
gaatgcctgg tcccgctagc ccgctcccca gctatccggt actcccgaaa tgaggtggag    1800
ctcacactgg tcacgacccg taaggccctt ttgtccacac ggcaactcgg ctccgaacca    1860
aacgcaacct ctgagtggat cacatcctcc actcgtcgga ccttttactt gcctgccgca    1920
gggctagagt tcacttgggg taacaacgac cccgtccgcg tttggcctca agcctcagcc    1980
gacggggatg cgcacggtct cccacacgaa atcgttgcgt actattacag caggtcccct    2040
ctcttcacca tcgtggccgt caccctttatc tctgcaatcg tgctcgcctc gctggccttc    2100
tgttgctgca agtggacctc tttccgatcc gcactccgct cgccatacgc cctggcaccg    2160
aacgcaaccg tacccatgtg tctcacattg ctgtgctgca tccgtcaagc aaaagcagac    2220
acatacttcg acgccgccag ctatctctgg aacaactacc agccgctatt ctgggcacag    2280
ttggcgatac caaccgcctc cattttttgtg ctctttaaat gctgctcact cgccgtggct    2340
tttttagctg ttgtgggcgc atcgcttccc ctagcaagcg cccacgaaca tgcggccaat    2400
gttcccaact ctccactctt gtcgtataaa gccgtcgtta cacgccctgg atatacaccc    2460
cttgccctag aaattcgggt tttggaaaac cgtatccaac cgacaacact cacccactat    2520
tacacttgct cctaccgcac cgtagtcccg tcgcctacgg tcaaatgctg tggtagtttg    2580
cagtgcggtt cttccagtct acccgattac cgctgcaagg tgttcaccgg agtatacccca    2640
tttatgtggg gaggggccca gtgtttctgc gatactgaga actcccaaat gagtgagagt    2700
tacgtcgaca aggacccgtc ctgccctacc gaccacgcgg aagcggtagc cacccagaac    2760
cccgtggtac gcgccacact acagatcact ataggcaacg ccactactcg caccgacgtg    2820
tacgttaacg gcgtttcacc gagctacact aatggagcga aagtcattgc cgggccgctc    2880
tcctctgtat ggagtccttt cgcagacaag gtggtcatct accagaggcg cgtttacaat    2940
cacgcgttcc ccgaatatgg tgccggcact cctggcactt tcggcgacct ccaactcccc    3000
agccttcgcg ccaaggactt tttcgccaac accgggctag tcctcaatcg acccgacact    3060
tcttcgctgc acgtgccgta cacacaagta ccgagcgggt ttgtcacctg gagagaccag    3120
cacttgcctg atcttcaaca aaccgctcca tatggctgcg ccatttcaag cagtccgctg    3180
caggcaatta attgctcgta cggcagtatc cctgtgtcca tcgacattcc cgacgcctcc    3240
ttcacccgct ccttcgacgc accatccgtt tcttcactga aatgcactcc tattgagtgc    3300
gtccactcgg ccgggtacgg aggccttctc agactagact acgtcgccga caaggccggc    3360
acttgcagtc ttcattcgca cagtgatgcc gtccttatga aggattcact cctcagcatt    3420
aacgcaacgg gatcctacac aggtcttttc tcgacggcca gcccccaagt caagttcacc    3480
atcaccctgt gctcggcgga ggtcagctgc gagactgcgc gcaagccacc actcgaacac    3540
gcctcatcac acccgcacct gacgtcacag actttcgact ccgctatatc aacatccgcc    3600
tggacatggt tgctcagcct attcggaggg tcaatatcac ttgtgaccgt aggcatcttt    3660
attgcggcag cctgtacat cgtcaattgc agacgtcgct aa    3702
```

<210> SEQ ID NO 5
<211> LENGTH: 1233
<212> TYPE: PRT
<213> ORGANISM: Eilat virus

<400> SEQUENCE: 5

```
Met Phe Arg Thr Asn Asn Asn Arg Gln Arg Arg Gln Gln Pro Arg Ser
1               5                   10                  15

Arg Arg Gln Arg Ser Pro Ser Arg Pro Leu Gln Arg Arg Gln Asp Asp
            20                  25                  30

Ala Leu Ser Lys Gln Val Arg Ala Leu Thr Thr Ala Val Gln Lys Leu
        35                  40                  45

Val Val Ala Gly Asn Arg Arg Pro Pro Pro Ser Pro Arg Ala Lys Ala
    50                  55                  60

Pro Gly Pro Ala Gln Pro Arg Pro Ala Lys Ala Pro Val Lys Thr Pro
65                  70                  75                  80

Ala Lys Arg Gly Pro Ala Pro Lys Arg Lys Pro Gly Lys Arg Glu Arg
                85                  90                  95

Thr Ala Leu Arg Leu Gln Ala Asp Arg Val Phe Pro Val Val Asn Asp
            100                 105                 110

Lys Gln Val Thr Val Gly Tyr Ala Val Ala Leu Glu Gly Arg Val Met
        115                 120                 125

Lys Pro Leu His Val Lys Gly Thr Ile Asp His Pro Leu Leu Ala Ser
    130                 135                 140

Leu Lys Phe Thr Lys Ser Thr Ser Phe Asp Met Glu Tyr Ala Ala Leu
145                 150                 155                 160

Pro Thr Thr Met Arg Ser Glu Ala Phe Ala Tyr Thr Ser Glu His Pro
                165                 170                 175

Asp Gly Phe Tyr Ser Trp Val His Gly Ala Val Gln Cys Thr Asn Gly
            180                 185                 190

Arg Phe Ser Ile Pro Thr Gly Ala Gly Gly Pro Gly Asp Ser Gly Arg
        195                 200                 205

Pro Ile Leu Asp Asn Thr Gly Lys Val Val Ala Leu Val Leu Gly Gly
    210                 215                 220

Ala Asn Glu Gly Thr Arg Thr Ser Leu Ser Val Val Thr Trp Asn Lys
225                 230                 235                 240

Ser Gly Thr Ala Ala Lys Thr Thr Pro Asp Asp Thr Val Glu Trp Ser
                245                 250                 255

Ala Ile Val Thr Ala Leu Cys Val Leu Gly Asn Ala Ser Phe Thr Cys
            260                 265                 270

Thr Glu Pro Pro Ile Cys Phe Asp Thr His Pro Gly Asp Thr Leu Gly
        275                 280                 285

Met Leu Glu Asp Asn Val Asp His Pro Met Tyr Tyr Asp Leu Met Tyr
    290                 295                 300

Ala Ala Leu Leu Cys Asn His Gln Gln Lys Arg Ala Arg Arg Ala Val
305                 310                 315                 320

Ala Pro Lys Pro Asp Glu Tyr Arg Leu Ala Ser Pro Tyr Val Gly Arg
                325                 330                 335

Cys Ala Ala Cys Ser Asn Gly Ile Thr Cys Phe Ser Pro Ile Lys Leu
            340                 345                 350

Glu Ser Val Trp Thr Thr Pro His Ser Ser Val Leu Lys Met Gln Leu
        355                 360                 365

Ser Val Leu Phe Gly Ile Asp Glu Thr Gly Lys Leu Asp Asn Thr Val
    370                 375                 380
```

```
Leu Ser Tyr Met Ser Pro Thr Glu His Thr Val Lys Ser Met Pro Ile
385                 390                 395                 400

Thr Ala Leu Thr Ala Ser Thr Thr Gly Pro Cys Ile Ile Thr Ala Thr
                405                 410                 415

Arg Gly Tyr Phe Ala Leu Ala Gln Cys Pro Pro Gly Asp Val Leu Thr
            420                 425                 430

Val Ala Met Gly Ser His His Cys Ser Ile Glu Ser Glu His Leu Arg
        435                 440                 445

Pro Ser Val Gly Arg Glu Glu Phe Ala Ser Thr Pro Leu His Gly Val
    450                 455                 460

Arg Arg Pro Cys Ser Thr Tyr Asp Ala Ala Lys Tyr Thr Ser Thr Ser
465                 470                 475                 480

Glu Met Thr Leu His Arg Ala Lys Pro Gln Ala Ser Asp Ser Leu Leu
                485                 490                 495

Ser Ile Val Asn Asp Thr Val Gln Ile Thr Val Ser Ser Asn Leu Thr
                500                 505                 510

Val Ser Tyr Glu Cys Leu Cys Asp Gly Tyr His Ser Gly Phe Val Arg
        515                 520                 525

Ala Thr Thr Leu Ile Pro Gly Cys Thr Asn Thr Asn Gln Cys Ile Ala
    530                 535                 540

Ser Val Asn Asp Lys Thr Arg Trp Tyr Pro Asn Thr Asp Asp Phe Ile
545                 550                 555                 560

Arg His Thr Asp His Ser Pro Arg Gly Lys Ile Asn Val Pro Phe Pro
                565                 570                 575

Leu Glu Ala Gly Glu Cys Leu Val Pro Leu Ala Arg Ser Pro Ala Ile
                580                 585                 590

Arg Tyr Ser Arg Asn Glu Val Glu Leu Thr Leu Val Thr Thr Arg Lys
        595                 600                 605

Ala Leu Leu Ser Thr Arg Gln Leu Gly Ser Glu Pro Asn Ala Thr Ser
    610                 615                 620

Glu Trp Ile Thr Ser Ser Thr Arg Arg Thr Phe Tyr Leu Pro Ala Ala
625                 630                 635                 640

Gly Leu Glu Phe Thr Trp Gly Asn Asn Asp Pro Val Arg Val Trp Pro
                645                 650                 655

Gln Ala Ser Ala Asp Gly Asp Ala His Gly Leu Pro His Glu Ile Val
                660                 665                 670

Ala Tyr Tyr Tyr Ser Arg Ser Pro Leu Phe Thr Ile Val Ala Val Thr
        675                 680                 685

Leu Ile Ser Ala Ile Val Leu Ala Ser Leu Ala Phe Cys Cys Cys Lys
    690                 695                 700

Trp Thr Ser Phe Arg Ser Ala Leu Arg Ser Pro Tyr Ala Leu Ala Pro
705                 710                 715                 720

Asn Ala Thr Val Pro Met Cys Leu Thr Leu Leu Cys Cys Ile Arg Gln
                725                 730                 735

Ala Lys Ala Asp Thr Tyr Phe Asp Ala Ala Ser Tyr Leu Trp Asn Asn
                740                 745                 750

Tyr Gln Pro Leu Phe Trp Ala Gln Leu Ala Ile Pro Thr Ala Ser Ile
        755                 760                 765

Phe Val Leu Phe Lys Cys Cys Ser Leu Ala Val Ala Phe Leu Ala Val
    770                 775                 780

Val Gly Ala Ser Leu Pro Leu Ala Ser Ala His Glu His Ala Ala Asn
785                 790                 795                 800

Val Pro Asn Ser Pro Leu Leu Ser Tyr Lys Ala Val Val Thr Arg Pro
```

```
                    805                 810                 815
Gly Tyr Thr Pro Leu Ala Leu Glu Ile Arg Val Leu Glu Asn Arg Ile
                820                 825                 830

Gln Pro Thr Thr Leu Thr His Tyr Tyr Thr Cys Ser Tyr Arg Thr Val
                835                 840                 845

Val Pro Ser Pro Thr Val Lys Cys Cys Gly Ser Leu Gln Cys Gly Ser
850                 855                 860

Ser Ser Leu Pro Asp Tyr Arg Cys Lys Val Phe Thr Gly Val Tyr Pro
865                 870                 875                 880

Phe Met Trp Gly Gly Ala Gln Cys Phe Cys Asp Thr Glu Asn Ser Gln
                885                 890                 895

Met Ser Glu Ser Tyr Val Asp Lys Asp Pro Ser Cys Pro Thr Asp His
                900                 905                 910

Ala Glu Ala Val Ala Thr Gln Asn Pro Val Val Arg Ala Thr Leu Gln
                915                 920                 925

Ile Thr Ile Gly Asn Ala Thr Thr Arg Thr Asp Val Tyr Val Asn Gly
                930                 935                 940

Val Ser Pro Ser Tyr Thr Asn Gly Ala Lys Val Ile Ala Gly Pro Leu
945                 950                 955                 960

Ser Ser Val Trp Ser Pro Phe Ala Asp Lys Val Val Ile Tyr Gln Arg
                965                 970                 975

Arg Val Tyr Asn His Ala Phe Pro Glu Tyr Gly Ala Gly Thr Pro Gly
                980                 985                 990

Thr Phe Gly Asp Leu Gln Leu Pro  Ser Leu Arg Ala Lys  Asp Phe Phe
                995                 1000                1005

Ala Asn  Thr Gly Leu Val Leu  Asn Arg Pro Asp Thr  Ser Ser Leu
1010                1015                1020

His Val  Pro Tyr Thr Gln Val  Pro Ser Gly Phe Val  Thr Trp Arg
1025                1030                1035

Asp Gln  His Leu Pro Asp Leu  Gln Gln Thr Ala Pro  Tyr Gly Cys
1040                1045                1050

Ala Ile  Ser Ser Ser Pro Leu  Gln Ala Ile Asn Cys  Ser Tyr Gly
1055                1060                1065

Ser Ile  Pro Val Ser Ile Asp  Ile Pro Asp Ala Ser  Phe Thr Arg
1070                1075                1080

Ser Phe  Asp Ala Pro Ser Val  Ser Ser Leu Lys Cys  Thr Pro Ile
1085                1090                1095

Glu Cys  Val His Ser Ala Gly  Tyr Gly Gly Leu Leu  Arg Leu Asp
1100                1105                1110

Tyr Val  Ala Asp Lys Ala Gly  Thr Cys Ser Leu His  Ser His Ser
1115                1120                1125

Asp Ala  Val Leu Met Lys Asp  Ser Leu Leu Ser Ile  Asn Ala Thr
1130                1135                1140

Gly Ser  Tyr Thr Gly Leu Phe  Ser Thr Ala Ser Pro  Gln Val Lys
1145                1150                1155

Phe Thr  Ile Thr Leu Cys Ser  Ala Glu Val Ser Cys  Glu Thr Ala
1160                1165                1170

Cys Lys  Pro Pro Leu Glu His  Ala Ser Ser His Pro  His Leu Thr
1175                1180                1185

Ser Gln  Thr Phe Asp Ser Ala  Ile Ser Thr Ser Ala  Trp Thr Trp
1190                1195                1200

Leu Leu  Ser Leu Phe Gly Gly  Ser Ile Ser Leu Val  Thr Val Gly
1205                1210                1215
```

```
Ile Phe Ile Ala Ala Ala Leu Tyr Ile Val Asn Cys Arg Arg Arg
    1220            1225                1230
```

```
<210> SEQ ID NO 6
<211> LENGTH: 133
<212> TYPE: DNA
<213> ORGANISM: Eilat virus

<400> SEQUENCE: 6
cgcgcaactt ctctgcctta cggggaacac ttaagaccct ctacaactaa cctaaatagt      60
gcgcgtatta tcaatactac tagcacacta ttacccgtgt acgtaccaac ggcactactt     120
gcacaagtca aca                                                        133

<210> SEQ ID NO 7
<211> LENGTH: 51
<212> TYPE: RNA
<213> ORGANISM: Eilat virus

<400> SEQUENCE: 7 caugucacc ccgaaugacc acgccaaugc gagagccuuc ucccauugcg c                51

<210> SEQ ID NO 8
<211> LENGTH: 51
<212> TYPE: RNA
<213> ORGANISM: Trocara virus

<400> SEQUENCE: 8
gcaggucacu gccaaugacc augcuaaugc cagagcguuc ucgcaucugg c               51

<210> SEQ ID NO 9
<211> LENGTH: 51
<212> TYPE: RNA
<213> ORGANISM: Aura virus

<400> SEQUENCE: 9
gcaggucacu ccgaaugacc augcuaaugc cagagcuuuu ucgcaucugg c               51

<210> SEQ ID NO 10
<211> LENGTH: 51
<212> TYPE: RNA
<213> ORGANISM: Whataroa virus

<400> SEQUENCE: 10
gcaggccacg ccaaaugacc augcuaaugc cagagccuuu ucgcaucugg c               51

<210> SEQ ID NO 11
<211> LENGTH: 51
<212> TYPE: RNA
<213> ORGANISM: Sindbis virus

<400> SEQUENCE: 11
gcaggucacu ccaaaugacc augcuaaugc cagagcauuu ucgcaucugg c               51

<210> SEQ ID NO 12
<211> LENGTH: 51
<212> TYPE: RNA
<213> ORGANISM: Western equine encephalomyelitis virus

<400> SEQUENCE: 12
gcaggucacu gacaacgacc augcuaaugc cagagcauuu ucgcaugugg c               51
```

```
<210> SEQ ID NO 13
<211> LENGTH: 51
<212> TYPE: RNA
<213> ORGANISM: Eastern equine encephalomyelitis virus

<400> SEQUENCE: 13
gcaggucacu gacaaugacc augcuaaugc uagggcguuu ucgcaccuag c          51

<210> SEQ ID NO 14
<211> LENGTH: 51
<212> TYPE: RNA
<213> ORGANISM: Venezuelan equine encephalitis virus

<400> SEQUENCE: 14
gcaggucacu gauaaugacc augcuaaugc cagagcguuu ucgcaucugg c          51

<210> SEQ ID NO 15
<211> LENGTH: 51
<212> TYPE: RNA
<213> ORGANISM: Chikungunya virus

<400> SEQUENCE: 15
gcaggucaca ucgaaugacc augcuaaugc uagagcguuc ucgcaucuag c          51

<210> SEQ ID NO 16
<211> LENGTH: 51
<212> TYPE: RNA
<213> ORGANISM: Ross River virus

<400> SEQUENCE: 16
gcaggucaca ccuaaugacc augcuaaugc cagagccuuu ucgcaucugg c          51

<210> SEQ ID NO 17
<211> LENGTH: 51
<212> TYPE: RNA
<213> ORGANISM: Una virus

<400> SEQUENCE: 17
gcaggucacu ccaaaugacc augcgaacgc gagggcuuuc ucgcaccucg c          51

<210> SEQ ID NO 18
<211> LENGTH: 51
<212> TYPE: RNA
<213> ORGANISM: Semliki Forest virus

<400> SEQUENCE: 18
gcaggucaca ccaaaugacc augcaaaugc cagagcauuu ucgcaccugg c          51

<210> SEQ ID NO 19
<211> LENGTH: 51
<212> TYPE: RNA
<213> ORGANISM: Middelburg virus

<400> SEQUENCE: 19
gcaggucaca ccgaaugacc augcuaacgc gagggcguuu ucgcaccuug c          51

<210> SEQ ID NO 20
<211> LENGTH: 51
<212> TYPE: RNA
<213> ORGANISM: Barmah Forest virus

<400> SEQUENCE: 20
gcagaccaca ccaaacgauc augcacacgc gagggcguuu ucgcaccuug c          51
```

```
<210> SEQ ID NO 21
<211> LENGTH: 51
<212> TYPE: RNA
<213> ORGANISM: Ndumu virus

<400> SEQUENCE: 21
gcaggucaca ccgaaugacc augcuaaugc aagagcguuu ucgcaucuug c          51

<210> SEQ ID NO 22
<211> LENGTH: 51
<212> TYPE: RNA
<213> ORGANISM: SES virus

<400> SEQUENCE: 22
gcaggucaca ccuaaugacc augccaaugc cagagcuuuu ucgcaucugg c          51

<210> SEQ ID NO 23
<211> LENGTH: 51
<212> TYPE: RNA
<213> ORGANISM: SPD virus

<400> SEQUENCE: 23
caauaggucg ucuaacgacc augccgccgc cagagcuuuc ucccacuugg c          51

<210> SEQ ID NO 24
<211> LENGTH: 8
<212> TYPE: PRT
<213> ORGANISM: Eilat virus

<400> SEQUENCE: 24

Asp Ile Gly Gly Ala Leu Val Glu
1               5

<210> SEQ ID NO 25
<211> LENGTH: 8
<212> TYPE: PRT
<213> ORGANISM: Eilat virus

<400> SEQUENCE: 25

Gly Val Gly Ala Ala Pro Ser Tyr
1               5

<210> SEQ ID NO 26
<211> LENGTH: 8
<212> TYPE: PRT
<213> ORGANISM: Eilat virus

<400> SEQUENCE: 26

Gly Ala Gly Gly Tyr Ile Phe Ser
1               5

<210> SEQ ID NO 27
<211> LENGTH: 8
<212> TYPE: PRT
<213> ORGANISM: Eilat virus

<400> SEQUENCE: 27

Thr Val Glu Trp Ser Ala Ile Val
1               5

<210> SEQ ID NO 28
<211> LENGTH: 8
<212> TYPE: PRT
<213> ORGANISM: Eilat virus
```

```
<400> SEQUENCE: 28

Arg Ala Arg Arg Ala Val Ala Pro
1               5

<210> SEQ ID NO 29
<211> LENGTH: 9
<212> TYPE: PRT
<213> ORGANISM: Trocara virus

<400> SEQUENCE: 29

Asp Ile Gly Gly Ala Ala Leu Val Asp
1               5

<210> SEQ ID NO 30
<211> LENGTH: 8
<212> TYPE: PRT
<213> ORGANISM: Trocara virus

<400> SEQUENCE: 30

Gly Ile Gly Cys Ala Pro Ser Tyr
1               5

<210> SEQ ID NO 31
<211> LENGTH: 8
<212> TYPE: PRT
<213> ORGANISM: Trocara virus

<400> SEQUENCE: 31

Gly Val Gly Gly Tyr Ile Phe Ser
1               5

<210> SEQ ID NO 32
<211> LENGTH: 8
<212> TYPE: PRT
<213> ORGANISM: Trocara virus

<400> SEQUENCE: 32

Thr Val Lys Trp Ser Ala Ala Thr
1               5

<210> SEQ ID NO 33
<211> LENGTH: 8
<212> TYPE: PRT
<213> ORGANISM: Trocara virus

<400> SEQUENCE: 33

Arg Pro Lys Arg Ser Thr Glu Leu
1               5

<210> SEQ ID NO 34
<211> LENGTH: 8
<212> TYPE: PRT
<213> ORGANISM: Aura virus

<400> SEQUENCE: 34

Asp Ala Gly Ala Ala Leu Val Glu
1               5

<210> SEQ ID NO 35
<211> LENGTH: 8
<212> TYPE: PRT
<213> ORGANISM: Aura virus

<400> SEQUENCE: 35
```

Gly Ser Gly Ala Ala Pro Ser Tyr
1               5

<210> SEQ ID NO 36
<211> LENGTH: 8
<212> TYPE: PRT
<213> ORGANISM: Aura virus

<400> SEQUENCE: 36

Gly Val Gly Gly Tyr Ile Phe Ser
1               5

<210> SEQ ID NO 37
<211> LENGTH: 8
<212> TYPE: PRT
<213> ORGANISM: Aura virus

<400> SEQUENCE: 37

Thr Val Glu Trp Ser Arg Ala Ile
1               5

<210> SEQ ID NO 38
<211> LENGTH: 8
<212> TYPE: PRT
<213> ORGANISM: Aura virus

<400> SEQUENCE: 38

Arg His Val Arg Ser Thr Pro Thr
1               5

<210> SEQ ID NO 39
<211> LENGTH: 8
<212> TYPE: PRT
<213> ORGANISM: Whataroa virus

<400> SEQUENCE: 39

Asp Ile Gly Ala Ala Leu Val Glu
1               5

<210> SEQ ID NO 40
<211> LENGTH: 8
<212> TYPE: PRT
<213> ORGANISM: Whataroa virus

<400> SEQUENCE: 40

Gly Val Gly Ala Ala Pro Ser Tyr
1               5

<210> SEQ ID NO 41
<211> LENGTH: 8
<212> TYPE: PRT
<213> ORGANISM: Whataroa virus

<400> SEQUENCE: 41

Gly Val Gly Gly Tyr Ile Phe Ser
1               5

<210> SEQ ID NO 42
<211> LENGTH: 8
<212> TYPE: PRT
<213> ORGANISM: Whataroa virus

<400> SEQUENCE: 42

Thr Glu Glu Trp Ser Ala Ala Ala

```
<210> SEQ ID NO 43
<211> LENGTH: 8
<212> TYPE: PRT
<213> ORGANISM: Whataroa virus

<400> SEQUENCE: 43

Arg His Lys Arg Ser Ile Thr Asp
1               5

<210> SEQ ID NO 44
<211> LENGTH: 8
<212> TYPE: PRT
<213> ORGANISM: Sindbis virus

<400> SEQUENCE: 44

Asp Ile Gly Ala Ala Leu Val Glu
1               5

<210> SEQ ID NO 45
<211> LENGTH: 8
<212> TYPE: PRT
<213> ORGANISM: Sindbis virus

<400> SEQUENCE: 45

Gly Val Gly Ala Ala Pro Ser Tyr
1               5

<210> SEQ ID NO 46
<211> LENGTH: 8
<212> TYPE: PRT
<213> ORGANISM: Sindbis virus

<400> SEQUENCE: 46

Gly Val Gly Gly Tyr Ile Phe Ser
1               5

<210> SEQ ID NO 47
<211> LENGTH: 8
<212> TYPE: PRT
<213> ORGANISM: Sindbis virus

<400> SEQUENCE: 47

Thr Glu Glu Trp Ser Ala Ala Pro
1               5

<210> SEQ ID NO 48
<211> LENGTH: 8
<212> TYPE: PRT
<213> ORGANISM: Sindbis virus

<400> SEQUENCE: 48

Arg Ser Lys Arg Ser Val Ile Asp
1               5

<210> SEQ ID NO 49
<211> LENGTH: 8
<212> TYPE: PRT
<213> ORGANISM: Western equine encephalomyelitis virus

<400> SEQUENCE: 49

Glu Ala Gly Ala Gly Ser Val Glu
1               5
```

<210> SEQ ID NO 50
<211> LENGTH: 8
<212> TYPE: PRT
<213> ORGANISM: Western equine encephalomyelitis virus

<400> SEQUENCE: 50

Glu Ala Gly Arg Ala Pro Ala Tyr
1               5

<210> SEQ ID NO 51
<211> LENGTH: 8
<212> TYPE: PRT
<213> ORGANISM: Western equine encephalomyelitis virus

<400> SEQUENCE: 51

Glu Ala Gly Ala Tyr Ile Phe Ser
1               5

<210> SEQ ID NO 52
<211> LENGTH: 8
<212> TYPE: PRT
<213> ORGANISM: Western equine encephalomyelitis virus

<400> SEQUENCE: 52

Ser Glu Ser Trp Ser Leu Val Thr
1               5

<210> SEQ ID NO 53
<211> LENGTH: 8
<212> TYPE: PRT
<213> ORGANISM: Western equine encephalomyelitis virus

<400> SEQUENCE: 53

Arg Gln Lys Arg Ser Ile Thr Asp
1               5

<210> SEQ ID NO 54
<211> LENGTH: 8
<212> TYPE: PRT
<213> ORGANISM: Eastern equine encephalomyelitis virus

<400> SEQUENCE: 54

Glu Ala Gly Ala Gly Ser Val Glu
1               5

<210> SEQ ID NO 55
<211> LENGTH: 8
<212> TYPE: PRT
<213> ORGANISM: Eastern equine encephalomyelitis virus

<400> SEQUENCE: 55

Glu Ala Gly Arg Ala Pro Ser Ala
1               5

<210> SEQ ID NO 56
<211> LENGTH: 8
<212> TYPE: PRT
<213> ORGANISM: Eastern equine encephalomyelitis virus

<400> SEQUENCE: 56

Glu Ala Gly Ala Tyr Ile Phe Ser
1               5

<210> SEQ ID NO 57

```
<211> LENGTH: 8
<212> TYPE: PRT
<213> ORGANISM: Eastern equine encephalomyelitis virus

<400> SEQUENCE: 57

Ser Glu Pro Trp Ser Leu Ala Thr
1               5

<210> SEQ ID NO 58
<211> LENGTH: 8
<212> TYPE: PRT
<213> ORGANISM: Eastern equine encephalomyelitis virus

<400> SEQUENCE: 58

Arg Thr Arg Arg Asp Leu Asp Thr
1               5

<210> SEQ ID NO 59
<211> LENGTH: 8
<212> TYPE: PRT
<213> ORGANISM: Venezuelan equine encephalitis virus

<400> SEQUENCE: 59

Glu Ala Gly Ala Gly Ser Val Glu
1               5

<210> SEQ ID NO 60
<211> LENGTH: 8
<212> TYPE: PRT
<213> ORGANISM: Venezuelan equine encephalitis virus

<400> SEQUENCE: 60

Glu Ala Gly Cys Ala Pro Ser Tyr
1               5

<210> SEQ ID NO 61
<211> LENGTH: 8
<212> TYPE: PRT
<213> ORGANISM: Venezuelan equine encephalitis virus

<400> SEQUENCE: 61

Asp Ala Gly Ala Tyr Ile Phe Ser
1               5

<210> SEQ ID NO 62
<211> LENGTH: 8
<212> TYPE: PRT
<213> ORGANISM: Venezuelan equine encephalitis virus

<400> SEQUENCE: 62

Cys Glu Gln Trp Ser Leu Val Thr
1               5

<210> SEQ ID NO 63
<211> LENGTH: 8
<212> TYPE: PRT
<213> ORGANISM: Venezuelan equine encephalitis virus

<400> SEQUENCE: 63

Arg Lys Arg Arg Ser Thr Glu Glu
1               5

<210> SEQ ID NO 64
<211> LENGTH: 8
<212> TYPE: PRT
```

```
<213> ORGANISM: Chikungunya virus

<400> SEQUENCE: 64

Arg Ala Gly Ala Gly Ile Ile Glu
1               5

<210> SEQ ID NO 65
<211> LENGTH: 8
<212> TYPE: PRT
<213> ORGANISM: Chikungunya virus

<400> SEQUENCE: 65

Arg Ala Gly Cys Ala Pro Ser Tyr
1               5

<210> SEQ ID NO 66
<211> LENGTH: 8
<212> TYPE: PRT
<213> ORGANISM: Chikungunya virus

<400> SEQUENCE: 66

Arg Ala Gly Gly Tyr Ile Phe Ser
1               5

<210> SEQ ID NO 67
<211> LENGTH: 8
<212> TYPE: PRT
<213> ORGANISM: Chikungunya virus

<400> SEQUENCE: 67

Ala Glu Glu Trp Ser Leu Ala Ile
1               5

<210> SEQ ID NO 68
<211> LENGTH: 8
<212> TYPE: PRT
<213> ORGANISM: Chikungunya virus

<400> SEQUENCE: 68

Arg Gln Arg Arg Ser Ile Lys Asp
1               5

<210> SEQ ID NO 69
<211> LENGTH: 8
<212> TYPE: PRT
<213> ORGANISM: Ross River virus

<400> SEQUENCE: 69

Arg Ala Gly Ala Gly Val Val Glu
1               5

<210> SEQ ID NO 70
<211> LENGTH: 8
<212> TYPE: PRT
<213> ORGANISM: Ross River virus

<400> SEQUENCE: 70

Thr Ala Gly Cys Ala Pro Ser Tyr
1               5

<210> SEQ ID NO 71
<211> LENGTH: 8
<212> TYPE: PRT
<213> ORGANISM: Ross River virus
```

```
<400> SEQUENCE: 71

Arg Ala Gly Ala Tyr Ile Phe Ser
1               5

<210> SEQ ID NO 72
<211> LENGTH: 8
<212> TYPE: PRT
<213> ORGANISM: Ross River virus

<400> SEQUENCE: 72

Thr Glu Glu Trp Ser Ala Ala Leu
1               5

<210> SEQ ID NO 73
<211> LENGTH: 8
<212> TYPE: PRT
<213> ORGANISM: Ross River virus

<400> SEQUENCE: 73

Arg His Arg Arg Ser Val Thr Glu
1               5

<210> SEQ ID NO 74
<211> LENGTH: 8
<212> TYPE: PRT
<213> ORGANISM: Una virus

<400> SEQUENCE: 74

Arg Ala Gly Ala Gly Val Val Glu
1               5

<210> SEQ ID NO 75
<211> LENGTH: 8
<212> TYPE: PRT
<213> ORGANISM: Una virus

<400> SEQUENCE: 75

Thr Ala Gly Cys Ala Pro Ala Tyr
1               5

<210> SEQ ID NO 76
<211> LENGTH: 8
<212> TYPE: PRT
<213> ORGANISM: Una virus

<400> SEQUENCE: 76

Arg Ala Gly Gly Tyr Thr Phe Ser
1               5

<210> SEQ ID NO 77
<211> LENGTH: 8
<212> TYPE: PRT
<213> ORGANISM: Una virus

<400> SEQUENCE: 77

Thr Val Glu Trp Ser Ala Pro Leu
1               5

<210> SEQ ID NO 78
<211> LENGTH: 8
<212> TYPE: PRT
<213> ORGANISM: Una virus

<400> SEQUENCE: 78
```

Arg His Arg Arg Ser Val Thr Gln
1               5

<210> SEQ ID NO 79
<211> LENGTH: 8
<212> TYPE: PRT
<213> ORGANISM: Semliki Forest virus

<400> SEQUENCE: 79

His Ala Gly Ala Gly Val Val Glu
1               5

<210> SEQ ID NO 80
<211> LENGTH: 8
<212> TYPE: PRT
<213> ORGANISM: Semliki Forest virus

<400> SEQUENCE: 80

Thr Ala Gly Cys Ala Pro Ser Tyr
1               5

<210> SEQ ID NO 81
<211> LENGTH: 8
<212> TYPE: PRT
<213> ORGANISM: Semliki Forest virus

<400> SEQUENCE: 81

Arg Ala Gly Ala Tyr Ile Phe Ser
1               5

<210> SEQ ID NO 82
<211> LENGTH: 8
<212> TYPE: PRT
<213> ORGANISM: Semliki Forest virus

<400> SEQUENCE: 82

Ser Glu Glu Trp Ser Ala Pro Leu
1               5

<210> SEQ ID NO 83
<211> LENGTH: 8
<212> TYPE: PRT
<213> ORGANISM: Semliki Forest virus

<400> SEQUENCE: 83

Arg His Arg Arg Ser Val Ser Gln
1               5

<210> SEQ ID NO 84
<211> LENGTH: 8
<212> TYPE: PRT
<213> ORGANISM: Middelburg virus

<400> SEQUENCE: 84

Arg Ala Gly Ala Gly Val Val Asn
1               5

<210> SEQ ID NO 85
<211> LENGTH: 8
<212> TYPE: PRT
<213> ORGANISM: Middelburg virus

<400> SEQUENCE: 85

Thr Ala Gly Cys Ala Pro Ser Tyr
1               5

```
<210> SEQ ID NO 86
<211> LENGTH: 8
<212> TYPE: PRT
<213> ORGANISM: Middelburg virus

<400> SEQUENCE: 86

Arg Ala Gly Ala Tyr Ile Phe Ser
1               5

<210> SEQ ID NO 87
<211> LENGTH: 8
<212> TYPE: PRT
<213> ORGANISM: Middelburg virus

<400> SEQUENCE: 87

Thr Glu Glu Trp Thr Ala Leu Val
1               5

<210> SEQ ID NO 88
<211> LENGTH: 8
<212> TYPE: PRT
<213> ORGANISM: Middelburg virus

<400> SEQUENCE: 88

Arg Arg Arg Arg Gly Leu Thr Glu
1               5

<210> SEQ ID NO 89
<211> LENGTH: 8
<212> TYPE: PRT
<213> ORGANISM: Barmah Forest virus

<400> SEQUENCE: 89

Arg Ala Gly Glu Gly Val Val Glu
1               5

<210> SEQ ID NO 90
<211> LENGTH: 8
<212> TYPE: PRT
<213> ORGANISM: Barmah Forest virus

<400> SEQUENCE: 90

Pro Ala Gly Ser Ala Pro Ala Tyr
1               5

<210> SEQ ID NO 91
<211> LENGTH: 8
<212> TYPE: PRT
<213> ORGANISM: Barmah Forest virus

<400> SEQUENCE: 91

Arg Ala Gly Gly Tyr Ile Phe Ser
1               5

<210> SEQ ID NO 92
<211> LENGTH: 8
<212> TYPE: PRT
<213> ORGANISM: Barmah Forest virus

<400> SEQUENCE: 92

Ser Val Glu Trp Ser Ala Ala Ala
1               5
```

```
<210> SEQ ID NO 93
<211> LENGTH: 8
<212> TYPE: PRT
<213> ORGANISM: Barmah Forest virus

<400> SEQUENCE: 93

Arg Pro Lys Arg Ser Val Ala His
1               5

<210> SEQ ID NO 94
<211> LENGTH: 8
<212> TYPE: PRT
<213> ORGANISM: Ndumu virus

<400> SEQUENCE: 94

Arg Ala Gly Ala Gly Val Val Glu
1               5

<210> SEQ ID NO 95
<211> LENGTH: 8
<212> TYPE: PRT
<213> ORGANISM: Ndumu virus

<400> SEQUENCE: 95

Arg Ala Gly Ala Ala Pro Ala Tyr
1               5

<210> SEQ ID NO 96
<211> LENGTH: 8
<212> TYPE: PRT
<213> ORGANISM: Ndumu virus

<400> SEQUENCE: 96

Arg Ala Gly Ala Tyr Ile Phe Ser
1               5

<210> SEQ ID NO 97
<211> LENGTH: 8
<212> TYPE: PRT
<213> ORGANISM: Ndumu virus

<400> SEQUENCE: 97

Ser Val Glu Trp Ser Ala Ala Ala
1               5

<210> SEQ ID NO 98
<211> LENGTH: 8
<212> TYPE: PRT
<213> ORGANISM: Ndumu virus

<400> SEQUENCE: 98

Arg His Arg Arg Ala Ala Gln His
1               5

<210> SEQ ID NO 99
<211> LENGTH: 8
<212> TYPE: PRT
<213> ORGANISM: SES virus

<400> SEQUENCE: 99

Arg Ala Gly Ala Gly Val Val Glu
1               5

<210> SEQ ID NO 100
<211> LENGTH: 8
```

```
<212> TYPE: PRT
<213> ORGANISM: SES virus

<400> SEQUENCE: 100

Pro Ala Gly Thr Ala Pro Asn Tyr
1               5

<210> SEQ ID NO 101
<211> LENGTH: 8
<212> TYPE: PRT
<213> ORGANISM: SES virus

<400> SEQUENCE: 101

Arg Ala Gly Ala Tyr Ile Phe Ser
1               5

<210> SEQ ID NO 102
<211> LENGTH: 8
<212> TYPE: PRT
<213> ORGANISM: SES virus

<400> SEQUENCE: 102

Thr Val Glu Trp Ser Ala Leu Thr
1               5

<210> SEQ ID NO 103
<211> LENGTH: 8
<212> TYPE: PRT
<213> ORGANISM: SES virus

<400> SEQUENCE: 103

Arg Gly Lys Arg Ser Val Ala Ser
1               5

<210> SEQ ID NO 104
<211> LENGTH: 8
<212> TYPE: PRT
<213> ORGANISM: SPD virus

<400> SEQUENCE: 104

Gly Ala Gly Ala Thr Ile Ile Asp
1               5

<210> SEQ ID NO 105
<211> LENGTH: 8
<212> TYPE: PRT
<213> ORGANISM: SPD virus

<400> SEQUENCE: 105

Met Val Gly Ala Ala Pro Gly Tyr
1               5

<210> SEQ ID NO 106
<211> LENGTH: 8
<212> TYPE: PRT
<213> ORGANISM: SPD virus

<400> SEQUENCE: 106

Gly Leu Gly Gly Tyr Ile Phe Ser
1               5

<210> SEQ ID NO 107
<211> LENGTH: 8
<212> TYPE: PRT
<213> ORGANISM: SPD virus
```

```
<400> SEQUENCE: 107

Ala Ile Pro Trp Thr Arg Ala Pro
1               5

<210> SEQ ID NO 108
<211> LENGTH: 8
<212> TYPE: PRT
<213> ORGANISM: SPD virus

<400> SEQUENCE: 108

Arg Arg Lys Arg Ala Val Ser Thr
1               5

<210> SEQ ID NO 109
<211> LENGTH: 24
<212> TYPE: RNA
<213> ORGANISM: Eilat virus

<400> SEQUENCE: 109
cccucuacaa cuaaccuaaa uagu                                         24

<210> SEQ ID NO 110
<211> LENGTH: 24
<212> TYPE: RNA
<213> ORGANISM: Aura virus

<400> SEQUENCE: 110
accucuacgg ugguccuaaa uaga                                         24

<210> SEQ ID NO 111
<211> LENGTH: 24
<212> TYPE: RNA
<213> ORGANISM: Whataroa virus

<400> SEQUENCE: 111
agcucuacgg cgguccuaaa uaga                                         24

<210> SEQ ID NO 112
<211> LENGTH: 24
<212> TYPE: RNA
<213> ORGANISM: Sindbis virus

<400> SEQUENCE: 112
aucucuacgg ugguccuaaa uagu                                         24

<210> SEQ ID NO 113
<211> LENGTH: 24
<212> TYPE: RNA
<213> ORGANISM: Western equine encephalomyelitis virus

<400> SEQUENCE: 113
cccucuacgg cugaccuaaa uagu                                         24

<210> SEQ ID NO 114
<211> LENGTH: 24
<212> TYPE: RNA
<213> ORGANISM: Eastern equine encephalomyelitis virus

<400> SEQUENCE: 114
cccucuacgg cugaccuaaa uagu                                         24

<210> SEQ ID NO 115
```

```
<211> LENGTH: 24
<212> TYPE: RNA
<213> ORGANISM: Venezuelan equine encephalitis virus

<400> SEQUENCE: 115
cucucuacgg cuaaccugaa ugga                                           24

<210> SEQ ID NO 116
<211> LENGTH: 24
<212> TYPE: RNA
<213> ORGANISM: Chikungunya virus

<400> SEQUENCE: 116
cuuucuacgg cgguccugaa uggg                                           24

<210> SEQ ID NO 117
<211> LENGTH: 24
<212> TYPE: RNA
<213> ORGANISM: Ross River virus

<400> SEQUENCE: 117
accucuacgg ugguccuaaa uaga                                           24

<210> SEQ ID NO 118
<211> LENGTH: 24
<212> TYPE: RNA
<213> ORGANISM: Semliki Forest virus

<400> SEQUENCE: 118
accucuacgg cgguccuaga uugg                                           24

<210> SEQ ID NO 119
<211> LENGTH: 24
<212> TYPE: RNA
<213> ORGANISM: Middelburg virus

<400> SEQUENCE: 119
accucuacgg cgguccuaaa uagu                                           24

<210> SEQ ID NO 120
<211> LENGTH: 24
<212> TYPE: RNA
<213> ORGANISM: Barmah Forest virus

<400> SEQUENCE: 120
aucucuacgg ugguccuaaa uagu                                           24

<210> SEQ ID NO 121
<211> LENGTH: 24
<212> TYPE: RNA
<213> ORGANISM: SES virus

<400> SEQUENCE: 121
cgcucuacgg cuguccuaaa uaga                                           24

<210> SEQ ID NO 122
<211> LENGTH: 24
<212> TYPE: RNA
<213> ORGANISM: SPD virus

<400> SEQUENCE: 122
cccucuacgu cuaaccuuaa uauu                                           24
```

-continued

```
<210> SEQ ID NO 123
<211> LENGTH: 20
<212> TYPE: RNA
<213> ORGANISM: Eilat virus

<400> SEQUENCE: 123
aauuuguuuu uaauauuucc                                              20

<210> SEQ ID NO 124
<211> LENGTH: 19
<212> TYPE: RNA
<213> ORGANISM: Aura virus

<400> SEQUENCE: 124
auuuuguuuu uaauauuuc                                               19

<210> SEQ ID NO 125
<211> LENGTH: 19
<212> TYPE: RNA
<213> ORGANISM: Sindbis virus

<400> SEQUENCE: 125
auuuuguuuu uaacauuuc                                               19

<210> SEQ ID NO 126
<211> LENGTH: 19
<212> TYPE: RNA
<213> ORGANISM: Western equine encephalomyelitis virus

<400> SEQUENCE: 126
auuuuguuuu uaaaauuuc                                               19

<210> SEQ ID NO 127
<211> LENGTH: 19
<212> TYPE: RNA
<213> ORGANISM: Eastern equine encephalomyelitis virus

<400> SEQUENCE: 127
auuuuguuuu uaauauuuc                                               19

<210> SEQ ID NO 128
<211> LENGTH: 19
<212> TYPE: RNA
<213> ORGANISM: Venezuelan equine encephalitis virus

<400> SEQUENCE: 128
auuuuguuuu uaauauuuc                                               19

<210> SEQ ID NO 129
<211> LENGTH: 21
<212> TYPE: RNA
<213> ORGANISM: Ross River virus

<400> SEQUENCE: 129
gauuuguuuu uaauauuuua c                                            21

<210> SEQ ID NO 130
<211> LENGTH: 19
<212> TYPE: RNA
<213> ORGANISM: Semliki Forest virus

<400> SEQUENCE: 130
aauugguuuu uaauauuuc                                               19
```

<210> SEQ ID NO 131
<211> LENGTH: 19
<212> TYPE: RNA
<213> ORGANISM: Middelburg virus

<400> SEQUENCE: 131
cuauugguuu uaauauucc                                                    19

<210> SEQ ID NO 132
<211> LENGTH: 21
<212> TYPE: RNA
<213> ORGANISM: Barmah Forest virus

<400> SEQUENCE: 132
auuuguuuuu uaauauuuua c                                                 21

<210> SEQ ID NO 133
<211> LENGTH: 25
<212> TYPE: RNA
<213> ORGANISM: SPD virus

<400> SEQUENCE: 133
cuauugguuu uaaaauuuuc aauac                                             25

<210> SEQ ID NO 134
<211> LENGTH: 13510
<212> TYPE: DNA
<213> ORGANISM: Artificial Sequence
<220> FEATURE:
<223> OTHER INFORMATION: Recombinant Alphavirus

<400> SEQUENCE: 134
ataggctgca cattacacat tagaaatcgt aacgtagcct tccactttca tcgaacatgg        60
agaaaccaac tgttaacgtc gacgtagacc cccaaagtcc gttcgtactg cagttgcaga      120
aacacttccc ccagtttgag atagtggcta acatggtcac cccgaatgac cacgccaatg      180
cgagagcctt ctcccattgc gccagtaaac tgatcgaagc ggaggtacct gttaccacgc      240
cgatcatcga catagggagc gcacctgctc gtagaatgta ttccgagcac cgctaccact      300
gcgtttgccc tatgaaatgc ccagaagatc cggaccgcct taccacctat gcgaaccgcc      360
ttgtcgaaaa cgccacgaag atcgctaaca acggctaga cgctaagcta caagacctta      420
agcaagtctt agaaactcct gacatagaaa cggactcgat ctgcttccac gacgacgcta      480
catgccgttg ggtagcggag gtctctgtca tgcaggacgt gtacatagac gcccccagct      540
ctatctacca ccaagcacta aaaggcatcc gcaaaatata ctggattggc ttcgacacca      600
cgccgttcat gttcaaagca ctcgccggat cttacccctc gtacaacacc aactgggccg      660
acgagaaagt actcgaagca cgaaacatcg gcctatgcag taccacactg agcgaaggat      720
cgacagggaa actgtcgatc atgcgaaaga gagattgtt acctggtgct caggtctact      780
tttctgttgg gtcaacactg taccctgaaa accgctccaa tcttatgagt tggcacctcc      840
cttccgtgtt ccatctgaag ggtagaaacg cattcacttg ccgctgtgac acagtggtca      900
actgcgacgg ttacgtggtt aagaaaataa ccattagccc caacctcata ggtacaccag      960
caggatacgc ggtgactaac aacagtgagg gattcttact ttgtaaagtc actgacactg     1020
tacgcggcga acgggtttcg ttccccgtgt gcatgagtat accggcaacc atctgcgacc     1080
aaatgactgg catactagcc acagacataa acccggaaga cgcacaaaaa ctgctggttg     1140
ggctcaacca gcgtattgtc gtcaacggaa agaccaaccg aaacgtcaac acgatgcaga     1200

-continued

```
accatcttct accggcagta gcacaaggat ttagcaaatg ggccaaggaa cgcaaagcag    1260
acggagacga cgagaaacat ctcgggactc gtgaacgctc cttaaccttc ggatgtctct    1320
gggcgtttag gaccaagaaa gtacactcat tctaccgccc acctggtaca cagaccatcg    1380
tcaaggtgga atcagtgttc acagcgtcgc cccttgccat ccccatccgg caaacatctt    1440
tgcctatctc actgcgcctg aagcttaaga tggcgatagc aaagaagcaa acaacccca    1500 tcgctactat cacacagacg caaattacga acgccatcga attccaaaaa gaagctactg    1560
aaacggcgcg cgcggttgaa ctcaacaatg ctctcccgcc cctgcgtgcc accgaacagg    1620
atccgacacc ttctgtagaa cacgtcgtct gcgaggtaga agaactctcc gacgacatcg    1680
gcggggcgct ggtcgagacc ccacgtggac acgtgcgaat cttaccccag ccaaccgatg    1740
tcaaggtagg gaactacctt gtcatctccc cgcaagctgt gcttcgaaac gataaattaa    1800
gtagactaca cccctagca gagcaaataa aggtcatcac acacaccggg cgcaagggcc    1860
gatacgaagt ggcgccgtat agcggaaaaa tgctactacc atgcggtacc tccgtcccat    1920
ggcctcagtt ctgcgcactt gctgaaagtg caaccctagt gttcaacgaa cgagaaatga    1980
tcgaccgtaa attagcgtat atcgcacagc acggcccagc cttgaacaca gacgaggaac    2040
aatacaaggt tatcaaagca tcagcagcag acagcgaata cgtgttcgac atcgaccgaa    2100
tgaggtgcgt gccgacaaaa gaggcaaacg gtctagtatt ggtagggaa ctcacacaac    2160 caccctacca cgaactcgct atgcagggtc tatatactag accagccgca ccctatccaa    2220
tagagaccat aggtgtcatc ggcacgccag gctccgggaa atcagcgatc attaagaaca    2280
ccgtcaccac caaagaccct cgtcactagtg gcaagaaaga gaactgcaaa gagatagaaa    2340
ctgacgtact ccgccttcgc aacctcgtca ttaagagccg cacggtggac tccgtgctac    2400
tcaacggttg cacccaagag gtagacgttc tacacgtaga cgaggcattc gcgtgtcacg    2460
ccggaacgtt gttagctctc atcgctatcg taaaaccgcg ttgtaaagta gtactgtacg    2520
gagacccgaa acaatgcggc ttcttcaatc tcatgcagat caaagtccat ttcaacaacc    2580
cggaggttga cgtctgctcc caattacact acaagtatat atccaggcgc tgcatcctgc    2640
ctgtcaccgc catcgtatct tccatacatt acgacggcaa aatgcgcaca acgaacaccg    2700
ccgaccaacg tatagagatt gatactacag ggacctcgaa gccgaaaccg accgacctca    2760
tcctcacatg cttccgcgga tgggttaaac agctccaact cgagtatccc cgtaacgaag    2820
taatgaccgc agccgcctct caaggcctga cccgtaaacg tgtatatgct gtccgctaca    2880
aggtcaatga gaacccctc tacgccttta cttcagaaca cgtgaacgtg ctgcttacca    2940
ggacggaaca taccctagta tggaaaacgc tacaaggaga tccatggatc aagcacctgt    3000
ccaatgtacc gaaaggaaac ttctccgcga cggtcgacga atggcacgcc gagcacgaac    3060
gcatcatgaa cgccatccgc atgcccaccc ccgaagtcaa tgccttctct tgtaagacta    3120
acgtatgctg ggcgaaggca cttgtaccgg tcttggcgac cgctggtctg aagctctctg    3180
gcgcccaatg gacagagctg ttcccccaat tcgaaagaga cgaaccgcac tcagctacgt    3240
ttgctcttga cgtcttatgc ataaagtact tcggaatgga cctcactagc ggcatcttcg    3300
ccaaaccgac agtgcccttg accttccacc cggtaagccg ttatcacccg caagcacact    3360
gggacaacgc caacggagaa caacgctacg gattcgaccc tgacatcgcc aaggcactcg    3420
cacgccgatt cccagtgttc tctcaggccg ctaaaggaca tgccatctca cctatccttg    3480
gtacgacgca cactctttca agccgcgaca actacgtgcc cgtcaaccgt attgtcccgc    3540
```

-continued

| | | | | | |
|---|---|---|---|---|---|
| acacactgaa | aggagagtac | acgtatgtca | aacaagattc | ccttgcatcc | gttctctctg | 3600 |
| ctgtgcaagc | attttcagtc | ttagttgtct | cgtcagagcc | catcgcgagc | gccacgaagc | 3660 |
| aaatcacttg | ggtggcccg | ctaggcacag | ccggctgcat | acacacgcac | aggctgccct | 3720 |
| ggggcttccc | aaaaatgtcg | ttacacgatg | ccgtggcagt | caatatggag | accgaatacc | 3780 |
| gaggacatca | ctaccagcaa | tgcgaagatc | acgtcgccat | cctcaagacc | ctgggcaagt | 3840 |
| ctgccctcgc | caacctaaga | cctggcggca | ccctgattct | gcgcacctac | ggttacgcgg | 3900 |
| accgcaacag | cgagaatgta | atcactgcac | ttgcccgcaa | gttcgcgaga | gtaactgcag | 3960 |
| tcaggtctag | taaccctca | agcaataccg | aaatctactt | gatcttcagg | aaattcgaca | 4020 |
| acaaccgatc | cagacagttt | accttgcatc | atcttaaccg | cgcgatttcc | gcgctctacg | 4080 |
| aaagtccatg | cgaccccgac | ggagtgggcg | ccgccccatc | atactcggtg | atcagaggcg | 4140 |
| acataaccgc | gactaactcc | cacgccattg | tcgtccctgt | cacgccggag | cgaaaagacg | 4200 |
| gcgtgtatcg | cgcttgtagc | aagaaatggg | gccccctacc | tcgcctggag | tggaccgaag | 4260 |
| gtgccacctt | gttctcgccc | ggttcaccag | ccactctgca | agtatgtgta | ccctcgctcc | 4320 |
| agaatacgga | cactacatca | acccagcaag | cctaccgcgc | catcgccaaa | gttgtcgtcg | 4380 |
| acgagcagat | tccgtcacta | tctctacccg | tcctcaccat | gaagaagacc | ggcacagcag | 4440 |
| acaccgtatc | agaatccttg | aaccacctag | ttaccgctct | ggaccaaacc | gatgcaaatg | 4500 |
| taactattta | ctgtctcgac | aaaagcaggc | tcataaaaat | caaggaagta | attgcacgca | 4560 |
| aggaagccgt | caccgagctt | atcgacgacg | acctagaaat | cgacgaggaa | ctgacatggg | 4620 |
| tccaccccga | tagctgccta | cgcaaccgca | ccggttttag | caccgacaaa | ggaaaactgt | 4680 |
| actcatatct | ggaagggacc | aagttccacc | agatggccaa | ggacttcgca | gagattaggt | 4740 |
| cactattccc | tgacgagatg | gaagctaacg | aacacatatg | ctcactcatc | ttaggggaaa | 4800 |
| cgatagatgg | catccgagaa | cgctgtccag | tgacagacaa | tccgccatca | tcaccgccca | 4860 |
| agactgtacc | ctgcttgtgc | atgtacgcca | tgacccagga | acgcgcccta | cggctcaaga | 4920 |
| gcaattctgt | cacccaaatc | acagtctgct | cgtccttcgt | tctcaagaag | caccacatca | 4980 |
| aaggggtaca | gaagatccaa | tgcacggcac | ctatgttatt | caacccgaca | ccattaactt | 5040 |
| ccaggacggt | ccgcactccg | ccacaagtct | cagcacgagc | cgcactcgat | cttcctcccg | 5100 |
| ttgcacctat | gccttctgta | cctgcaccgg | ttagcctgac | gcctacgagg | cgtgcaccac | 5160 |
| caccgcccct | taccaaacga | cccgttgtcg | tacgtccgtc | gacgcctcca | ccgccgccac | 5220 |
| cagtacgcca | gacaccaacg | ccagtgctcg | cgccacggac | tggttctacg | gcagcaccca | 5280 |
| ctccgacgcc | acgcctctcg | ttatctacgg | accagccatc | cgtagacatt | tcgttcggag | 5340 |
| acttttcccc | cgcagaaacg | atgtctttga | tgctgtcgtc | ccctggctct | gacaccgcca | 5400 |
| gtatcacctt | cggtgacttc | gacgaggacg | aggtagaatc | tatagtagga | cgggaatatt | 5460 |
| gactaaccgg | agcgggaggg | tacatatttt | cttcagacac | cggcagtggg | catttacaac | 5520 |
| aacgttcggt | ccttcaaaac | cgcacgaccg | agacaattat | agagcgagtc | acacatgacc | 5580 |
| gcatccacgc | cccacagctc | aatgaagcca | gggaagaagt | tctgaagtta | agtaccaaa | 5640 |
| tgtatccctc | cgacgctaac | aaaagtaggt | accgcgcccg | caaagtagag | aaccaaaaag | 5700 |
| ccatatgcat | cagccgcctc | acggcaggta | gccgcagtta | ttctttcgga | acaacagaag | 5760 |
| ccgaatgcta | cagagaaact | taccctgcag | tcatgtactc | gtcttcgcta | ccatcctcct | 5820 |
| actcggcgcc | gaccacggct | gtggctgtgt | gcaacgcgta | tctggcagct | aattacccca | 5880 |
| ccgtcgcctc | gtatcagatc | actgacgagt | acgacgcgta | cttagacatg | gtcgacggta | 5940 |

```
ctatggcttg cttagacaca gcgtccttca acccttctaa actaaggagt tttccgaagg    6000
tccacaagta tctggaacct actatccgta gtgcagtacc atctcccttc cagaatacac    6060
tacaaaacgt tctaactgcc gccactaagc gtaactgtaa cgtcacccaa atgcgcgagc    6120
taccgacact cgattctgcc gcatttaacg tagagtgctt taggaaatac gcctgcaaca    6180
acgactactg gcaagaatat gcggataaac ctatccgcat aactacggaa tacgtcaccg    6240
cctacgttgc caagctaaag ggacctaaag ctgccgcctt gttttccaaa acacacgact    6300
taccggcgct cggcgaagta cctatggacc gcttcgtcat ggacatgaag agagacgtta    6360
aagtgacccc tggcagtaag cacaccgaag aacgcccgaa agttcaggta attcaagcag    6420
ctgaacctct ggccactgcc tacttatgcg gcatccatcg tgaactggtc cggcgactca    6480
ctgctgcgct ccttcccaac atccacactc tttttgacat gtccgcagag gacttcgacg    6540
ccacactggc ccaccacttc aaaaagggcg accccgtact ggaaacagac atagcatcct    6600
tcgacaaaag tcaggatgac gccttagcac tcacagggct aatgatcctg gaggacctag    6660
gagtagacca gccccctcatg gacctgatcg aggcagcttt cggagatata accagcacgc    6720
acctacccac cggagcacgt ttccggtttg gcgccatgat gaagtctggt atgtttctta    6780
ccctgttcat caacaccgtc cttaacgtgg taatagccag ccgtgtatta aagacaagt    6840 taacgcactc cgcctgcgcc gcattcatcg gcgacgacaa catcatacac ggagtcatat    6900
ctgaccgtat aatggctgac cgatgcgcta catggatgaa tatggaagtc aaaattatag    6960
acgcggtcat gggagactac cctccctatt tctgtggcgg gttcctcatc atagacagcg    7020
tgaccaacac cgcatgccga gtcgccgacc ccctgaagag actattcaaa cttgggaagc    7080
cgcttaccgc ggacgacgac cacgacgatg accggagaag agccctcgag gatgaaacta    7140
aagcatggtt tcgggtaggg atcagagaag gcatcaccgc cgccgtatca tcaagatacg    7200
aagtcgacaa catactgccc gttctcttag cccttagaac cttttgcttta tctacgcgca    7260 acttctctgc cttacgggga acacttaaga ccctctacaa ctaacctaaa tagtgcgcgt    7320
attatcaata ctactagcac actattaccc gtgtacgtac caacggcact acttgcacaa    7380
gtcaacatgg agtttatccc aacccaaact ttctacaata ggaggtacca gcctcgacct    7440
tggactccgc gccctactat ccaagtcatc agacccagac cgcgtccgca aaggaaggcc    7500
gggcaacttg cccagctgat ctcagcagtt aataaactga caatgcgcgt ggtacctcaa    7560
cagaagccgc gcaagaatcg gaagaataag aagcaaaagc aaaagcagca ggcgccacga    7620
aacaatacga atcaaaagaa gcagcccccc aaaaagaaac cggttcaaaa gaaaagaag    7680 ccgggccgca gagagagaat gtgcatgaaa atcgaaaatg attgcatctt cgaagtcaag    7740
catgaaggta aggtaacagg ttacgcgtgc ttggtagggg acaaagtaat gaagccagca    7800
cacgtaaagg ggaccatcga taacgcggac ctggccaaat tggccttcaa gcggtcatct    7860
aagtacgacc ttgaatgcgc gcagataccc gtgcacatga gtccgacgc ttcgaagttc    7920 acccatgaga aaccggaggg gtactacaac tggcaccacg gagcagtaca gtactcagga    7980
ggccgattca ccatccctac aggtgcgggc aaaccagggg atagtggtag accgatcttc    8040
gacaacaagg ggcgcgtggt ggccatagtt ttaggaggag ctaatgaagg agcccgtaca    8100
gccctctcgg tggtgacctg gaacaaagac atcgtcacga aaatcacccc tgaggggcc    8160 gaagagtgga gtctggccat tccagttatg tgcctgctgg caaataccac gttccctgc    8220 tcccggcccc cttgcacacc ctgctgctac gaaaaagagc cggagaaaac cttgcgcatg    8280
```

```
cttgaagaca atgtcatgag ccccgggtac tatcagctgc tacaagcatc cttaacatgt   8340
tctccccgac gccagcggcg cagtattaag gaccacttca atgtctataa agccacaaga   8400
ccgtacctag ctcactgtcc cgactgtgga aagggcact cgtgccatag tcccgtagcg    8460
ctagaacgca tcagaaacga agcgacagac gggacgttga aaatccaggt ttccttgcaa   8520
atcggaataa agacggatga tagccatgat tggaccaagc tgcgttatat ggacaatcac   8580
atgccagcag acgcagagcg ggccgggcta tttgtaagaa cgtcagcacc gtgcacgatt   8640
actgaacaa tgggacactt cattctggcc cgatgtccga aaggagaaac tctgacggcg    8700
gggttcactg acggtaggaa gatcagtcac tcatgtacgc acccatttca ccatgaccct   8760
cctgtgatag gccgggaaaa attccattcc cgaccgcagc acggtaggga actaccttgc   8820
agcacgtacg cgcagagcac cgctgcaact gccgaggaga tagaggtaca catgcccca   8880
gacacccag atcgcacatt aatgtcacaa cagtccggca atgtaaagat cacagtcaat   8940
agtcagacgg tgcggtacaa gtgcaattgt ggtgactcaa gtgaaggatt aaccactaca   9000
gataaagtga ttaataactg caaggtcgat caatgccatg ccgcggtcac caatcacaaa   9060
aaatggcagt ataattcccc tctggtcccg cgtaatgctg aattcgggga ccggaaagga   9120
aaagttcaca ttccatttcc tctggcaaat gtgacatgca gggtgcctaa agcaagaaac   9180
cccaccgtga cgtacggaaa aaaccaagtc atcatgttgc tgtatcctga ccacccaacg   9240
ctcctgtcct acaggaatat gggagaagaa ccaaactatc aagaagagtg ggtgacgcat   9300
aagaaggaga tcaggttaac cgtgccgact gaggggctcg aggtcacgtg gggtaacaat   9360
gagccgtaca agtattggcc gcagttatcc acaaacggta cagcccacgg ccacccgcat   9420
gagataattc tgtattatta tgagctgtac ccaactatga ctgcggtagt tttgtcagtg   9480
gcctcgttca tactcctgtc gatggtgggt gtggcagtgg ggatgtgcat gtgtgcacga   9540
cgcagatgca ttacaccgta cgaactgaca ccaggagcta ccgtcccttt cctgcttagc   9600
ctaatatgct gcattagaac agctaaagcg gccacatacc aggaggccgc ggtatacctg   9660
tggaacgagc agcagccttt attttggatg caagccctta ttccgctggc agccctgatt   9720
gtcctatgta actgtctgag actcttacca tgctgttgta aaatgttgac tttttttagcc   9780
gtactgagcg tcggtgccca cactgtgagc gcgtacgaac acgtaacagt gatcccgaac   9840
acggtgggag taccgtataa gactctagtc aacagaccgg gctacagccc catggtattg   9900
gagatggagc ttctgtctgt caccttggaa ccaacgctat cgcttgatta catcacgtgc   9960
gagtataaaa ccgttatccc gtctccgtac gtgaaatgct gcggtacagc agagtgtaag  10020
gacaagagcc tacctgatta cagctgtaag gtcttcaccg gcgtctaccc attcatgtgg  10080
ggcggcgcct actgcttctg cgacaccgaa aatacgcaat tgagcgaagc acatgtggag  10140
aagtccgaat catgcaaaac agaatttgca tcagcataca gggctcatac cgcatccgca  10200
tcagctaagc tccgcgtcct ttaccaagga aataatatca ctgtggctgc ttatgcaaac  10260
ggcgaccatg ccgtcacagt taaggacgct aaattcatag tggggccaat gtcttcagcc  10320
tggacacctt tcgacaataa aatcgtggtg tacaaaggcg acgtctacaa catggactac  10380
ccgcccttcg gcgcaggaag accaggacaa tttggcgaca tccaaagtcg cacgcctgag  10440
agcgaagacg tctatgctaa tacacaactg gtactgcaga gaccgtccgc gggtacggtg  10500
cacgtgccgt actctcaggc accatctggc ttcaagtatt ggctaaaaga acgaggggcg  10560
tcgctgcagc acacagcacc atttggctgt caaatagcaa caaacccggt aagagcgatg  10620
aactgcgccg tagggaacat gcctatctcc atcgacatac cggacgcggc ctttaccagg  10680
```

```
gtcgtcgacg cgccatcttt aacggacatg tcgtgtgagg tatcagcctg cacccattcc   10740
tcagactttg ggggcgtagc catcattaaa tatgcagcca gtaagaaagg caagtgtgca   10800
gtgcactcga tgactaacgc cgtcactatt cgggaagctg aaatagaagt agaagggaac   10860
tctcagttgc aaatctcttt ttcgacggcc ctagccagcg ccgaatttcg cgtacaagtc   10920
tgttctacac aagtacactg tgcagccgag tgccatccac cgaaagacca tatagtcaat   10980
tacccggcgt cacacaccac cctcggggtc caagacattt ccgctacggc gatgtcatgg   11040
gtgcagaaga tcacgggagg tgtgggactg gttgtcgctg ttgcagcact gatcctaatc   11100
gtggtgctat gcgtgtcgtt tagcaggcac taacattatc acttaagaac ccgcccacat   11160
atatagggct acatagttca cgggaaagaa caaccccta atagtaacaa acaataaaa    11220 gtacaaaaac aggtatcagc cccttagcgc tgcataatct atagttcacg ggaaagaaca   11280
aacccctaat agtaacaaaa ctgcaaaaca caaaacagg tatcagcccc ttagagctgc    11340
ataatcacat agtccacggg acagatcaac cccctattag caacaaaaca caaatccca    11400 aaaacaggta taagtaccct tagtacttac tagtactcac tctagttcac agggaagaac   11460 aaccctaaa tagtaactaa acacaaaacc caaaaacagg tataggtacc cttagtacct   11520
ccaatttgcc catccatcgg gcccgctcaa gccgaactca cagagacgta ggccccgaac   11580
tccaaggaga cgtagggata aaagtgctga actcacagag acgtaagcac aacaatttgt   11640
ttttaatatt tccaaaaaaa aaaaaaaaa aaaaaaaag cggccgctcg aggggaatta   11700
attcttgaag acgaaagggc caggtggcac ttttcgggga aatgtgcgcg gaaccccctat  11760 ttgtttattt ttctaaatac attcaaatat gtatccgctc atgagacaat aaccctgata   11820
aatgcttcaa taatattgaa aaaggaagag tatgagtatt caacatttcc gtgtcgccct   11880
tattcccttt tttgcggcat tttgccttcc tgttttgct cacccagaaa cgctggtgaa    11940
agtaaaagat gctgaagatc agttgggtgc acgagtgggt tacatcgaac tggatctcaa   12000
cagcggtaag atccttgaga gttttcgccc cgaagaacgt tttccaatga tgagcacttt   12060
taaagttctg ctatgtggcg cggtattatc ccgtgttgac gccgggcaag agcaactcgg   12120
tcgccgcata cactattctc agaatgactt ggttgagtac tcaccagtca cagaaaagca   12180
tcttacggat ggcatgacag taagagaatt atgcagtgct gccataacca tgagtgataa   12240
cactgcggcc aacttacttc tgacaacgat cggaggaccg aaggagctaa ccgctttttt   12300
gcacaacatg gggatcatg taactcgcct tgatcgttgg gaaccggagc tgaatgaagc    12360
cataccaaac gacgagcgtg acaccacgat gcctgtagca atggcaacaa cgttgcgcaa   12420
actattaact ggcgaactac ttactctagc ttcccggcaa caattaatag actggatgga   12480
ggcggataaa gttgcaggac cacttctgcg ctcggccctt ccggctggct ggtttattgc   12540
tgataaatct ggagccggtg agcgtgggtc tcgcggtatc attgcagcac tggggccaga   12600
tggtaagccc tcccgtatcg tagttatcta cacgacgggg agtcaggcaa ctatggatga   12660
acgaaataga cagatcgctg agataggtgc ctcactgatt aagcattggt aactgtcaga   12720
ccaagtttac tcatatatac tttagattga tttaaaactt catttttaat ttaaaaggat   12780
ctaggtgaag atccttttg ataatctcat gaccaaaatc ccttaacgtg agttttcgtt    12840
ccactgagcg tcagaccccg tagaaaagat caaaggatct tcttgagatc ctttttttct   12900
gcgcgtaatc tgctgcttgc aaacaaaaaa accaccgcta ccagcggtgg tttgtttgcc   12960
ggatcaagag ctaccaactc tttttccgaa ggtaactggc ttcagcagag cgcagatacc   13020
```

```
aaatactgtc cttctagtgt agccgtagtt aggccaccac ttcaagaact ctgtagcacc    13080
gcctacatac ctcgctctgc taatcctgtt accagtggct gctgccagtg gcgataagtc    13140
gtgtcttacc gggttggact caagacgata gttaccggat aaggcgcagc ggtcgggctg    13200
aacgggnggt tcgtgcacac agcccagctt ggagcgaacg acctacaccg aactgagata    13260
cctacagcgt gagcattgag aaagcgccac gcttcccgaa gggagaaagg cggacaggta    13320
tccggtaagc ggcagggtcg gaacaggaga gcgcacgagg gagcttccag ggggaaacgc    13380
ctggtatctt tatagtcctg tcgggtttcg ccacctctga cttgagcgtc gatttttgtg    13440
atgctcgtca gggggcgga gcctatggaa aaacgccagc aacgcgagct cgatttaggt    13500
gacactatag                                                          13510
```